(12) United States Patent
Oba et al.

(10) Patent No.: US 12,202,528 B2
(45) Date of Patent: Jan. 21, 2025

(54) INFORMATION PROCESSING APPARATUS, MOVING APPARATUS, METHOD AND PROGRAM

(71) Applicant: Sony Semiconductor Solutions Corporation, Kanagawa (JP)

(72) Inventors: Eiji Oba, Tokyo (JP); Kohei Kadoshita, Tokyo (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 437 days.

(21) Appl. No.: 17/420,126

(22) PCT Filed: Dec. 25, 2019

(86) PCT No.: PCT/JP2019/050983
§ 371 (c)(1),
(2) Date: Jun. 30, 2021

(87) PCT Pub. No.: WO2020/145161
PCT Pub. Date: Jul. 16, 2020

(65) Prior Publication Data
US 2022/0081009 A1 Mar. 17, 2022

(30) Foreign Application Priority Data
Jan. 8, 2019 (JP) ................................. 2019-000975

(51) Int. Cl.
*B60W 60/00* (2020.01)
*B60W 40/08* (2012.01)
(Continued)

(52) U.S. Cl.
CPC ........ *B60W 60/0059* (2020.02); *B60W 40/08* (2013.01); *B60W 50/082* (2013.01);
(Continued)

(58) Field of Classification Search
CPC ......... B60W 60/0059; B60W 60/0053; B60W 40/08; B60W 50/082; B60W 50/14;
(Continued)

(56) References Cited

U.S. PATENT DOCUMENTS

2008/0309616 A1* 12/2008 Massengill .............. A61B 5/16
345/156
2011/0205167 A1* 8/2011 Massengill ............ A61B 5/162
345/173
(Continued)

FOREIGN PATENT DOCUMENTS

CN  108137062 A    6/2018
DE  112016002612 T5  3/2018
(Continued)

OTHER PUBLICATIONS

International Search Report and English translation thereof mailed Mar. 24, 2020 in connection with International Application No. PCT/JP2019/050983.
(Continued)

*Primary Examiner* — Zhen Y Wu
(74) *Attorney, Agent, or Firm* — Wolf, Greenfield & Sacks, P.C.

(57) ABSTRACT

A configuration that decides whether or not a driver has alertness sufficient for manual driving by analyzing eye behaviors of the driver trying to solve a problem displayed on the display section is realized. It is made possible to decide whether or not the driver of a moving apparatus that can be driven in a driving mode that can be switched to automated driving and manual driving has alertness sufficient to return to manual driving on the basis of eye behaviors of the driver. An eye-behavior analyzing section that analyzes an eye behavior of the driver who observes a problem displayed on a display section and an alertness deciding section that decides alertness of the driver on the
(Continued)

basis of a result of the analysis by the eye-behavior analyzing section are included. The alertness deciding section analyzes whether or not the driver executes an eye behavior such as a fixation or a microsaccade for solving the problem, and decides whether or not the driver has alertness sufficient to return to manual driving.

19 Claims, 29 Drawing Sheets

(51) Int. Cl.
  *B60W 50/08* (2020.01)
  *B60W 50/14* (2020.01)
  *G06F 3/01* (2006.01)

(52) U.S. Cl.
  CPC ........ *B60W 50/14* (2013.01); *B60W 60/0053* (2020.02); *G06F 3/013* (2013.01); *B60W 2040/0818* (2013.01); *B60W 2050/146* (2013.01); *B60W 2540/215* (2020.02); *B60W 2540/225* (2020.02); *B60W 2540/229* (2020.02)

(58) Field of Classification Search
  CPC ..... B60W 2540/215; B60W 2540/225; B60W 2540/229; B60W 2040/0818; B60W 2050/146; G06F 3/013
  USPC ........................................... 340/576
  See application file for complete search history.

(56) References Cited

U.S. PATENT DOCUMENTS

| | | | | |
|---|---|---|---|---|
| 2012/0278766 A1* | 11/2012 | Massengill | ............ | A61B 3/113 715/846 |
| 2013/0304326 A1* | 11/2013 | Van Dongen | ....... | B60W 30/146 701/1 |
| 2014/0091917 A1* | 4/2014 | Pink | ................... | B60W 50/085 340/439 |
| 2015/0173665 A1* | 6/2015 | Yamataka | ................ | A61B 5/18 351/209 |
| 2017/0313319 A1* | 11/2017 | Kishi | ................... | G06V 20/597 |
| 2017/0334456 A1* | 11/2017 | Deligianni | ............... | A61B 5/18 |
| 2019/0056732 A1* | 2/2019 | Aoi | ........................ | G08B 21/06 |
| 2019/0263262 A1* | 8/2019 | Mimura | ............ | B60W 60/0053 |
| 2020/0017118 A1* | 1/2020 | Miyahara | .......... | B60W 60/0053 |
| 2020/0359954 A1* | 11/2020 | Sunagawa | .............. | A61B 5/162 |
| 2021/0039678 A1* | 2/2021 | Shojima | ............ | B60W 60/0051 |
| 2021/0146934 A1* | 5/2021 | Inagaki | .................. | G06V 40/18 |

FOREIGN PATENT DOCUMENTS

| | | |
|---|---|---|
| JP | 2005352895 A | 12/2005 |
| JP | 2008-225537 A | 9/2008 |
| JP | 2014-049138 A | 3/2014 |
| JP | 2015-115045 A | 6/2015 |
| JP | 2017-097518 A | 6/2017 |
| KR | 20080104019 A | 11/2008 |
| KR | 20180083252 A | 7/2018 |
| WO | WO-2017086079 A1 | 5/2017 |
| WO | WO-2017195405 A1 | 11/2017 |
| WO | WO-2018066023 A1 | 4/2018 |

OTHER PUBLICATIONS

International Written Opinion and English translation thereof mailed Mar. 24, 2020 in connection with International Application No. PCT/JP2019/050983.

International Preliminary Report on Patentability and English translation thereof mailed Jul. 22, 2021 in connection with International Application No. PCT/JP2019/050983.

Extended European Search Report dated Feb. 7, 2022 in connection with European Application No. 19909150.5.

* cited by examiner

F I G. 3
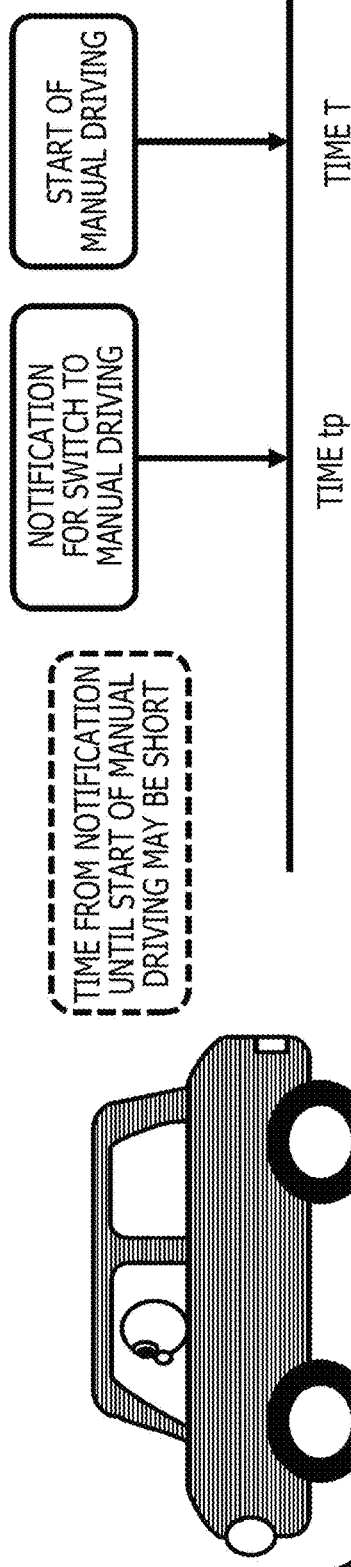
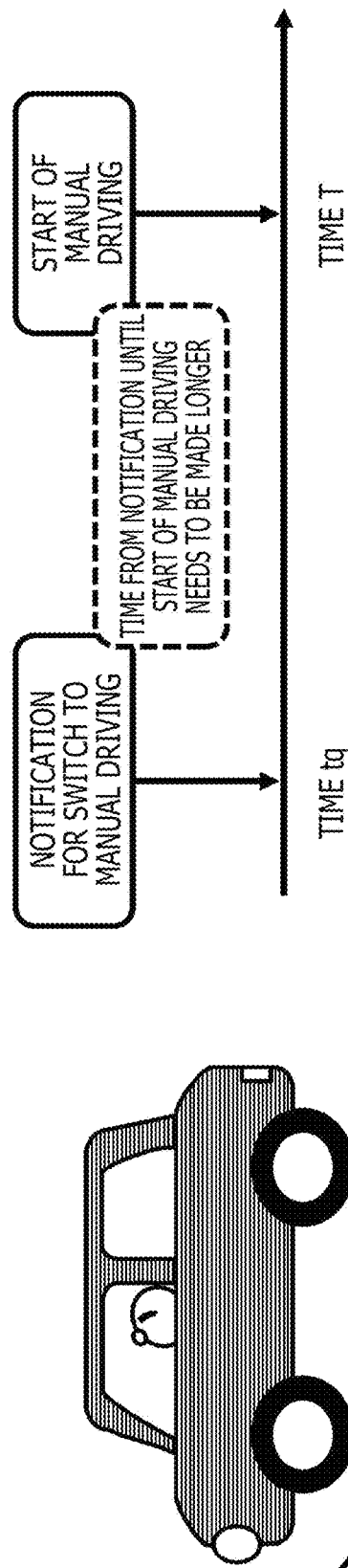

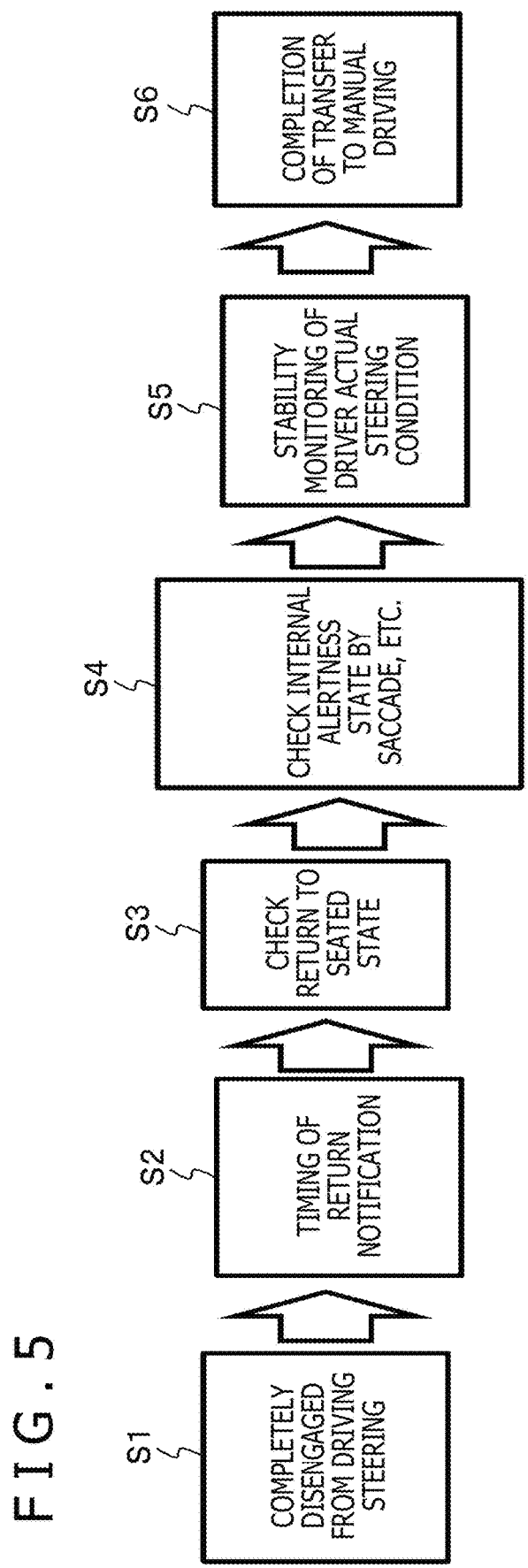
F I G . 5

FIG. 8
(c)
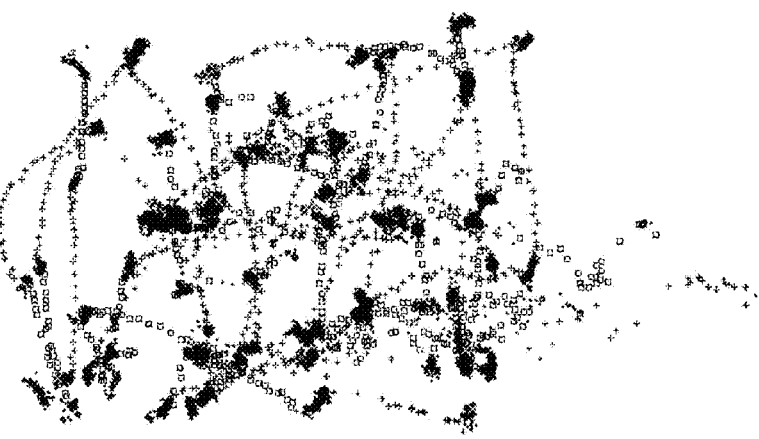
(b)
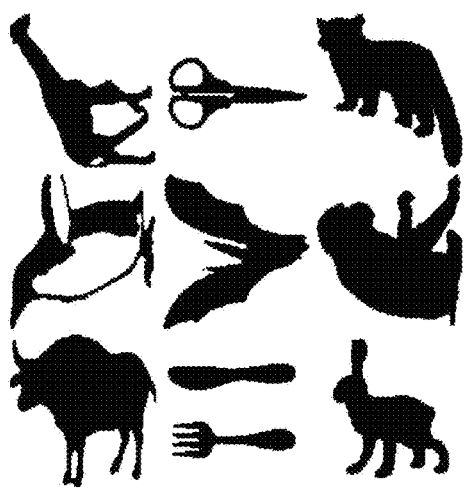
(a)
Q. COUNT SMALL ANIMAL(S)
Ans. A:0, B:1, C:2, D: 3 OR MORE

INFORMATION PROCESSING APPARATUS, MOVING APPARATUS, METHOD AND PROGRAM

CROSS-REFERENCE TO RELATED APPLICATIONS

This application claims the benefit under 35 U.S.C. § 371 as a U.S. National Stage Entry of International Application No. PCT/JP2019/050983, filed in the Japanese Patent Office as a Receiving Office on Dec. 25, 2019, which claims priority to Japanese Patent Application Number JP2019-000975, filed in the Japanese Patent Office on Jan. 8, 2019, each of which is hereby incorporated by reference in its entirety.

TECHNICAL FIELD

The present disclosure relates to an information processing apparatus, a moving apparatus, a method and a program. More specifically, present disclosure relates to an information processing apparatus, a moving apparatus, a method and a program by which the alertness state of driver of a vehicle is checked.

BACKGROUND ART

Lately, active technological development related to automated driving is underway.

Automated driving technologies are technologies that make it possible to automatically drive on roads by using various sensors such as position detection means provided to a vehicle (automobile), and it is predicted that the automated driving technologies will rapidly come into widespread use in the coming future.

However, in the current state, automated driving is under development, and thus, it is considered that it takes time until completely automated driving becomes possible, and it is predicted that, for the meantime, automobiles are driven by being switch to automated driving and manual driving by a driver as appropriate.

For example, it is predicted that a mode switch is necessary in which, while driving in the automated driving mode is performed on a straight road with a sufficient road width such as a freeway, in a case where an automobile has exited the freeway and the driver wants to park the automobile in a parking lot at a position where he/she wants to park it, in a case where the automobile is driving through a mountain path with a narrow road width, or in other similar situations, the driving mode needs to be switched to the manual driving mode, and an automobile is driven by manipulation by the driver.

While a vehicle is executing automated driving, the driver does not need to direct his/her line of sight in the forward direction which is the driving direction of the vehicle, and is allowed to engage in free actions like drowsing, watching TV, reading a book, or sitting backward and having a conversation with a person on the rear seat, for example.

In a case where, in a vehicle that is driven in the diving mode which is switched between automated driving and manual driving, it becomes necessary to switch from an automated driving mode to a manual driving mode, it becomes necessary to make the driver start manual driving.

However, if the driver drowses during the execution of automated driving, for example, the alertness of the driver lowers. That is, the consciousness level gets low. If the driving mode is switched to the manual driving mode in such a state that the alertness has lowered, normal manual driving cannot be performed, and there is a possibility that the driver causes an accident in the worst case.

In order to ensure the safety of driving, it is necessary to make the driver start manual driving in a state that the alertness of the driver is high, that is, the driver has a high consciousness.

If an automobile enters a manual driving zone after an automated driving zone, and the automated driving functionality is suspended while the driving return ability of the driver is still insufficient, there is a possibility that an accident occurs, and this is dangerous.

In order to prevent such a problem, it is necessary for a vehicle-side system (information processing apparatus) to decide whether or not the driver is at a level sufficient for execution of safe manual driving before the driving mode is switched from automated driving to manual driving.

As one technique to decide whether or not a driver is at a level sufficient for execution of safe manual driving, there are processes of examining the brain activity situation of the driver.

A representative process of examining the brain activity situation of a driver is a process of presenting problems to the driver, and examining answers to the problems.

Note that PTL 1 (JP 2008-225537A) discloses a configuration in which a question is output from a speaker to a driver, it is examined whether or not an answer to the question can be acquired by a microphone, and an alarm is output in a case where the answer cannot be acquired.

In addition, PTL 2 (JP 2015-115045A) discloses a configuration in which an instruction is output to a driver to manipulate a particular switch, and the alertness state of the driver is decided by measuring the length of time until the driver follows the instruction to perform correct manipulation.

However, the configurations described in these documents require answers from a driver to questions, or manipulation by a driver in response to an instruction, and generate burdens of the drivers. In addition, these processes take time for deciding the alertness of the drivers. Accordingly, there is a problem that those configurations are difficult to apply at times of emergencies, for example, in a case where the driving mode has to be switched from automated driving to manual driving immediately or in other similar situations.

CITATION LIST

Patent Literature

[PTL 1]
  JP 2008-225537A
[PTL 2]
  JP 2015-115045A

SUMMARY

Technical Problem

The present disclosure has been made in view of the problems mentioned above, for example, and an object of the present disclosure is to provide an information processing apparatus, a moving apparatus, a method and a program that make it possible to decide the alertness state of a driver in a short period of time and without generating excessive burdens on a driver.

A first aspect according to the present disclosure resides in an information processing apparatus including a display-information generating section that generates or acquires a problem and causes a display section to display the problem, an eye-behavior analyzing section that analyzes an eye behavior of a user who observes the problem displayed on the display section, and an alertness deciding section that decides alertness of the user on the basis of a result of the analysis by the eye-behavior analyzing section.

Further, a second aspect according to the present disclosure resides in a moving apparatus that is capable of being switched to automated driving and manual driving, the moving apparatus including a driver-information acquiring section that acquires driver information of a driver of the moving apparatus, and a data processing section that decides whether or not the driver has alertness sufficient to return to manual driving, on the basis of acquisition information of the driver-information acquiring section. The data processing section has a display-information generating section that generates or acquires a problem and causes a display section to display the problem, an eye-behavior analyzing section that analyzes an eye behavior of the driver who observes the problem displayed on the display section, and an alertness deciding section that decides alertness of the driver on the basis of a result of the analysis by the eye-behavior analyzing section.

Further, a third aspect according to the present disclosure resides in an information processing method executed in an information processing apparatus, the information processing method including a display-information generating step, performed by a display-information generating section, of generating or acquiring a problem and causing a display section to display the problem, an eye-behavior analyzing step, performed by an eye-behavior analyzing section, of analyzing an eye behavior of a user who observes the problem displayed on the display section, and an alertness deciding step, performed by an alertness deciding section, of deciding alertness of the user on the basis of a result of the analysis by the eye-behavior analyzing section.

Further, a fourth aspect according to the present disclosure resides in an information processing method executed in a moving apparatus, the moving apparatus being capable of being switched to automated driving and manual driving, the information processing method including a driver-information acquiring step, performed by a driver-information acquiring section, of acquiring driver information of a driver of the moving apparatus, and a data processing step, performed by a data processing section, of deciding whether or not the driver has alertness sufficient to return to manual driving, on the basis of the driver information. The data processing step includes a display-information generating step, performed by a display-information generating section, of generating or acquiring a problem, and causing a display section to display the problem, an eye-behavior analyzing step, performed by an eye-behavior analyzing section, of analyzing an eye behavior of a user who observes the problem displayed on the display section, and an alertness deciding step, performed by an alertness deciding section, of deciding alertness of the user on the basis of a result of the analysis by the eye-behavior analyzing section.

Further, a fifth aspect according to the present disclosure resides in a program that causes an information processing apparatus to execute information processing including a display-information generating step of causing a display-information generating section to generate or acquire a problem and cause a display section to display the problem, an eye-behavior analyzing step of causing an eye-behavior analyzing section to analyze an eye behavior of a user who observes the problem displayed on the display section, and an alertness deciding step of causing an alertness deciding section to decide alertness of the user on the basis of a result of the analysis by the eye-behavior analyzing section.

Note that the program according to the present disclosure is a program that can be provided by a storage medium or a communication medium that provides various program codes in a computer-readable format to an information processing apparatus or a computer system that can execute the various program codes, for example. By providing such a program in the computer-readable format, processes according to the program are realized on the information processing apparatus or the computer system.

Still other objects, features, and advantages of the present disclosure will become apparent from detailed explanations based on embodiments and attached drawings of the present disclosure mentioned below. Note that a system in the present specification has a logical set configuration of plural apparatuses, and is not limited to one that includes apparatuses of configurations that are housed within a single housing.

Advantageous Effects of Invention

According to the configuration of one embodiment according to the present disclosure, as means for determining whether or not a driver has alertness sufficient for manual driving when a driving mode is switched from an automated driving mode to a manual driving mode, a configuration that analyzes and decides eye behaviors of the driver of tracking visual information with his/her eyes trying to solve a problem displayed on a display section is realized.

Specifically, for example, it is made possible to decide whether or not the driver of the moving apparatus that can be driven in a driving mode that can be switched to automated driving and manual driving has alertness sufficient to return to manual driving on the basis of eye behaviors of the driver. An eye-behavior analyzing section that analyzes an eye behavior of a driver who observes a problem displayed on a display section and an alertness deciding section that decides alertness of the driver on the basis of a result of the analysis by the eye-behavior analyzing section are included. The alertness deciding section analyzes whether or not the driver executes an eye behavior such as a fixation or a microsaccade for solving the problem, and decides whether or not the driver has alertness sufficient to return to manual driving.

According to the present configuration, a configuration that decides whether or not the driver has alertness sufficient for manual driving by analyzing eye behaviors of the driver trying to solve the problem displayed on the display section is realized.

Note that advantages described in the present specification are presented merely for illustrative purposes, but not for limiting the advantages of the present disclosure. There may be additional advantages.

BRIEF DESCRIPTION OF DRAWINGS

FIG. 3 depicts figures each for explaining a process executed by the moving apparatus according to the present disclosure.

FIG. 5 is a figure depicting one example of a sequence of a mode switch from an automated driving mode to a manual driving mode executed by the moving apparatus according to the present disclosure.

FIG. 8 depicts figures for explaining examples of the locus of eye behaviors of a driver when a visual problem asking the driver to look at information is presented, and for explaining a difference between behaviors in cases of different alertness states.

DESCRIPTION OF EMBODIMENTS

Figure 1:
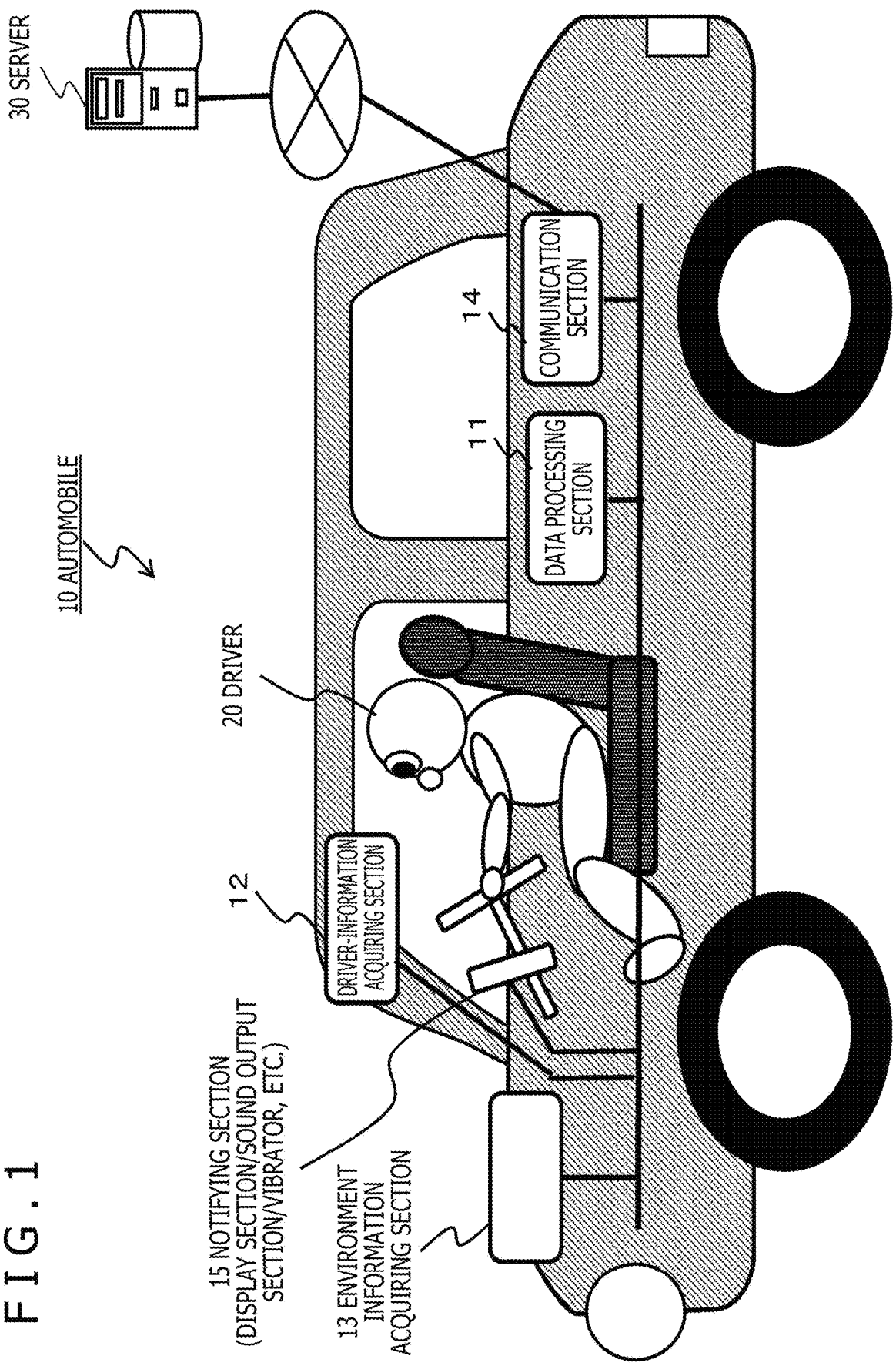
FIG. 1 is a figure for explaining one configuration example of a moving apparatus according to the present disclosure.

In the following, details of an information processing apparatus, a moving apparatus, a method and a program according to the present disclosure are explained with reference to the drawings. Note that the explanation is given according to the following items.

1. About Overview of Configurations and Processes of Moving Apparatus and Information Processing Apparatus 2. About Sequence of Mode Switch from Automated Driving Mode to Manual Driving Mode 3. About Driver Alertness Deciding Process Executed by Moving Apparatus and Information Processing Apparatus according to Present Disclosure 4. About Execution Configuration of Alertness Deciding Process in Information Processing Apparatus 5. About Specific Examples of Problems Presented to Driver for Deciding Alertness of Driver 6. About Sequence of Driver Alertness Deciding Process Executed by Information Processing Apparatus according to Present Disclosure 7. About Specific Configuration and Process Examples of Moving Apparatus 8. About Configuration Example of Information Processing Apparatus 9. Summary of Configuration according to Present Disclosure

[1. About Overview of Configurations and Processes of Moving Apparatus and Information Processing Apparatus]

Regarding vehicles for which only manual driving is permitted and partially automated driving vehicles in which systems perform partial driving assists, the responsibility of driving steering basically lies with drivers. In recent years, types of such vehicles on which driver monitoring systems are installed are increasing. Current driver monitoring systems basically observe the driving steering work of a driver, and detect disengagement of the driver from the steering or abnormalities.

Although it is predicted that automated driving vehicles capable of automated driving will be used more widely, it is considered that, in the coming future, automated driving zones which are road zones on which automated driving is allowed and manual driving zones which are road zones on which automated driving is not permitted will be present in a mixed fashion because of road infrastructures and the like. Drivers can perform automated driving in the automated driving zones, but have to return to manual driving when their automobiles are to enter the manual driving zones.

If driving assistance of vehicles and driving control control become more advanced and vehicle systems get to perform control of vehicles in a larger number of driving situations on their own initiative in the coming future, drivers may even fall asleep in automated driving zones in some situations. In addition, drivers can even be immersed in secondary tasks such as watching TV and videos, or playing games. However, if drivers fall asleep in automated driving zones, for example, the consciousness levels or determination levels of the drivers become low, that is, their alertness becomes low. If zones where automobiles can be driven by using automated driving functionalities are extended gradually in the coming future, situations occur where vehicles are kept driven normally safely even without the intervention of driving steering of the vehicles. Even in such use situations of automated driving functionalities, the drivers need to have returned to high alertness states in which they can drive the vehicles with normal consciousnesses before the vehicles enter manual driving zones.

However, regarding current driver monitoring systems, importance is placed on functionalities of detecting temporary lowering of attention such as lowering of the alertness of drivers. The current driver monitoring systems do not have a functionality of deciding the alertness of drivers about the levels of recovery when the drivers in states where their consciousnesses have completely been lowered have returned from those low-consciousness states.

The configuration according to the present disclosure solves the problem of such a current circumstance, and makes it possible to decide the alertness of a driver necessary for driving steering, especially, to decide details of a return to consciousness. The configuration according to the present disclosure estimates the state of perceptual cognitive activity in the brain of the driver, for example.

Specifically, behaviors of the eyes of the driver are analyzed, and the alertness of the driver is decided.

First, with reference to FIG. 1 and the subsequent figures, the overview of the configurations and processes of a moving apparatus and an information processing apparatus is explained.

The moving apparatus according to the present disclosure is, for example, an automobile that can be driven in a driving mode that is switched between automated driving and manual driving.

In a case where, in such an automobile, it becomes necessary to switch from an automated driving mode to a manual driving mode, it becomes necessary to make the driver start manual driving.

However, there are various processes (secondary tasks) that drivers perform during execution of automated driving.

For example, in some cases, drivers are only not holding steering wheels with their hands, but are gazing at the spaces in front of automobiles as they do if they are driving the automobiles, and, in some other cases, they are reading books or drowsing.

Due to differences between these processes, the alertness (consciousness levels) of drivers varies.

For example, if a driver drowses, the alertness of the driver lowers. That is, the consciousness level gets low. Normal manual driving cannot be performed in a state that the alertness is lowered in such a manner, and if the driving mode is switched to the manual driving mode in that state, there is a possibility that the driver causes an accident in the worst case.

In order to ensure the safety of driving, it is necessary to make the driver start manual driving in a state that the alertness of the driver is high, that is, the driver has a high consciousness.

For this purpose, it is necessary to change a notification timing of performing a request to switch from automated driving to manual driving according to the alertness of the driver during execution of automated driving.

That is, because the actual length of time required for the alertness of a driver to sufficiently return after notification varies, it is necessary to change the timing of notification according to return characteristics.

For example, in a case where a driver is looking forward and staring at a road during execution of automated driving, the alertness of the driver is high, that is, the driver can start manual driving at any time.

In such a case, it is sufficient if notification for a switch to manual driving is given at a timing immediately before the time when manual driving is necessary. This is because the driver can start safe manual driving promptly.

However, in a case where the driver is drowsing during execution of automated driving, the alertness of the driver is extremely low.

In such a case, if notification for a switch to manual driving is given at a timing immediately before the time when manual driving is necessary, the driver inevitably has to start manual driving in a state that the driver has a low consciousness. As a result, the possibility that the driver causes an accident increases. Accordingly, in such a case where the alertness is low, it is necessary to give notification for a switch to manual driving at an earlier step.

In a case where the alertness of the driver is low, notification for a switch to manual driving needs to be given earlier, and further even after the notification, a process of checking the transition of the alertness of the driver needs to be performed.

The moving apparatus according to the present disclosure or the information processing apparatus that can be mounted on the moving apparatus performs a process of deciding the alertness of the driver in a short period of time without generating significant burdens on the driver.

How early the notification is given is determined on the basis of various types of observable state information obtained by constantly monitoring the driver state. Driver-specific return characteristics including the length of time required for a driver to return and the like can be estimated from learning by using observable state information. An optimum return notification timing is determined from the observable state, and notification is given or an alarm is triggered. The timing at which it is necessary to check whether or not the alertness state of a driver is sufficient for a return to manual driving occurs at a step after the notification but before the steering of the vehicle is actually handed over to the driver.

First, with reference to FIG. 1 and the subsequent figures, the configurations and processes of the moving apparatus according to the present disclosure and the information processing apparatus that can be installed on the moving apparatus are explained.

FIG. 1 is a figure depicting one configuration example of an automobile 10 which is one example of the moving apparatus according to the present disclosure.

The information processing apparatus according to the present disclosure is installed on the automobile 10 depicted in FIG. 1.

The automobile 10 depicted in FIG. 1 is an automobile that can be driven in at least two driving modes which are a manual driving mode and an automated driving mode.

In the manual driving mode, driving based on manipulation by a driver 20, that is, manipulation (steering) of a steering wheel and manipulation of an accelerator, a brake and the like, is performed.

On the other hand, in the automated driving mode, manipulation by the driver 20 is not required, and, for example, driving based on sensor information of position sensors, other ambient information detection sensors and the like is performed.

The position sensors include a GPS receiver and the like, for example, and the ambient information detection sensors include cameras, ultrasonic sensors, radars, LiDARs (Light Detection and Ranging, Laser Imaging Detection and Ranging), sonars and the like, for example. These units of equipment are also referred to as positioning sensors.

Note that FIG. 1 is a figure for explaining the overview of the present disclosure, and schematically depicts main constituent elements. Detailed configurations are explained later.

As depicted in FIG. 1, the automobile 10 has a data processing section 11, a driver-information acquiring section 12, an environment information acquiring section 13, a communication section 14, and a notifying section 15.

The driver-information acquiring section 12 acquires information for deciding the alertness of the driver, manipulation information of the driver, and the like, for example. Specifically, for example, the driver-information acquiring section 12 includes cameras and sensors for detecting the face of the driver and motions of the eyes, manipulation information acquiring sections of manipulation sections (the steering wheel, the accelerator, the brake, etc.), and the like.

The environment information acquiring section 13 acquires driving environment information of the automobile 10. For example, the driving environment information includes information of images of spaces in front of, behind, and on the left and right side of the automobile; positional information from a GPS; information regarding surrounding obstacles from LiDARs (Light Detection and Ranging, Laser Imaging Detection and Ranging), sonars, and the like; and the like.

The data processing section 11 receives, as inputs, the driver information acquired by the driver-information acquiring section 12 and the environment information acquired by the environment information acquiring section 13, and executes an alertness deciding process of deciding whether or not the driver in the interior of the vehicle during automated driving is in a state that the driver can execute safe manual driving, that is, deciding whether or not the driver has alertness high enough to exhibit a determination ability and a physical ability necessary for performing manual driving, and the like.

Specific examples of the alertness deciding process are explained in detail later.

Further, for example, the data processing section 11 executes a process of notifying the driver to switch to the manual driving mode via the notifying section 15 in a case where it becomes necessary to switch from the automated driving mode to the manual driving mode, for example in a case where, while the automobile is driving in an automated driving zone where automated driving is permitted, a manual driving zone where automated driving is not permitted is approaching, or in other similar cases, and the like.

The timing of the notification process is an optimum timing computed by receiving inputs from the driver-information acquiring section 12 and the environment information acquiring section 13, for example.

That is, it is a timing that allows the driver 20 to start safe manual driving.

Specifically, the process is performed in such a manner that in a case where the alertness of the driver is high, the notification is given immediately before the time of the start of manual driving, for example, 30 seconds before the time, and in a case where the alertness of the driver is low, the notification is given 120 seconds before the time of the start of manual driving, leaving extra time, or in other similar manners.

The notifying section 15 includes a display section, a sound output section, or a vibrator on the steering wheel or a seat that gives the notification.

Figure 2:
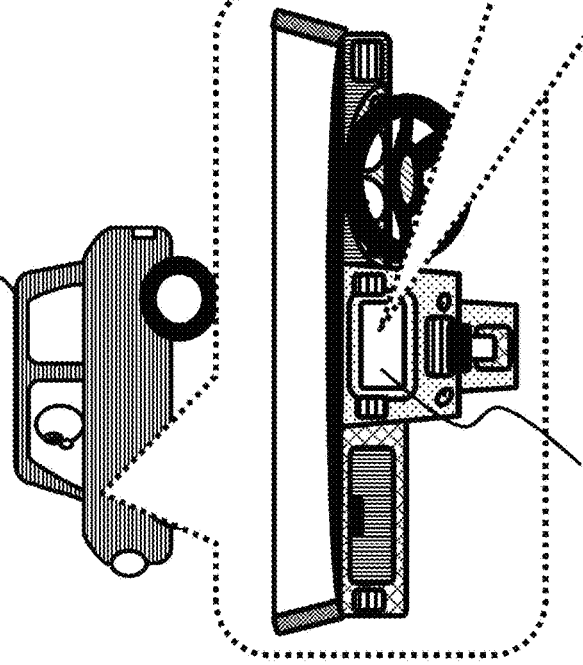
FIG. 2 is a figure for explaining one example of data displayed on a display section of the moving apparatus according to the present disclosure.

An example of a warning display on the display section included in the notifying section 15 is depicted in FIG. 2.

As depicted in FIG. 2, a display section 30 presents the following information as the display.

Driving mode information="DRIVING AUTOMATICALLY"

Warning display="SWITCH TO MANUAL DRIVING"

In the display area of the driving mode information, "DRIVING AUTOMATICALLY" is displayed at the time of execution of the automated driving mode, and "DRIVING MANUALLY" is displayed at the time of execution of the manual driving mode.

The display area of the warning display information is a display area where the following information is displayed while the automobile is executing automated driving in the automated driving mode. Note that, while the entire display screen is used in the present embodiment, part of the screen may be used for the display.

"SWITCH TO MANUAL DRIVING"

Note that, while an explanation is stated in a sentence in this example, the display is not limited to such a text display, and may include symbols such as pictograms, for example.

Note that the automobile 10 has a configuration that can communicate with a server 30 via the communication section 14 as depicted in FIG. 1.

For example, part of the process of computing a proper time of the notification output by the data processing section 11, specifically a training process, can be performed at the server 30.

FIG. 3 depicts figures each depicting a specific example of processes executed by the moving apparatus and the information processing apparatus according to the present disclosure.

FIG. 3 is a figure depicting examples of setting of a proper timing of notification requesting switching to manual driving while the automobile is executing automated driving in the automated driving mode, and depicts notification process examples in the following two examples.

(a) Notification process in a case where alertness of driver during execution of automated driving is high (b) Notification process in a case where alertness of driver during execution of automated driving is low The example of (a) is an example in which the driver is looking forward, and staring at a road during execution of automated driving. In this case, the alertness of the driver is high, that is, the driver can start manual driving at any time.

In such a case, even if notification for a switch to manual driving is given at a timing immediately before the time when manual driving is necessary, the driver can start safe manual driving promptly.

In the example of (b), in a case where the driver is drowsing during execution of automated driving, the alertness of the driver is extremely low.

In such a case, if notification for a switch to manual driving is given at a timing immediately before the time when manual driving is necessary, the driver inevitably starts manual driving in a state that the driver has a low consciousness, and the possibility that the driver causes an accident increases. Accordingly, in such a case where the alertness is low, it is necessary to give notification for a switch to manual driving at an earlier step.

As mentioned before, the driver needs to have sufficiently high alertness at the time point of the start of manual driving. That is, the driver needs to be in a state that the driver is capable of performing correct driving operation on the basis of a sure determination ability. In a case where the alertness of the driver is low, manual driving cannot be started.

In a case where the alertness of the driver is low, notification for a switch to manual driving needs to be given earlier, and further even after the notification, a process of checking the transition of the alertness of the driver needs to be performed.

The driver alertness deciding process is executed by the data processing section 11 by using information acquired by the driver-information acquiring section 12 of the automobile 10 depicted in FIG. 1, for example, and the like, while the automobile 10 is driving in an automated driving zone where automated driving is permitted, for example. In a case where it is decided that the alertness of the driver will not become high enough to start manual driving before the automobile 10 enters a manual driving zone, the data processing section 11 causes a driving control section to execute a danger avoidance process such as an emergency stop process or a deceleration process of the automobile 10.

Figure 4:
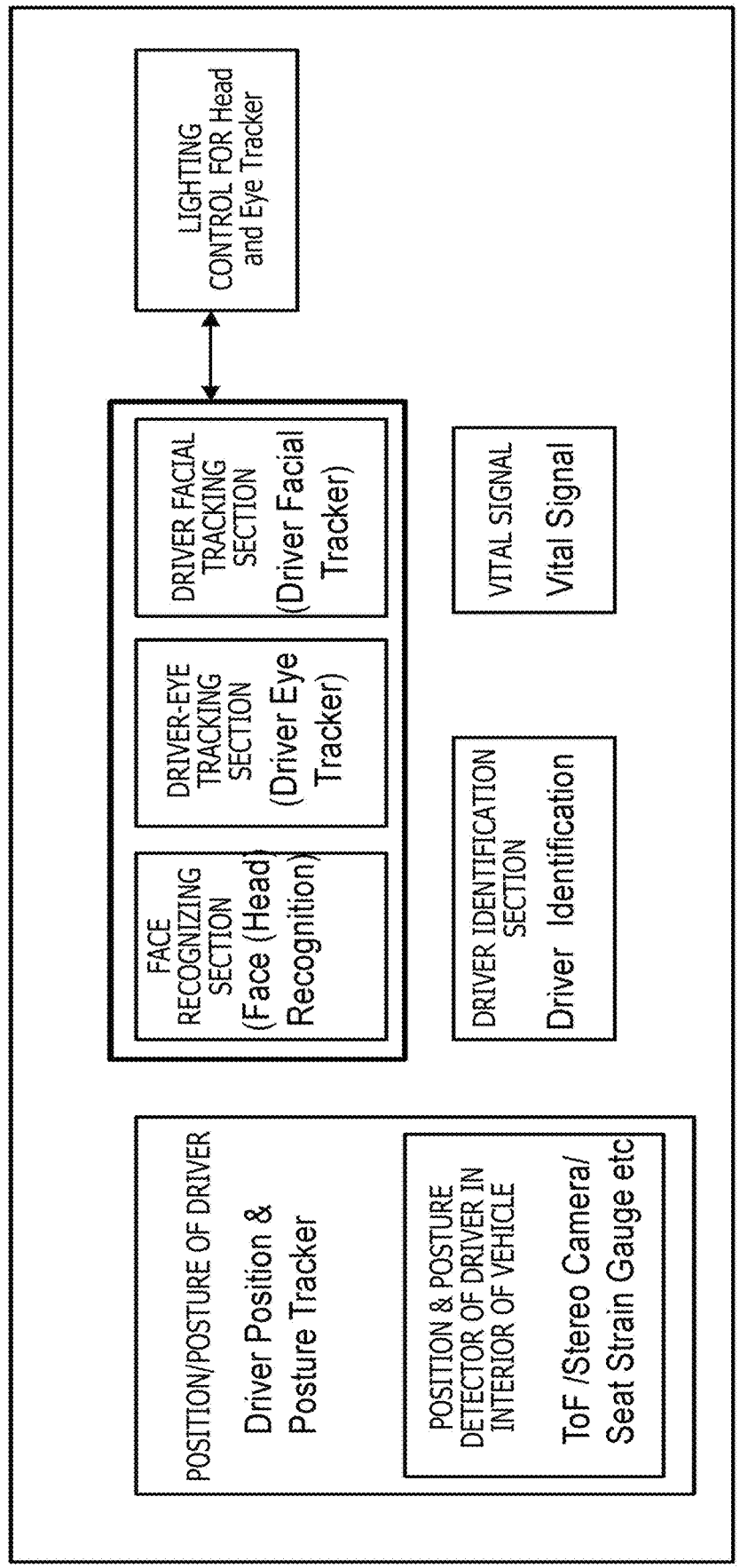
FIG. 4 is a figure for explaining a sensor configuration example of the moving apparatus according to the present disclosure.

A specific configuration example of the driver-information acquiring section 12 of the automobile 10 depicted in FIG. 1 is depicted in FIG. 4.

FIG. 4 depicts an example of various types of sensors that are included in the driver-information acquiring section 12 and are for obtaining information of the driver in the interior of the vehicle. For example, the driver-information acquiring section 12 includes a ToF camera, a stereo camera, a seat strain gauge, and the like as detectors for detecting the position and posture of the driver. In addition, a data acquiring section 102 includes, as detectors for obtaining vital activity observable information of the driver, a face recognizing section (Face (Head) Recognition), a driver-eye tracking section (Driver Eye Tracker), a driver facial tracking section (Driver Facial Tracker), and the like.

The driver-eye tracking section (Driver Eye Tracker) detects motions of the eyes of the driver.

The driver facial tracking section (Driver Facial Tracker) detects motions of the face and head of the driver.

Specifically, these include cameras and various sensors, for example. For example, they may have configurations using sensors such as EOG (Electro-Oculogram) sensors that perform measurement of the potentials of the eyes.

In addition, the driver-information acquiring section 12 includes a vital signal detector as a detector for obtaining vital activity observable information of the driver. In addition, the driver-information acquiring section 12 includes a driver identification section. Note that, other than knowledge-based identification using passwords, PIN numbers, and the like, examples of the method of identification that can be used include vital identification using faces, fingerprints, the irises of pupils, voiceprints, and the like.

[2. About Sequence of Mode Switch from Automated Driving Mode to Manual Driving Mode]

Next, a sequence of the transfer from the automated driving mode to the manual driving mode is explained.

FIG. 5 schematically depicts one example of the sequence of a mode switch from the automated driving mode to the manual driving mode executed by the data processing section 11 of the automobile 10 depicted in FIG. 1.

In Step S1, the driver is completely disengaged from driving steering. In this state, the driver can execute a secondary task such as taking a nap, watching a video, concentrating on a game, or engaging in work using a visual tool such as a tablet or a smartphone, for example. The work using a visual tool such as a tablet or a smartphone can be performed in a state that the driver's seat is moved out of position, or in a state that the driver is sitting on a seat other than the driver's seat, for example, in some possible cases.

Depending on the state of the driver like these, it is expected that the time required for the driver to return to manual driving when the automobile has approached a zone, on a route, where the automobile is required to return to manual driving varies significantly according to work contents that the driver is engaging in at that time. There is not enough time for the driver to return to manual driving if notification is given immediately before an event approaches in some cases, or in a case where notification is given too early in an attempt to leave extra time before an event approaches, the time until the timing at which the driver is actually required to return to manual driving becomes too long, in some other cases. As a result, if there are repetitive situations where notification is not given at right timings, the driver thinks notification timings of the system are not reliable, and becomes less aware of notification. This results in the driver becoming less attentive to right preparations. As a result, the risk that the transfer is not performed well increases, and, simultaneously, this also becomes a factor to inhibit comfortable execution of the secondary task. In view of this, the system needs to optimize notification timings in order for the driver to start right preparations for returning to driving in response to notification.

Step S2 corresponds to a timing of notification requesting return to manual driving like the one explained with reference to FIG. 2 before. In a dynamic and haptic manner by using vibrations or the like, or visually or auditorily, the driver is notified that the driver is requested to return to driving. For example, the data processing section 11 monitors the steady state of the driver, and grasps a timing to give notification, and notification is given as appropriate at such a timing that extra time can be left before the time when it actually is necessary to return to driving, and the return will succeed with a certain probability or higher. That is, it is desirable that the state of the execution of the secondary task by the driver is always monitored passively in the preceding passive monitoring period, the system can compute the optimum timing of the notification optimum timing, the passive monitoring in the period of Step S1 is always performed continuously, and return timings and return notification are determined according to driver-specific return characteristics.

That is, it is desirable that optimum return timings according to return action patterns of the driver, vehicle characteristics, and the like are learned, and a statistically-determined optimum timing that is required for the driver to normally return to manual driving from automated driving at a certain preset ratio or higher is presented to the driver. In this case, in a case where the driver did not respond to the notification in a certain length of time, a warning is given by an alarm or the like.

In Step S3, it is checked whether the driver has returned to the seated state. In Step S4, the internal alertness state of the driver is checked on the basis of the face or eye behavioral analysis about saccades (eye rotations) or the like. In Step S5, the degree of stability of the actual steering condition of the driver is monitored. Then, in Step S6, the transfer from automated driving to manual driving is completed.

[3. About Driver Alertness Deciding Process Executed by Moving Apparatus and Information Processing Apparatus according to Present Disclosure]

Next, the driver alertness deciding process executed by the moving apparatus and the information processing apparatus according to the disclosure is explained.

As mentioned before, the driver needs to have sufficiently high alertness at the time point of the start of manual driving. That is, the driver needs to be in a state that the driver is capable of performing correct driving operation on the basis of a sure determination ability. In a case where the alertness of the driver is low, manual driving cannot be started. In a case where the alertness of the driver is low, notification for a switch to manual driving needs to be given earlier, and further even after the notification, a process of checking the transition of the alertness of the driver needs to be performed.

The present disclosure makes it possible to decide whether or not the driver has alertness necessary for driving steering. The configuration according to the present disclosure estimates the state of perceptual cognitive activity in the brain of the driver, for example.

Specifically, behaviors of the eyes of the driver are analyzed, and the alertness of the driver is estimated or decided.

There are the following two main behavioral characteristics of the eyes of a human.

(a) Characteristics that motions of themselves are sensed by the three semicircular canals and the like, and vestibulo-ocular motions for cancelling the motions are performed.

(b) Eye behavioral characteristics that appear when supplementary information is searched for, and details are checked, in order to understand input information such as auditory, olfactory, or visual stimulus.

A process according to the present disclosure estimates or decides the alertness of the driver by analyzing the eye behavioral characteristics in (b) described above.

Specifically, visual problems are presented to the driver, and eye behaviors of the driver at the time the driver understands the presented problems and answers the problems are analyzed. The driver performs a process of capturing necessary visual information with his/her eyes for the cognitive understanding of the problems. Behaviors such as fixations, microsaccades (eye microrotations), or drifts that appear as eye behaviors at that time with the central visual field being directed toward a target are observed. From the behavioral analysis of the eye behaviors, the brain activity of the driver is estimated, and it is decided whether or not the driver has made a return sufficient for the cognitive understanding of the surrounding situation of the vehicle, that is, the alertness (alertness level) is decided.

Note that the series of operation described above of directing the line of sight toward a particular target is called a glance. The present disclosure is about a technology of performing alertness decisions with a focus on differences between behavioral features that appear at different mental/alertness states obtained by performing an analysis of eye behaviors in the glance in more detail and at still higher resolution.

Humans recognize information of surrounding environments by using the five senses. Among them, the amount of information obtained by the visual means, such as information that there is an enemy, is extremely large. An extremely large amount of diverse information enters through a visual field simultaneously and in parallel, and the information needs to be processed.

The information processing is roughly classified into conscious determination and unconscious determination. In a case where conscious determination is performed, for example, the central visual field of the line of sight is directed toward a determination target, detail features of the target are captured by the central visual field, and collation between the captured target object and memory information is executed.

The reason why the central visual field is directed to capture the target is because it is difficult to take in, visually into the brain, entire information that is within the visual field simultaneously and in parallel, and process the information. Accordingly, the visual system does not treat all the information of the visually outside world in the same way, and classifies information that is important in terms of biofunctions hierarchically by filtering. Further, the visual system sets the central visual field to a subject which is the determination target for identifying, at high resolution, a portion that is important for final action determination, and performs collation between memories and details of a particular local portion to be a feature of the subject.

At the time of this visual field adjustment process, a rotation behavior of eyes occurs. Note that a rotational movement of a head or a body merely appears as compensatory delayed operation in a case where eye behaviors are not sufficient for the movement of the viewpoint. Accordingly, it can be said that analyses of visual information search behaviors of eyes are the surest and most effective means that does not accompany delays, as means for detecting the alertness of the driver.

In the process according to the present disclosure, a visual problem that requires intelligent determination is presented to the driver, and an analysis of eye behaviors accompanying the understanding and handling of the problem is performed. With this process, the brain activity of the driver is detected actively, and the alertness of the driver is decided.

As mentioned before, the driver can be immersed in a nap, watching a live sports broadcast, or playing a game while the automobile is driving in an automated driving zone. However, for example, if the driver falls asleep in an automated driving zone, the alertness of the driver lowers. The driver needs to return to a high alertness state in which the driver can drive the vehicle normally consciously before entering a manual driving zone.

The system according to the present disclosure decides the alertness of the driver, notifies the driver that he/she needs to return to manual driving, and determines a control transfer start determination about the time when the driver who has received the notification actually starts steering by manipulation of steering equipment. The alertness of the driver is decided after that as well, and it is decided whether or not the driver has alertness sufficient for manual driving before the automobile enters the manual driving zone. That is, by the eye behavioral analysis of the driver, an evaluation of the brain perceptual cognitive activity of the driver is performed.

Note that, even during automated driving, the driver pays attention to whether automated driving is performed safely, in some cases. In such a situation, the driver is aware of the necessity for a return before notification of a manual-driving return request from the system, and voluntarily waits for the return to manual driving, in some cases. In order to analyze such a state also, the system according to the present disclosure allows an analysis of eye behavioral characteristics of the driver starting from the step of the state monitoring of the driver.

It is difficult to accurately grasp the consciousness level of the driver, that is, a return of alertness, on the basis of only a macroanalysis of blinks, facial expressions, and the like of the person.

In contrast, the system according to the present disclosure performs a detailed eye behavioral analysis which is a microanalysis performed in a time series. For example, a detailed eye behavioral analysis is performed in a process that the driver understands a problem by staring at it, and performs a determination by collating memory information and visual information taken in by staring at a target following the problem. At this time, a behavior such as a microsaccade performed for local position correction of the central visual field for checking details is observed. On the other hand, it is known that information input to neurons that control determinations in the brain includes diverse information, and the firing of a synapse for determination occurs in a case where the synaptic potential exceeds a certain threshold along with the input of the diverse information. That is, an activity that occurs in the alertness state in the brain starts from the accumulation of evidence information that is weak in each neuron even before a target is captured by the central visual field, followed by accumulation of additional information to be a clue for the determination proceeds in a corresponding neuron until immediately before the firing. Once the synaptic potential exceeds a certain value, the firing of the threshold of the determination occurs at the corresponding neuron, and this triggers the conveyance of the determination.

That is, information for making a determination is not necessarily a certain unique piece of information with high certainty, but information is input as information that is not well-grounded, and is less probable. If, as the sum total of the information, the synaptic potentials of neurons controlling determinations exceed a certain threshold, this appears as a determination, and the determination appears. Eye behaviors such as microsaccades or drifts that occur in the process of determining what a gazed target is are behaviors that appear for compensating information that is missing for a determination at that moment, and stimuli for the search behaviors become weak in a state in which the internal alertness in the brain is low, and their appearance remains unmanifested.

The process of staring to find an answer to a problem appears as a process like a saccade, a microsaccade, or a fixation of moving the central visual field to, or closer to, a target for acquisition of visual information, as part of a process of accomplishing an intelligent determination process in the brain like searching for details necessary for the determination or checking the accuracy of the answer. Note that the firing for a determination described above incorporates a determination of behavioral appearance like a microsaccade or a drift for searching for missing information, and is not limited to a determination as final intelligent understanding at the time point of completion of the understanding.

Eye behavioral analyses are means for indirectly observing part of the state of activity inside a brain when it cannot be observed directly, and are means for estimating the internal alertness in a brain with a focus on the fact that it can be used as a promising clue for alertness state decisions. When a visual problem is presented, the driver performs a process of moving his/her line of sight, that is, an eye behavior, in order to obtain the answer of the problem.

In a state in which the driver gazes at the space in the forward direction of a road at the time of driving of the vehicle, eye behaviors of the driver differ significantly depending on the situation of the space in the forward direction of the road. Noticeable behaviors do not appear in monotonous road zones and the like, and the internal alertness state of the driver cannot necessarily be grasped by a simple passive line-of-sight behavior analysis. In contrast, in the process according to the present disclosure, a problem to be stared at actively is presented to the driver, and an analysis of a line-of-sight behavior that is expected to appear in a case where the internal alertness of the driver is high is performed. As a result, the state of a return to the alertness of the driver can be decided highly precisely.

Because this is somewhat difficult to understand, it is explained by using one example.

In a problem supposed here, plural animal silhouettes whose features are not so clear are presented.

In the problem presented, plural silhouettes (patterns) are presented simultaneously, and the driver is asked to select one pattern with a different feature from them.

For example, two or more predatory animals are arranged randomly, and further only one silhouette of a livestock animal like a cow, a sheep, or a pig is arranged.

For such a visual problem, the driver needs to quickly find a pattern that is likely to have a different feature, and check what are the differences between the pattern and other figures arranged around it, and also simultaneously whether there is another pattern with a similar feature. Accordingly, the driver performs a process of sequentially inspecting individual silhouettes in order to analyze the features of the patterns. With the movement of the line of sight, local features of detailed specific portions of a pattern at the central visual field of the line of sight are taken into the brain.

How many additional features need to be acquired, from directing the central visual field to a certain pattern or an event to completing the understanding and determination about the pattern or the event, varies depending on the ability to refer to memories of a person, the determination ability, and the like.

Accordingly, an observation behavior lasts longer in some cases, and is completed in a short period of time in some other cases. For a simple problem asking the driver to decide differences between colors, a problem asking the driver to select one from two things with clear differences, and the like, determinations are completed simply by capturing the features in the peripheral visual field, and a local search behavior of eyes does not appear in some cases. Accordingly, such problems are not suited as problems to be used for decisions of the state of the brain activity of the driver.

In the case of the problem described above asking the driver to select one with a different feature from plural animal silhouettes, a determination process for visual information and a memory referring process proceed simultaneously in parallel. Accordingly, such a problem is optimum for a process of evaluating the brain perceptual cognitive activity of the driver.

The technology forming the basis of the present disclosure resides in an analysis of behaviors of the driver, specifically, eye behaviors, that occur accompanying thinking determinations for solving a presented problem.

Note that problem output means to present problems that can be used include various means such as, for example, an instrument panel at the driver's seat, a HUD (head-up display), a portable terminal, or sound-merged presentation. Because behaviors of the driver vary depending on which of these is used, driver-specific characteristics are acquired in advance as training data corresponding to each output means, and a final alertness decision is performed by referring to the training data, in a preferred configuration.

It should be noted, however, that if the same problems are repeated, there is a possibility that reflexive operation not accompanying thinking, that is, reflexive operation not requiring activities that control determinations in the brain, occurs. Accordingly, a different one of problems is presented on each occasion, and the presentation of problems whose answers can be found by simple predictions should be avoided.

The visual field of a human is classified into two which are a peripheral visual field having low resolution, but being extremely sensitive to dynamic changes, and a central visual field with a small area that can acquire detail information with high resolution which becomes an important factor for determinations.

The central visual field is mainly used for observation of important information, and a process is performed about the observed information by referring to fractional memories and comprehensive memories.

In a natural environment, one directs his/her line of sight upon receiving a stimulus from a motion of an animal or the like that can be an enemy or game moving in the peripheral visual field of a sight. At that time, in many cases, an eye behavior called a saccade (eye rotation) appears. Then, visual acquisition of information at higher resolution requires acquisition of information at the central visual field of eyes. The detail information is captured by the central visual field which has a viewing angle of several degrees.

In a case where simple determinations based on memories are not possible as in the case described above of a determination-requiring visual problem asking the driver to select one with a different feature from plural animal silhouettes, a line-of-sight behavior to capture information necessary for performing a sure determination is expected, and the possibility that a certain behavior such as a fixation or a microsaccade (eye microrotation) of eyes mentioned before is observed increases.

Note that, in a case where a process of estimating the alertness states of drivers is performed on the basis of eye behaviors, not all the drivers necessarily exhibit the same behavior. That is, each driver has a different action experience, and even if they see an identical object, processes until reaching the understanding are different. There are some people who complete determinations at a step when they captured the contour of the object within their peripheral visual fields, and there are some other people who capture the target within their central visual fields, but cannot reach determinations even by looking at details of it in some cases. In a preferred configuration, similar processes are not performed for all users, but rather processes are performed on the basis of driver-specific training dictionary data. This is because there is a possibility that drivers having abundant driving experiences, drivers who drive automobiles as their jobs such as taxi drivers, and competitive race drivers have different alertness states as compared to those of inexperienced drivers even if they exhibited the same eye behaviors.

Accordingly, a training dictionary generated by a training process for each driver is used to perform an alertness decision, preferably.

Note that, in a possible system, answers to problems presented to the driver are detected by the pressing of a physical button, for example. However, button manipulation and the like accompany cumbersomeness.

The process according to the present disclosure does not request manipulation by the driver such as button manipulation described above. It only analyzes eye behaviors of the driver by sensors, and burdens on the driver of inputting answers do not occur.

The driver moves his/her line of sight to an information display area on which a problem is presented, perceives information, and performs collation with intelligent cognition, that is, memories. However, the cognition work is not completed by the driver only by directing his/her eyes such that the visual information reaches his/her retinas, and requires understanding and completion based on memories necessary for a determination.

In the course of these processes, a certain behavior such as a fixation or a microsaccade (eye microrotation) of eyes mentioned before is observed due to the necessity for capturing missing information or capturing temporal changes of the retinas.

For example, in a case where the process of performing problem presentation, to the driver, accompanying notification for a return to manual driving is repeated, the driver memorizes that this is a process of alertness cognition by the system. As a result, it is difficult with a simple problem such as selection of a color to determine whether or not sufficient target-grasping work has been started in the brain simply from the fact that the driver has directed his/her line of sight to a target.

In contrast, in a case of a determination-requiring visual problem like the one mentioned before asking the driver to select one with a different feature from plural animal silhouettes, information necessary for a determination cannot necessarily be acquired satisfactorily only by directing the central visual field of the eyes to a problem target, and it becomes necessary to additionally obtain information.

As visual behavioral characteristics of humans, in a case where a person directs his/her line of sight to a target to see the target, in the process of generally directing the central visual field of the line of sight by a saccade, understanding the target that is seen, and completing a determination, a feature-capturing behavior like a microsaccade (eye microrotation) or a fixation is exhibited in order to further capture missing information necessary for the determination.

Note that, as mentioned before, in a case where a behavioral analysis of the driver is performed through an eye behavioral analysis, it is preferable to use a classifier that is obtained by training with an analysis of driver-specific behavioral characteristics.

In the process according to the present disclosure, the presentation of visual information is performed, and an eye behavior that is exhibited when a person checks the visual information is analyzed. When the visual information is presented, and the driver stares at the problem without excessive operation of his/her consciousness, eye behaviors of the driver for a search for the answer occur, and the search behavior is analyzed directly. That is, the driver visually looks at the problem, and without performing separate work of an utterance of the answer or manipulation of a button, the state of the thinking activity can be analyzed from the behavior observation of the line of sight.

The driver starts staring at the problem by using his/her line of sight, and it becomes possible to estimate the alertness level by analyzing the eye behavior in the situation while the driver is proceeding with the understanding. In such a manner, the process according to the present disclosure makes it possible to decide the state of the thinking activity, that is, the alertness of the driver, from the behavior observation of the line of sight without accompanying the cumbersomeness that results from button manipulation or the like.

For example, at the time when notification of transfer to manual driving is displayed on the display section in the middle of transition from automated driving to a return to manual driving, a problem is displayed on the display section.

The problem is displayed on the display section (interface) such as a console panel or a HUD on which the driver can stare at the problem, and eye behaviors of the driver are analyzed. This process enables the alertness decision of the driver in a short period of time.

Examples of problems that can be used include a wide variety of problems such as, for example, a problem asking the driver to find a particular insect with a bush in the background, a problem asking the driver to look for a bird hiding itself in a thick forest, or a problem asking the driver to look for a four-leaf clover in a patch of grass.

Note that it is not necessarily essential to obtain the correct answer for a problem for the purpose of deciding the alertness or its alertness level. Even in a case where an answer is incorrect, there is a possibility that some answer or a reaction of the driver of operation of stepping on a pedal or the like is detected. The process of deciding the alertness of the driver may be performed on the basis of such a reaction. Note that, in a case where the alertness is very high, in order to proceed with the observation for understanding of a portion where there is likely to be a change in presentation information, fixation or microsaccade operation appears intermittently after the line of sight is directed to an image group to be a target. In a case where such observation behavior information is obtained, it can be decided from a behavior-specific analysis that the alertness of the driver is high.

The appearance of this search behavior does not appear if the answer of a visual problem is the color of a lamp, a simple numerical value, or the like because the answer can already be predicted at the moment when a clue is captured at the contour of the peripheral visual field, and the answer can be known even without looking at individual lamps or numerical values within the central visual field. In addition, even in a case of problems that are somewhat complicated, the repetition of identical problems and features with too strong impression remain strongly in the memory. By performing the problem presentation randomly by presenting various problems like the ones explained in the following Item 5, or by eliminating the repetition of identical problems by regularly updating problems remotely, the deterioration of the appearance of search behaviors can be avoided.

[4. About Execution Configuration of Alertness Deciding Process in Information Processing Apparatus]

Next, a configuration for executing the alertness deciding process by the moving apparatus and the information processing apparatus according to the present disclosure is explained.

The moving apparatus according to the present disclosure or the information processing apparatus that can be mounted on the moving apparatus performs a process of deciding the alertness of the driver in a short period of time without generating significant burdens on the driver.

The process of deciding the alertness of the driver is executed at the driver-information acquiring section 12 and the data processing section 11 of the automobile 10 depicted in the FIG. 1.

An example of the specific configuration that executes the process of deciding the alertness of the driver is explained with reference to FIG. 6.

Figure 6:
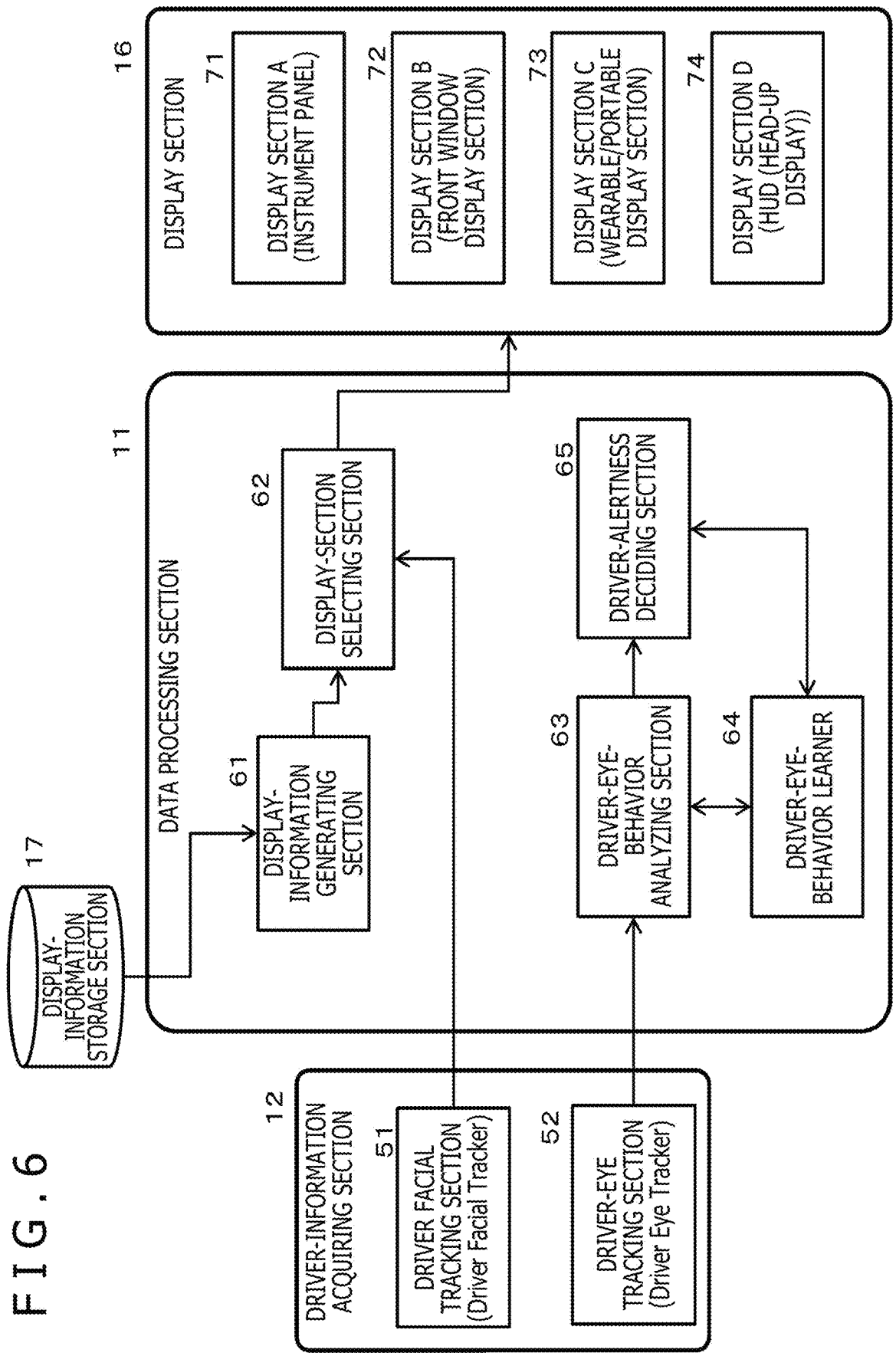
FIG. 6 is a figure for explaining a configuration example of an information processing apparatus mounted on the moving apparatus according to the present disclosure.

FIG. 6 depicts the data processing section 11, the driver-information acquiring section 12, a display section 16, and a display-information storage section 17.

Note that FIG. 6 is a figure depicting a partial configuration of the information processing apparatus mounted on the moving apparatus according to the present disclosure. That is, FIG. 6 is a block diagram depicting selected constituent elements that are applied to the process according to the present disclosure explained below, that is, the alertness decision of the driver.

The driver-information acquiring section 12 has a configuration explained with reference to FIG. 4 before, and only the following two configurations are depicted in FIG. 6.

Those are the driver facial tracking section (Driver Facial Tracker) 51 and the driver-eye tracking section (Driver Eye Tracker) 52.

These include a camera, a facial detection sensor, an eye-position detection sensor, and the like, for example.

Motion information of the face and head of the driver detected by the driver facial tracking section (Driver Facial Tracker) 51 is input to a display-section selecting section 62 of the data processing section 11.

Motion information of the eyes of the driver detected by the driver-eye tracking section (Driver Eye Tracker) 52 is input to a driver-eye-behavior analyzing section 63 of the data processing section 11.

Although these configurations, the driver facial tracking section 51, the eye tracking section 52, and the data processing section 63 in the configurations depicted in FIG. 6 are individually depicted as separate configurations, some or all of their functionalities may be integrated in and taken into an image sensor element to form a monolithic configuration. Arranging processes that require processes at particularly high speeds on the back of or near the image sensor contributes to suppression of the placement of fast signal wires, and suppression of noise generation.

The data processing section 11 has a display-information generating section 61, the display-section selecting section 62, the driver-eye-behavior analyzing section 63, a driver-eye-behavior learner 64, and a driver-alertness deciding section 65.

The display-information generating section 61 generates a problem to be displayed on the display section 16. Specifically, the display-information generating section 61 generates a problem such as the problem explained above asking the driver to select one pattern with a different feature from plural animal silhouettes. The display-information storage section 17 stores therein data that can be used for generating various problems.

Note that specific examples of the problems are explained later.

The display-section selecting section 62 selects a display section on which the problem generated by the display-information generating section 61 is to be displayed.

As depicted in the figure, the display section 16 includes various forms of display sections such as a display section A (instrument panel) 71, a display section B (front window display section) 72, a display section C (wearable/portable display section) 73, or a display section D (HUD (head-up display)) 74.

On the basis of motion information of the face and head of the driver detected by the driver facial tracking section (Driver Facial Tracker) 51, the display-section selecting section 62 selects a display section ahead of the line of sight of the driver as a display section on which the problem generated by the display-information generating section 61 is to be displayed, and causes the selected display section to display the problem.

The driver-eye-behavior analyzing section 63 receives, as an input, the motion information of the eyes of the driver detected by the driver-eye tracking section (Driver Eye Tracker) 52, and analyzes the motion of the eyes of the driver.

When the problem generated by the display-information generating section 61 is displayed on the display section 16, the driver moves his/her line of sight to the problem in order to acquire the answer of the problem. For example, as mentioned before, a determination-requiring visual problem like the problem asking the driver to select one with a different feature from plural animal silhouettes is displayed on the display section 16. In order to acquire the answer of the problem, the driver performs eye behaviors for additionally acquiring necessary information. For example, the driver performs eye behaviors such as a saccade (eye rotation), a fixation, or a microsaccade (eye microrotation) of eyes.

The driver-eye-behavior analyzing section 63 analyzes the eye behaviors of the driver.

The eye behavior information obtained through the analysis by the driver-eye-behavior analyzing section 63 is input to the driver-alertness deciding section 65.

On the basis of the eye behavior information obtained through the analysis by the driver-eye-behavior analyzing section 63, the driver-alertness deciding section 65 decides the alertness of the driver.

In a case where it is confirmed that the driver is executing eye behaviors such as a saccade (eye rotation), a fixation, or a microsaccade (eye microrotation) of eyes for problem solving, the driver-alertness deciding section 65 decides that the alertness of the driver is high. On the other hand, in a case where these eye behaviors are not observed or in a case where these eye behaviors are not observed sufficiently, the driver-alertness deciding section 65 decides that the alertness of the driver is low.

A specific example of eye behaviors analyzed by the driver-eye-behavior analyzing section 63 is explained with reference to FIG. 7.

Eye behavioral analyses are effective means for checking returns to consciousness of drivers. Note that it has conventionally been known that a line of sight can be analyzed by analyzing the direction toward which the line of sight is directed, for example. By making this technology advanced further and performing an analysis of a line-of-sight behavior at a high speed, more detailed behavior detection of eyes becomes possible.

While there are some behaviors that appear as reflexive behaviors of living forms in a detailed eye behavioral analysis, the behaviors simultaneously exhibit many phenomena that appear reflecting neurotransmission and processes in the brain. Accordingly, results of activity such as the cognition of the brain are reflected, and become apparent forms.

By using the fact that eye behaviors reflect the activity in the brain, it becomes possible to estimate the alertness level of the driver highly precisely.

Much of outside world information that a human acquires in a case where he/she performs a situation determination necessary for action is obtained from visual information. When a human perceives visual information, recognizes the visual information, and makes action, the human directs his/her line of sight to the information, and performs a comparative reference of the information and his/her memories (recorded knowledge). It has been known that until a human understands the information ahead of his/her line of sight, he/she exhibits a particular eye behavior necessary for visual information cognition like a micro fixation, a microsaccade, a tremor, or a drift while keeping directing his/her line of sight toward a portion where the information can be seen, or toward the vicinity of the portion.

The eye behavior varies depending on whether the human is in a normal alertness state or is in a low-consciousness/alertness state.

Figure 7:
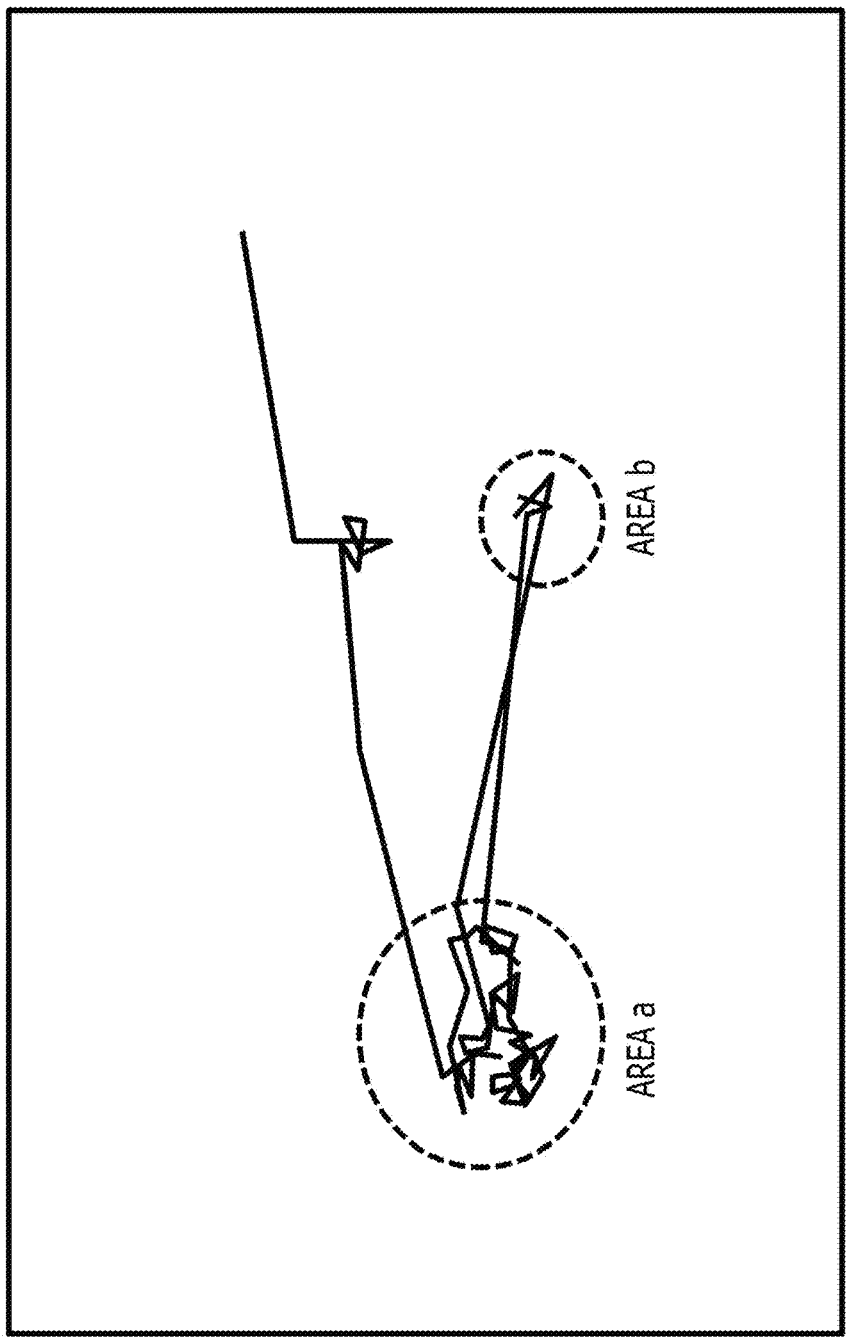
FIG. 7 is a figure for explaining one example of the locus of eye behaviors of a driver at the time when a visual problem asking the driver to look at a certain piece of information is presented.

FIG. 7 depicts one example of the locus of eye behaviors of the driver when a visual problem asking the driver to look at a certain piece of information is presented.

In the example depicted in FIG. 7, the locus of eye behaviors when the person first gazes at portions near an area a, and thereafter gazes at portions near an area b is depicted.

In a case where a human attempts to stare at a certain piece of information (problem) and understand the contents, the human performs an eye rotation called a saccade which is large like the behavior locus depicted in FIG. 7. The human directs his/her eyes to a predetermined stared portion and performs eye behaviors that accompany a fixation near the predetermined visual portion and a microsaccade which is micro eye rotation operation for a local area.

As explained above, when a human acquires necessary information from visual information consciously, and performs a necessary determination, a characteristic eye behavior appears in order to obtain information. On the other hand, if the human has lowered consciousness and the visual information search is insufficient, an eye behavior necessary for a fixation of determining and acquiring information is disturbed. FIG. 8 depicts figures for explaining examples of the locus of eye behaviors of a driver when a visual problem asking the driver to look at information is presented, and for explaining a difference between behaviors in cases of different alertness states. FIG. 8($a$) is a figure depicting a problem.

Problem=COUNT SMALL ANIMAL(S)

This is the problem.

The order of the movement of the line of sight varies depending on a person who looks at the problem. There are various subjects. Some subjects direct their lines of sight first toward the question text "Q," which is the problem, some subjects look at answers "Ans," then look at the question text "Q," and then look at the entire drawing of an array, and some subjects glance at information of answer silhouettes, and then look at the problem. What is important for the evaluation of the activity in the brain is evaluation as to whether the driver who is a subject at the time of the evaluation is exhibiting a behavior of starting execution of a search/fixation necessary for performing acquisition and a check of information necessary for an answer at the moment.

An explanation is given using observation data depicted in FIGS. 8($b$) and ($c$) as an example. (b) depicts an eye behavior that is exhibited when the driver responds to a problem in a high-alertness state. On the other hand, (c) depicts an example of the locus of eye behaviors that are exhibited when the driver has a lowered visual-problem-handling ability. (c) depicts one example in which, although the eyes of the driver are open, the driver is not alert enough to handle the problem in this state, and, because of this, in a visual information search including a saccade of the eyes, the eye behavior noticeably exhibits the tendency of what is called shifting eyes.

Because this is influenced by the tendency belonging to individuals such as the influence of a squint or a dominant eye which is behavioral characteristics or a change of the sight that accompanies the physical condition on that day, it is desirable that identification of a state taking into consideration characteristics of an individual is performed for the alertness decision, and it is better to perform a decision by taking into consideration characteristics of each individual after identifying who the driver is.

For example, in order to check whether or not the driver remains conscious during automated driving, regular monitoring needs to be performed. For the purpose of performing monitoring without excessively bothering the driver, the system presents a symbol that requires thinking determination to the driver, and observes eye behaviors, for example. In a case where, as a result of the observation, it is observed that the driver is currently capable of thinking checking operation by using his/her line of sight, it is surmised that the driver has prioritized the thinking activity in the brain for execution of the problem handling, and is no longer remained immersed in another secondary task.

In addition, the system may perform a process of determining cognition completion by detecting that the line of sight of the driver is directed toward presentation information, and further performing cognition of the detection by staring.

Note that the alertness deciding process based on the eye behavior preferably uses driver-specific training data. The training data is generated by the driver-eye-behavior learner 64. Alternatively, it may be generated by an external server, in another possible configuration.

The driver-eye-behavior learner 64 receives, as an input, the eye behavior information obtained through the analysis by the driver-eye-behavior analyzing section 63, receives, as an input, the alertness information of the driver decided by the driver-alertness deciding section 65 on the basis of the eye behavior information, and further receives, as an input, driving steering information of the driver also.

On the basis of the input information, the driver-eye-behavior learner 64 learns correct correspondences between eye behaviors of the driver and levels of the alertness of the driver at the time when those eye behaviors are exhibited, and stores the correspondences in the storage section as training data. These processes may be executed by an external server, in another possible configuration.

In addition, the driver-eye-behavior learner may perform interlocked learning of correlations with driver vital signals obtained by another vital sensor mentioned below, and input influential factors such as a use time period during day, to perform situation-adapted decisions, thereby attempting to increase the precision of the decisions.

The driver-alertness deciding section 65 receives, as an input, the eye behavior information obtained through the analysis by the driver-eye-behavior analyzing section 63, and uses the input information and the training data generated by the driver-eye-behavior learner 64 to execute a more precise alertness decision.

Note that, in a case where there is no training data or in a case where there is not a sufficient amount of training data, the alertness decision may be performed by using data of correspondences between typical eye behaviors and alertness (average data of humans) without using training data, in another possible configuration.

Note that, as mentioned before, the driver-eye-behavior analyzing section 63 acquires eye behaviors such as a saccade (eye rotation), a fixation, or a microsaccade (eye microrotation) of eyes which is an eye behavior for problem solving by the driver. The driver-eye-behavior learner 64 repetitively receives, as inputs, behavioral characteristics according to the driver alertness of the driver, and executes cumulative learning, to construct a dictionary for performing alertness decisions from eye behaviors. The dictionary is used for estimating the alertness state of a user at the time of observation from newly-observed eye behavioral characteristics.

[5. About Specific Examples of Problems Presented to Driver for Deciding Alertness of Driver]

Next, specific examples of problems presented to the driver for deciding alertness of the driver are explained.

As mentioned above, the information processing apparatus mounted on the moving apparatus according to the present disclosure presents a predetermined problem to the driver during the execution of automated driving, analyzes eye behaviors of the driver as a response to the problem, and decides the alertness of the driver on the basis of the eye behaviors, for example.

For example, at a step before entering a manual driving zone from an automated driving zone, the problem is presented to the driver, eye behaviors of the driver as a response to the problem are analyzed, and the alertness of the driver is decided.

When the actual steering by the steering wheel or brake is resumed according to the procedure for a return to manual driving by the driver, it should always accompany a cognition determination from visual information. That is, a return to the alertness of the brain is an essential requirement in the procedure for manual driving. The driver looks at an object, and uses visually obtained information to acquire information necessary for manipulation.

Accordingly, if a perceptive determination activity in the brain necessary for manipulation can be analyzed, it is possible to decide whether or not the driver has a determination ability sufficient for manual driving, that is, whether or not the driver is in a high-alertness state.

The information processing apparatus according to the present disclosure presents a visual problem to the driver before a return to manual driving, and analyzes eye behaviors of the driver that occur at the time of solving the problem. Further, the alertness of the driver is evaluated on the basis of the eye behavior observation result.

Visual problems that are presented to the driver in the configuration according to the present disclosure are problems that make it necessary for the driver to perform work of additionally searching for missing information required to solve the visual problems.

If such a process of additionally searching for missing information is performed, eye behaviors such as a fixation or a microsaccade (eye microrotation) of eyes occur.

As explained with reference to FIG. 6 and FIG. 7 before, the driver-eye-behavior analyzing section 63 receives, as an input, the motion information of the eyes of the driver detected by the driver-eye tracking section (Driver Eye Tracker) 52, and performs an eye behavioral analysis of the driver.

The driver-eye-behavior analyzing section 63 performs an analysis as to whether or not, as eye behaviors of the driver, eye behaviors such as a saccade (eye rotation), a fixation, or a microsaccade (eye microrotation) of eyes are being observed.

The eye behavior information obtained through the analysis by the driver-eye-behavior analyzing section 63 is input to the driver-alertness deciding section 65, and, on the basis of the eye behavior information obtained through the analysis by the driver-eye-behavior analyzing section 63, the driver-alertness deciding section 65 decides the alertness of the driver.

In a case where it is confirmed that the driver is executing eye behaviors such as a saccade (eye rotation), a fixation, or a microsaccade (eye microrotation) of eyes for problem solving, the driver-alertness deciding section 65 decides that the alertness of the driver is high. On the other hand, in a case where these eye behaviors are not observed or in a case where these eye behaviors are not observed sufficiently, the driver-alertness deciding section 65 decides that the alertness of the driver is low.

In the following, specific examples of problems to be presented to the driver by being generated by the display-information generating section 61 of the data processing section 11 of the information processing apparatus according to the present disclosure, or by being selected and acquired from the display-information storage section 17 are explained.

Figure 9:
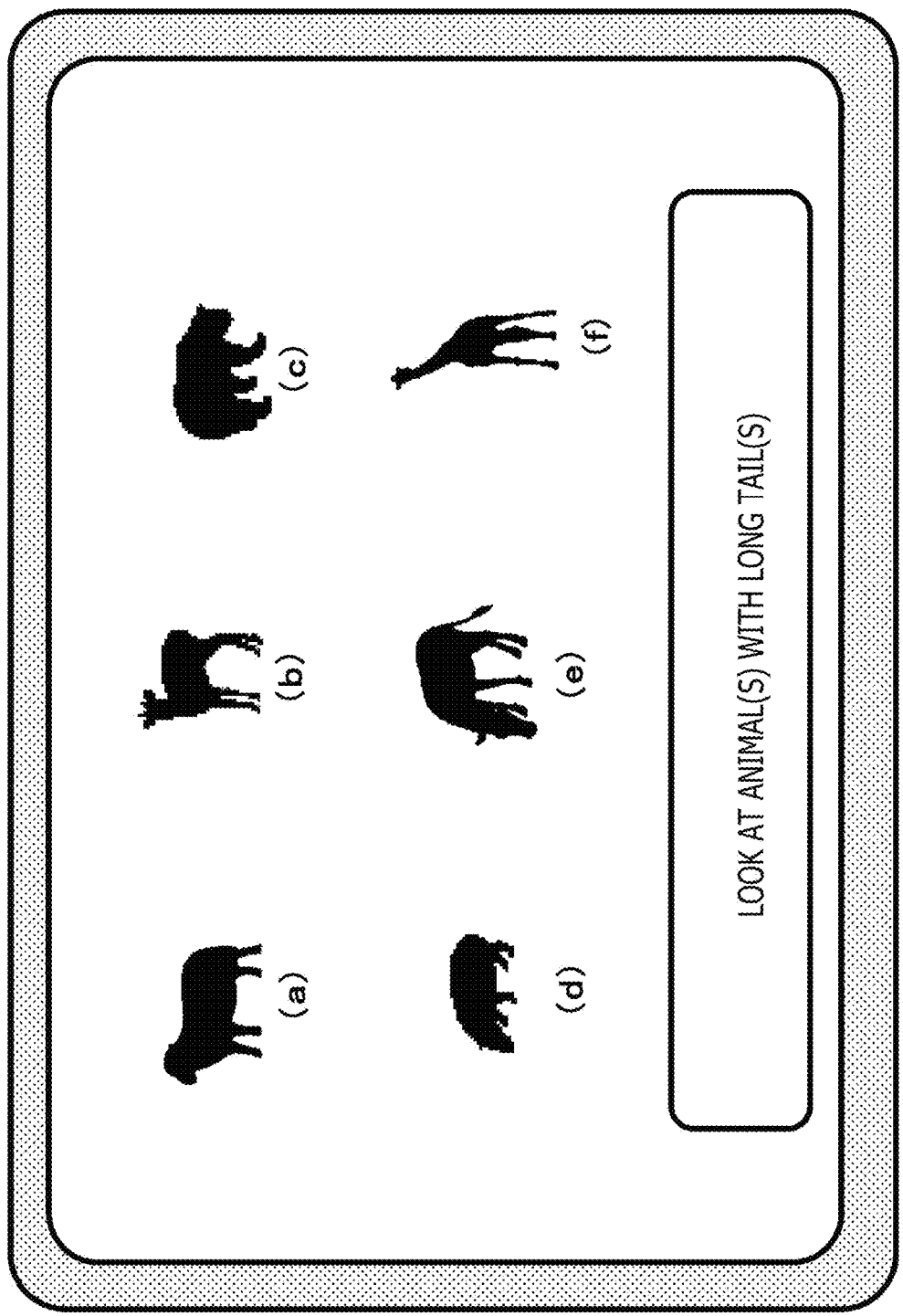
FIG. 9 is a figure for explaining one example of problems to be displayed.

FIG. 9 is a figure depicting one example of problems. In the example depicted in FIG. 9, plural animal silhouettes are displayed side by side, and a problem "LOOK AT ANIMAL(S) WITH LONG TAIL(S)" is presented as a problem sentence.

Six types of silhouette,
(a) sheep,
(b) deer,
(c) bear,
(d) pig,
(e) horse, and
(f) giraffe
are displayed as animal silhouettes.

In a case where the problem "LOOK AT ANIMAL(S) WITH LONG TAIL(S)," which is the problem sentence, is presented, if it is supposed that the alertness of the driver is sufficiently high, it is predicted that the driver performs eye behaviors following the steps (S1 to S3) below for problem solving.

(S1) Saccade (eye rotation) of directing the line of sight of the eyes toward the problem display section for checking the problem, and a fixation of reading in the problem (S2) Behavior of looking over each silhouette (a process of glancing at the whole of the silhouettes that are displayed side by side, which is a line-of-sight movement process of looking over the whole without paying attention to particular silhouettes)

(S3) Process of performing a saccade (eye rotation) of directing the line of sight to a particular silhouette which is a target of the correct answer, and a fixation for analyzing the particular silhouette and checking feature portions like the tail and head of the particular silhouette Further, in a case where operation to check whether there is overlooked information appears, there is a possibility that, as Step (S4), the driver generates an eye behavior of fixating his/her eyes also on other targets that are thought to be incorrect answers.

In particular, in a case where the number of the correct answers of the problem presentation is not one, but larger than one, there is a high possibility that fixations on many silhouettes occur in order to perform the process of checking whether there is overlooked information.

When the driver finishes directing his/her line of sight to all the silhouettes, it may be decided that the problem is ended, and the next problem may be presented.

In this case, as Step (S5), it is predicted that the line of sight of the driver saccade-moves onto the next problem presentation portion.

It is expected that the driver performs the eye behaviors of Steps (S1) to (S5) described above, for example. It should be noted, however, that these are behaviors that are observed in a case where the alertness of the driver is sufficiently high, and the driver has the will to solve the problem.

For a search for information necessary for the problem solving, that is, for an additional search for additionally obtaining missing information, the driver directs his/her viewpoint to particular image display areas, performs fixations, acquires visual information necessary for a determination, and performs a process of collating the acquisition information and memories. Further, the driver generates behaviors such as a microsaccade (eye microrotation) or a fixation micromovement for searches for additional and peripheral features for compensation for the completion of the understanding.

In a case where such behaviors are observed, it is represented that the driver is attempting to solve the problem, and it can be determined that the alertness of the driver is sufficiently high.

In a case where the driver is attempting to solve the problem by taking in visual information having physically and optically reached at the retinas into the brain, and executing collation with memories, for example, the driver generates the sequential behaviors of Steps (S1) to (S3) described above. On the other hand, in a case where the driver performs only a behavior of directing the line of sight to a feature portion simply reflexively, the sequential behaviors of Steps (S1) to (S3) described above are not observed at all, or a state occurs where only Step (S1) described above, only (S2) described above, or only (S3) described above is observed.

The thus-observed eye behaviors of the driver are obviously different between the state in which the alertness of the driver is high, that is, the state in which the driver has the will to solve the problem, and the state in which the alertness of the driver is low, that is, the state in which the driver does not have the will to solve the problem, or the will is weak.

The information processing apparatus according to the present disclosure mounted on the moving apparatus presents a visual problem like the one depicted in FIG. 9 to the driver, analyzes eye behaviors of the driver after the presentation, and decides whether or not the driver is performing eye behaviors for solving the problem (e.g., Steps (S1) to (S3) described above). If the driver is performing the eye behaviors, it is decided that the alertness is high, and if the driver is not performing the eye behaviors, it is decided that the alertness is low.

What is important in a case where the determination of the alertness state of the driver is performed is whether or not the driver can refer to memories necessary for situation determinations executed in the brain of the driver, and can perform action planning as a result thereof, to determine the state of a return of related intelligence portions.

Among them, the action planning as well as neurotransmission and a muscular return for moving the body necessary for steering as actual driving manipulation cannot be observed only through eye behavioral analyses. However, the acquisition of visual information necessary for determinations requires a visual check that accompanies eye behaviors.

For example, in order to visually grasp the situation of dangers and grasp the surrounding situation for avoiding dangers, for example, grasp obstacles on the road, dangerous objects such as oncoming automobiles or hills, the direction or space into which the automobile can move because there are no obstacles, or the like, eye behaviors for visually checking them are required.

Although it is difficult to completely check the entire alertness of the brain only by analyses of eye behaviors, for example, it is possible to determine whether or not the brain is in a state in which brain activities necessary for action planning, which is essential for manual driving, are possible, and the alertness decision by the eye behavioral analysis of the driver based on problem presentation according to the present disclosure can be said to provide a sufficient advantage for deciding whether or not the driver is alert enough for manual driving.

It should be noted, however, that it is not possible to ascertain that the manual-driving return ability of the driver determined only from eye behaviors completely reflects action determinations, neurotransmission, and a muscular return of the driver. Accordingly, the system (information processing apparatus) provided on the moving apparatus also performs evaluation of steering action after the driver started manual driving. In addition, actions that are performed since the notification timing of a manual-driving return request to the driver before the driver is seated on the driver's seat until the driver is seated on the driver's seat and returns to the driving posture are also evaluated. The system (information processing apparatus) provided on the moving apparatus uses the evaluation information to generate training data used for decisions about the alertness of the driver based on eye behaviors, for example. Note that the training data is preferably generated as driver-specific training data.

Note that the driver receives notification of a request for a return to manual driving in a state in which the driver is seated on the driver's seat, that is, in a state in which the driver is in the driving return posture, in some cases. In this case, actions for returning to manual driving such as an action of returning to the driver's seat do not occur almost at all. The decision about the alertness of the driver in such a case does not have many steps in which returning actions of the driver can be observed, target actions by which evaluation can be performed are limited, and information from the analysis of eye behaviors is one of few observation targets by which the alertness state of the driver can be directly observed.

From the eye behavioral analysis, the internal alertness state of the driver is estimated, and if it is determined that the alertness of the driver in the brain is high and it is decided that a condition necessary for starting a return to manual driving is satisfied, the driver is allowed to start manual driving.

After the start of manual driving, while a transfer from automated driving to manual driving is being completed, monitoring of the steering of the driver is performed at the process of gradually entrusting the driver with the steering of driving equipment which has been entrusted to the system. In a case where it is decided that the torque that the driver applies to the steering wheel or the steering force that the driver applies to steering equipment is not appropriate, or in a case where a state in which steering cannot be confirmed or another similar state is confirmed, the system (information processing apparatus) decides that the manual-driving return ability of the driver is insufficient, and performs a measure such as emergency deceleration, slowing down, pulling over, evacuating, or stopping.

Note that the evaluation of the manual-driving return quality after the driver has started manual driving is performed not only from behaviors of the eyes, but also on the basis of various processes like the ones mentioned below.

(1) Evaluation of the state by monitoring at the steady state (2) Evaluation as to whether or not there is a response to a return notification, and evaluation of the accuracy of dynamic actions such as pointing and calling (3) Evaluation of the response quality (4) Evaluation of the transition of the return posture (5) Evaluation of the seating transition, and the seated posture (6) PERCLOS (proportion of the openings of eyes) evaluation (7) Internal alertness evaluation by the eye behavioral analysis according to the present disclosure (8) Evaluation of the appropriateness of the steering of a steering apparatus and the like (9) Evaluation of the appropriateness of steering noise correction Along with the alertness evaluation based on eye behaviors, the various evaluation processes described above are also performed to evaluate the quality of a return of the driver to manual driving.

In such a manner, the information processing apparatus according to the present disclosure not only decides the alertness state at a step of the cognition of the brain activity of the driver, but also executes the evaluation of the manual-driving return quality after the subsequent start of manual driving.

Note that, in a case where a problem that causes the appearance of line-of-sight behaviors is presented to the driver, if patterns with the same silhouettes are displayed repetitively or problems are monotonous, and patterns with obvious differences are used, the driver reaches a determination by using information that is obtained by capturing the problems in his/her peripheral visual field, and it becomes possible to derive answers simply without checking details. In such a case, the driver finishes the work by answering without generating eye behaviors for the purpose of checking details.

A specific example in which problems are monotonous and patterns with obvious differences are used is explained with reference to FIG. 10.

Figure 10:
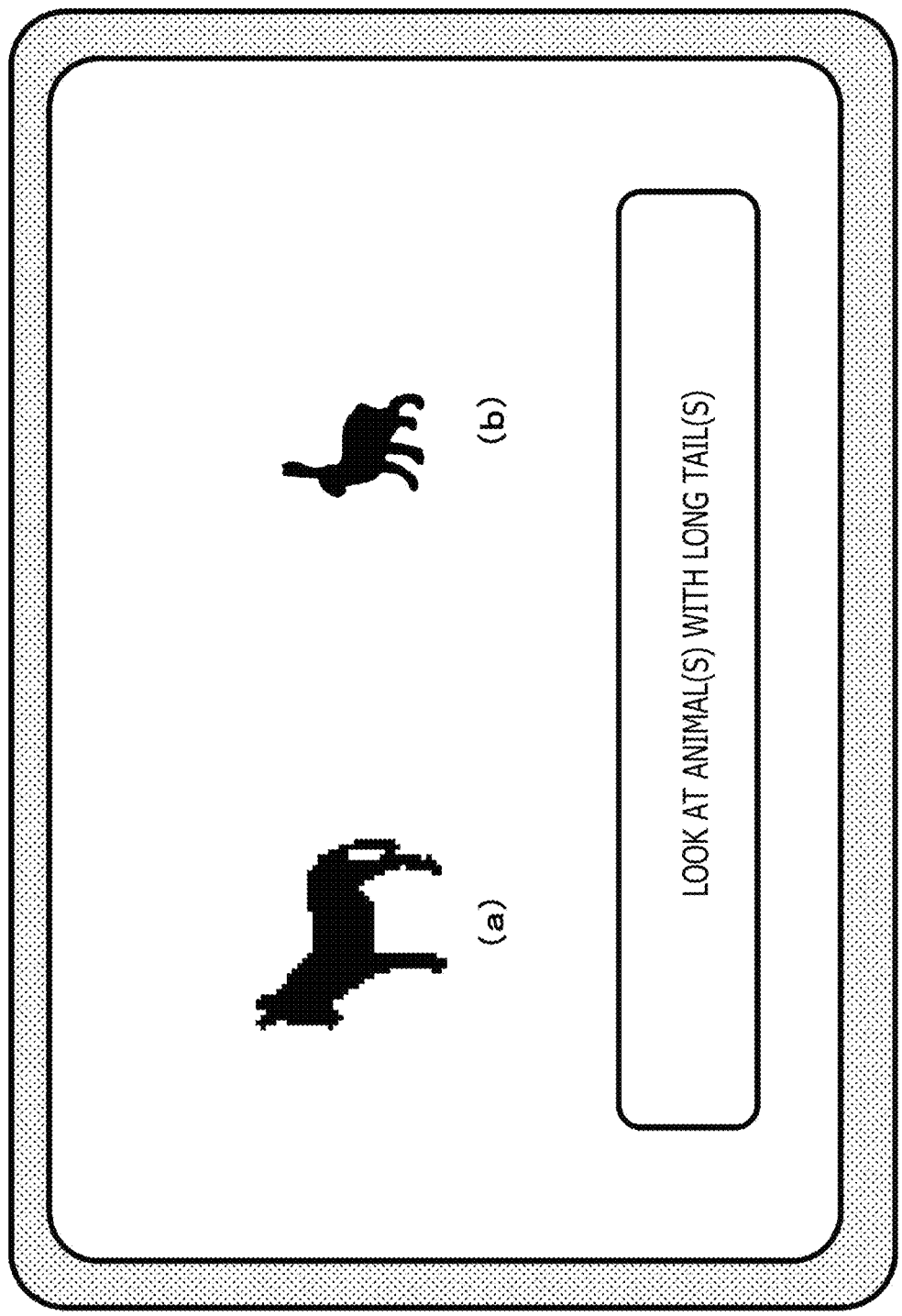
FIG. 10 is a figure for explaining one example of problems to be displayed.

In the example depicted in FIG. 10, two animal silhouettes are displayed side by side, and a problem "LOOK AT ANIMAL(S) WITH LONG TAIL(S)" is presented as a problem sentence.

Two types of animal silhouette, (a) horse, and (b) rabbit are displayed as animal silhouettes.

(a) The pattern of the horse is a pattern in which its tail is drawn clearly.

In a case where the problem "LOOK AT ANIMAL(S) WITH LONG TAIL(S)," which is the problem sentence, is presented, almost all respondents can immediately determine which animal in the patterns has a long tail without directing the line of sight and gazing hard and carefully at details of the tail of the horse and the pattern of the rabbit.

In a case where it is the first time to see the problem, the driver might look at the problem in detail, but this is done so not because it is necessary for determining the answer. Rather, this is merely an eye behavior performed out of interest as to what type of patterns are used for the problem presentation. Such an eye behavior out of interest eventually results in a determination that can be performed already at a step of capturing a target within the peripheral visual field without capturing it within the central visual field after the same patterns of the same animals are displayed in the same arrangement repeatedly. Accordingly, the possibility that an eye behavior that characterizes a fixation such as a microsaccade (eye microrotation) that is expected as operation for checking detail features is observed lowers. If such a situation occurs, it becomes difficult to decide the alertness of the driver in the brain on the basis of eye behaviors.

For the purpose of deciding the alertness state of the driver by using eye behavioral analyses, always fresh problems are presented preferably. For example, part of driving landscapes that change from moment to moment may be used for problems, in one possible configuration.

In a situation where the automobile is driving through an urban district or the like full of various landscapes and there are a large number of targets to which the driver moves his/her line of sight when he/she is performing manual driving, for example, an analysis of eye behaviors of the driver to a map (saliency map) corresponding to a landscape in the driving direction toward which the line of sight of the driver is directed may be performed, in one possible configuration. In such a configuration, it is also possible to perform a decision of the internal alertness of the driver constantly.

However, eye behaviors that are effective for deciding the alertness of the driver are less likely to be performed in monotonous freeways, and road driving zones where features, front vehicles, signals, and the like do not appear. That is, it is a situation where the behavioral analysis of the driver cannot be expected stably.

What is important in this situation is information presentation that stably always triggers eye behaviors corresponding to fixation searches. For this purpose, it is necessary to suppress repetitions and generate and present information that does not lower sensitivity.

For the purpose of reducing repetitions, it is necessary to prepare plural various problems. In the following, setting examples of problems are depicted.

(1) Problem asking the driver to look at plural animal silhouettes in the descending order of their body weights (2) Problem including processes of displaying animal silhouettes in a state in which they are individually rotated at various angles, and asking the driver to look at the rotated silhouettes, and determine animal types (3) Problem in which similar patterns are displayed by being arrayed, and it is required to check the patterns by fixations at features of the individual patterns for determining differences between the patterns (4) Problem in which plural dishes are arrayed, and it is asked to determine whether each dish is a Japanese food or a western food (5) Problem in which A, B, C, and the like are displayed randomly, and it is requested to look at characters in an order (6) Problem in which livestock animals are set as display patterns (7) Problem in which pets are set as display patterns (8) Problem in which domestic fowls are set as display patterns (9) Problem in which fishes are set as display patterns

(10) Problem in which insects are set as display patterns

For example, these many problems are stored in the display-information storage section 17 depicted in FIG. 6, and the display-information generating section 61 selects and presents problems from these problems such that the same problems are not repeated, in one preferred configuration.

Figure 11:
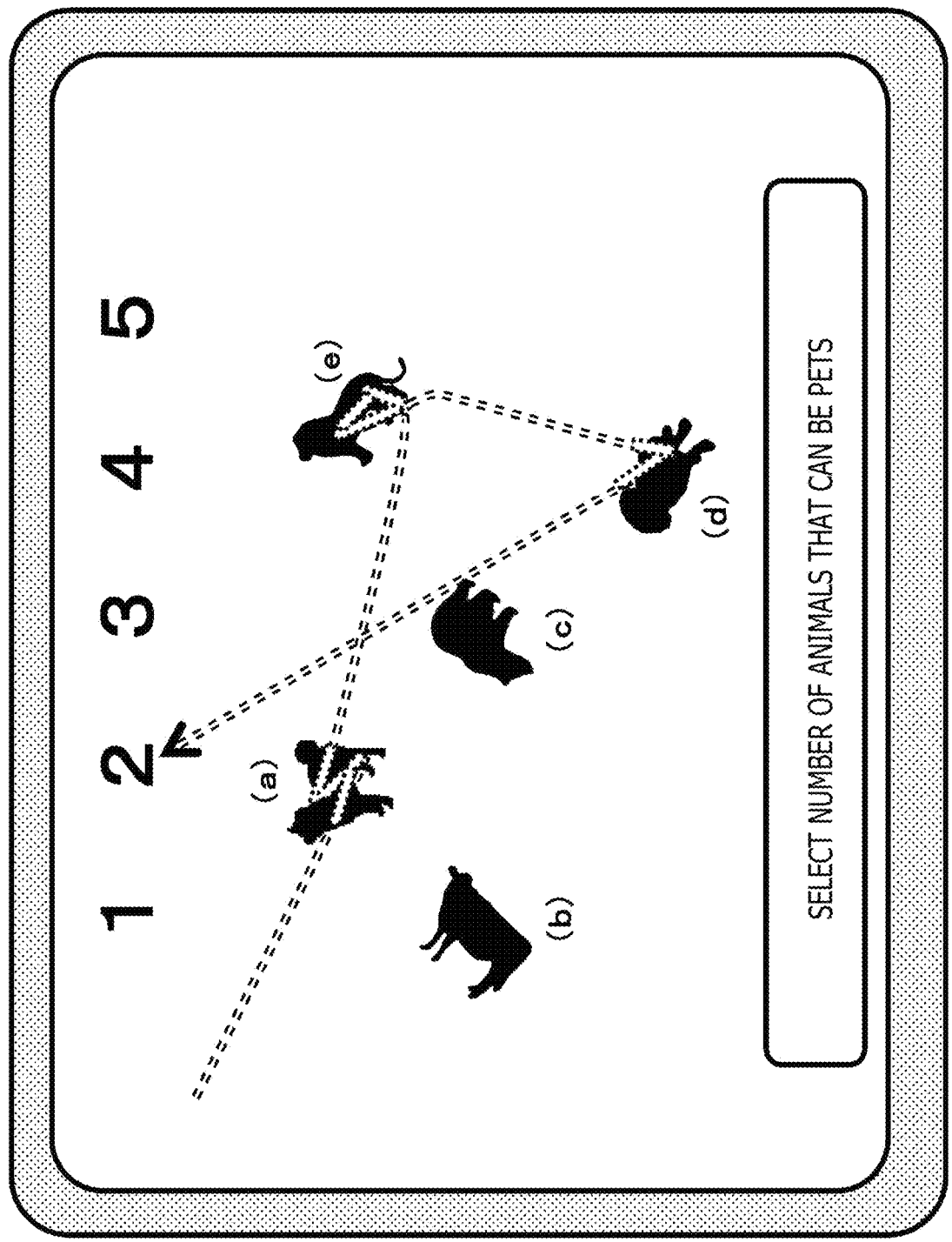
FIG. 11 is a figure for explaining one example of problems to be displayed.

FIG. 11 depicts one example of problems.

While, in the example depicted in FIG. 11 also, plural animal silhouettes are displayed side by side similarly to FIG. 9 and FIG. 10, a problem "SELECT NUMBER OF ANIMALS THAT CAN BE PETS" is presented as a problem sentence.

Five types of animal silhouette, (a) Akita dog,
(b) cow,
(c) bear,
(d) poodle, and
(e) lion are displayed as animal silhouettes, and along with them, selectable numerical values from 1 to 5 are displayed at the upper section.

In a case where "SELECT NUMBER OF ANIMALS THAT CAN BE PETS" is presented as the problem sentence, if it is supposed that the alertness of the driver is sufficiently high, it is predicted that the driver performs eye behaviors following the Steps (S1 and the following Steps) below for problem solving.

(S1) Check the problem (S2) Grasp the whole of the animal silhouettes (S3) Check correlations between information obtained from the overall observation by the peripheral visual field and memories in the brain, and start a saccade (eye rotation) for individual fixations for checking target silhouettes estimated as being eligible for pets (S4) Fixation at the animal silhouette (a) Akita dog (S5) Execute a microsaccade (eye microrotation) for checking the head as a feature of a local portion that is looked at within the central visual field, in order to determine whether or not the animal silhouette (a) is a silhouette of a dog (S6) Saccade (eye rotation) of moving the viewpoint to another animal silhouette (S7) Fixation at the animal silhouette (e) lion (S8) Execute a microsaccade (eye microrotation) for checking the head and tail as features of local portions that are looked at within the central visual field, in order to determine whether or not the animal silhouette (e) is a silhouette of a dog, and determine that the animal silhouette (e) is a silhouette of a lion (S9) Saccade (eye rotation) of moving the viewpoint to another animal silhouette (S10) Fixation at the animal silhouette (d) poodle (S11) Immediately determine that the animal silhouette (d) is a silhouette of a dog without performing a microsaccade (eye microrotation)

(S12) Direct the line of sight to the animal silhouettes (b) and (c) that have entered the visual field at the time of grasping the whole of the animal silhouettes in (S2), and have been tentatively decided as not being eligible for pets, and check again that they are not eligible for pets (S13) Saccade (eye rotation) of moving the line of sight to the numerical value [2] as an answer choice Note that, in a case where the driver is not confident, the line of sight may be moved to the silhouettes (b) and (c) for checking features, accompanying a saccade (eye rotation), in some cases.

The information processing apparatus according to the present disclosure mounted on the moving apparatus presents, for example, a visual problem like the one depicted in FIG. 11 to the driver, analyzes eye behaviors of the driver after the presentation, and decides whether or not the driver is performing eye behaviors for solving the problem (e.g., Steps (S1) to (S13) described above). For example, it is decided that the alertness is high if eye behaviors approximately similar to Steps (S1) to (S13) described above are executed, and if not, it is decided that the alertness is low.

Note that the alertness decision at the information processing apparatus needs not to decide whether or not eye behaviors of the driver completely match Steps (S1) to (S13) described above. For example, in an example process, it is decided that the alertness is high if half (50%) or more of Steps (S1) to (S13) described above are executed, and if not, it is decided that the alertness is low.

Note that the order in which silhouettes are looked at is not limited to that in the example described above. For example, alertness evaluation may be performed on the basis of whether or not microsaccades (eye microrotations) for identifying whether an animal is eligible for a pet or is not eligible for a pet are executed about one or more animal silhouettes.

Figure 12:
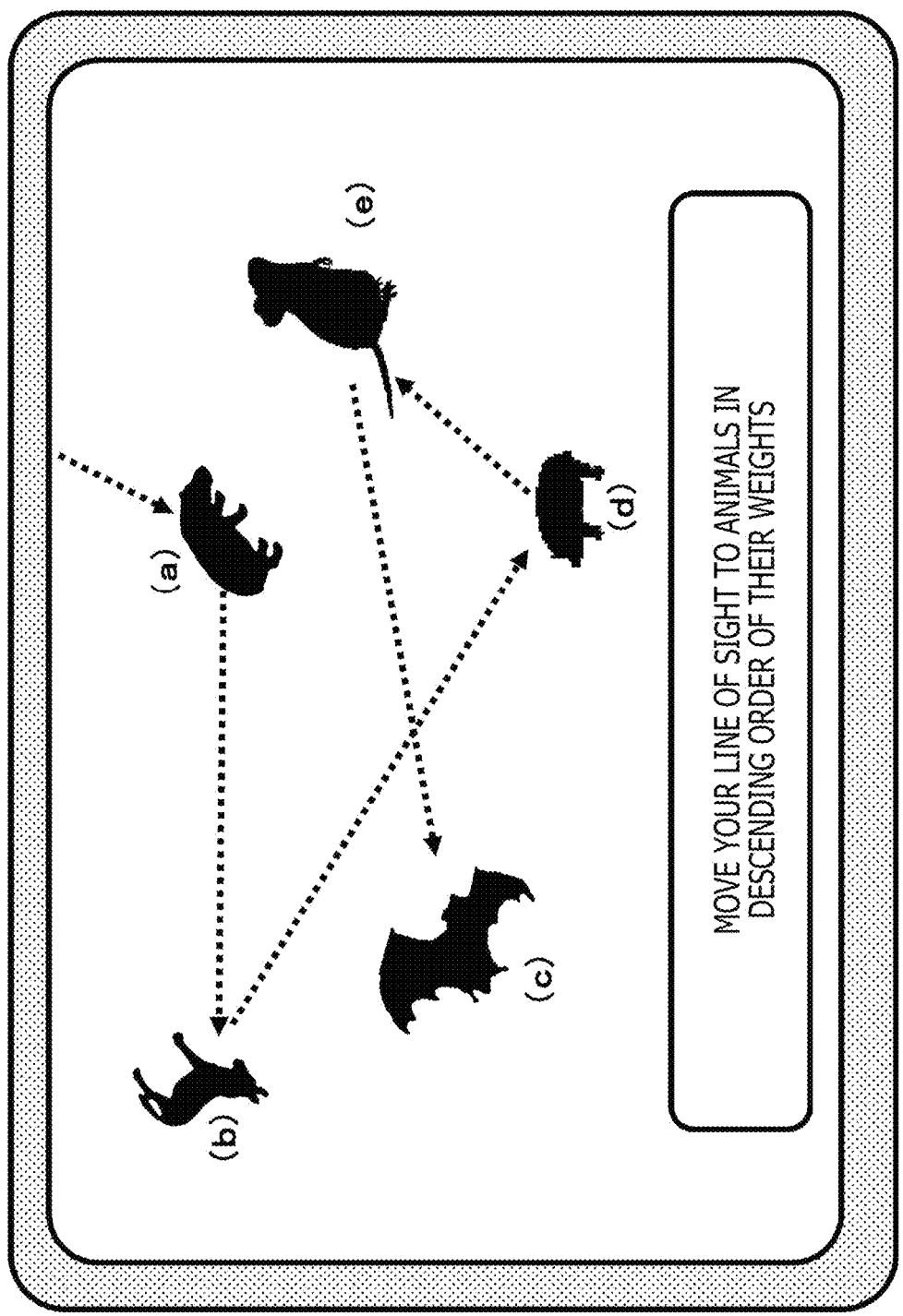
FIG. 12 is a figure for explaining one example of problems to be displayed.

FIG. 12 depicts a different example of problems.

In the example depicted in FIG. 12 also, plural animal silhouettes are displayed side by side, but a problem "MOVE YOUR LINE OF SIGHT TO ANIMALS IN DESCENDING ORDER OF THEIR WEIGHTS" is presented as a problem sentence.

Five types of animal silhouette,
(a) hippopotamus,
(b) horse,
(c) bat,
(d) pig, and
(e) rat are displayed as animal silhouettes.

In a case where "MOVE YOUR LINE OF SIGHT TO ANIMALS IN DESCENDING ORDER OF THEIR WEIGHTS" is presented as a problem sentence, if it is supposed that the alertness of the driver is sufficiently high, it is predicted that the driver performs eye behaviors following the Steps (S1 and the following Steps) below for problem solving.

(S1) Check the problem
(S2) Grasp the whole of the animal silhouettes
(S3) Correlations between information obtained from the overall observation with the peripheral visual field and memories in the brain are checked. For silhouettes for which determinations are difficult, a line-of-sight movement to such a silhouette is performed by a saccade (eye rotation) for checking features, and a fixation, or a microsaccade (eye microrotation) is executed for further checking local features.
(S4) When there are no more targets for which determinations are not possible, saccades (eye rotations) are performed sequentially from larger objects, and the line of sight is moved.

Note that there is a possibility that a fixation or a microsaccade (eye microrotation) for re-checking occurs at the step of the execution of the line-of-sight movement in (S4) in a case where a determination is ambiguous.

The information processing apparatus according to the present disclosure mounted on the moving apparatus presents, for example, a visual problem like the one depicted in FIG. 12 to the driver, analyzes eye behaviors of the driver after the presentation, and decides whether or not the driver is performing eye behaviors for solving the problem (e.g., Steps (S1) to (S4) described above). For example, it is decided that the alertness is high if eye behaviors approximately similar to Steps (S1) to (S4) described above are executed, and if not, it is decided that the alertness is low.

Note that, for example, alertness evaluation may be performed on the basis of whether or not microsaccades (eye microrotations) are executed about one or more animal silhouettes.

Figure 13:
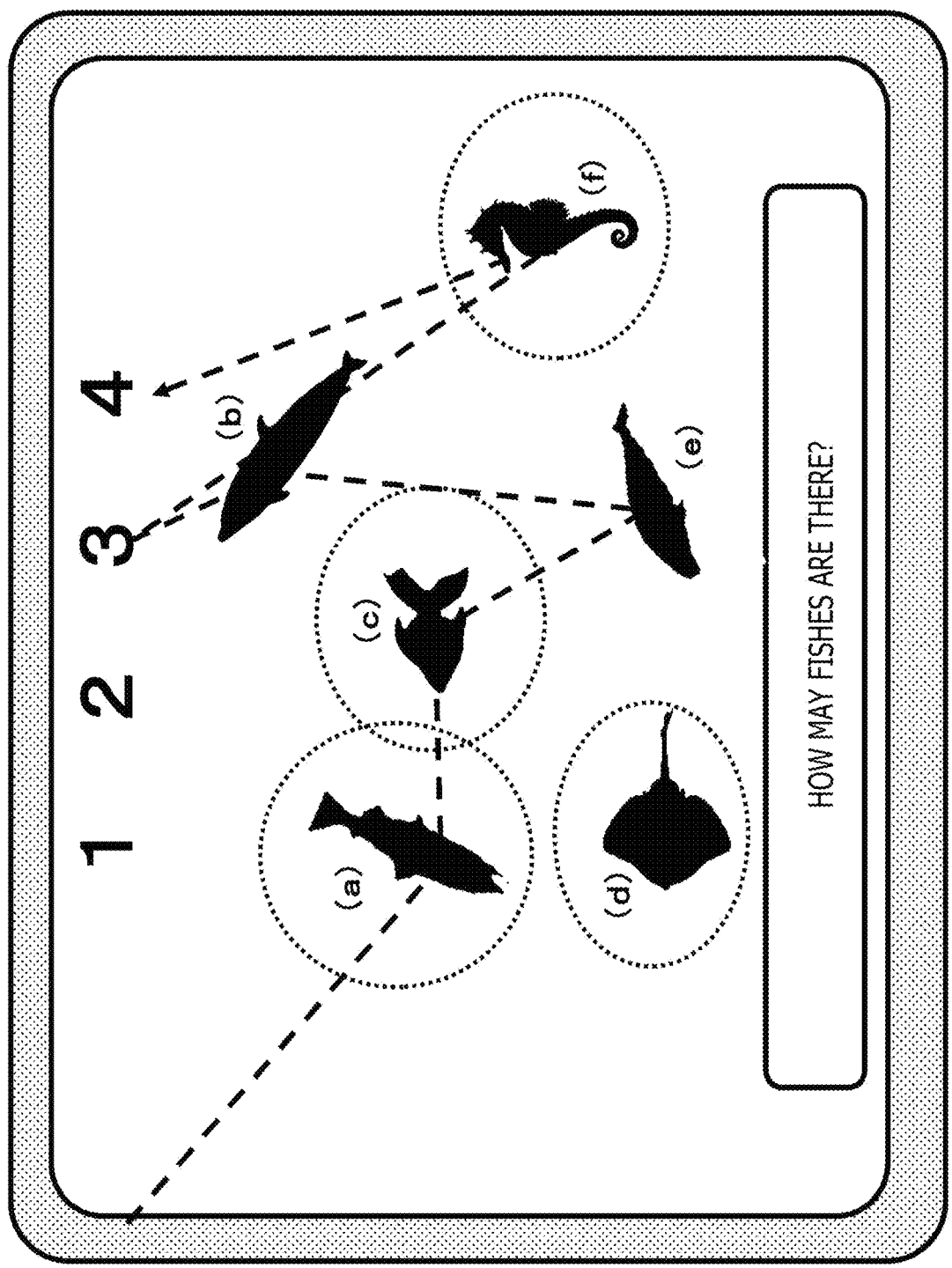
FIG. 13 is a figure for explaining one example of problems to be displayed.

FIG. 13 depicts another problem example.

The example depicted in FIG. 13 is an example in which plural fishes, species of marine life, and the like are displayed side by side, and a problem "HOW MANY FISHES ARE THERE?" is presented as a problem sentence.

Six types of silhouette,
(a) bonito,
(b) dolphin,
(c) goldfish,
(d) ray,
(e) whale, and
(f) sea horse are displayed as silhouettes, and along with them, choices 1 to 4 are displayed.

Note that dotted line frames depicted in the figure are depicted as an example answer, but are not included in the displayed problem.

In a case where "HOW MANY FISHES ARE THERE?" is presented as the problem sentence, if it is supposed that the alertness of the driver is sufficiently high, it is estimated that, as eye behaviors for problem solving, the driver performs processes similar to the behaviors for the problem "SELECT NUMBER OF ANIMALS THAT CAN BE PETS" explained with reference to FIG. 11 before.

That is, steps like the ones mentioned below are executed.
(S1) Check the problem
(S2) Grasp the whole of the silhouettes
(S3) Check correlations between information obtained from the overall observation by the peripheral visual field and memories in the brain, and start a saccade (eye rotation) for individual fixations for checking target silhouettes estimated as being fishes
(S4) A saccade (eye rotation) of checking each silhouette in turn is performed, and in a case where a determination is difficult, a fixation or microsaccade (eye microrotation) for checking features of local portions of each silhouette is executed.
(S5) Saccade (eye rotation) of moving the line of sight to the numerical value [3] as an answer choice The information processing apparatus according to the present disclosure presents, for example, a visual problem like the one depicted in FIG. 13 to the driver, analyzes eye behaviors of the driver after the presentation, and decides whether or not the driver is performing the steps described above as eye behaviors for solving the problem. It is decided that the alertness is high if eye behaviors approximately similar to the steps described above are executed, and if not, it is decided that the alertness is low.

Note that, while the problem depicted in FIG. 13 asks the driver to answer the number of fishes, the line-of-sight behavior changes if the problem is presented repeatedly, for example.

In a case where the driver sees the problem depicted in FIG. 13 for the first time, it is likely that all the silhouettes (a) to (f) look like fishes.

Alternatively, for example, it is expected that the driver feels a doubt about (d) ray, (f) sea horse, and the like, and executes a fixation or a microsaccade (eye microrotation) in order to check details.

On the other hand, in a case where a similar problem or an identical problem is presented again to the driver who has ever seen the problem depicted in FIG. 13, there is a possibility that the driver completes a determination without looking at details, at a step of observing the whole of the plural silhouettes first with the peripheral visual field. In this case, there is a possibility that a fixation or a microsaccade (eye microrotation) for checking local features is not performed. That is, regarding a target with a feature, in a case where the answer of the problem that is asked about the target is not immediately linked with a memory, it is expected that a behavior of looking at details by a microsaccade for checking the details is observed. On the other hand, because features of a seahorse and the like are too noticeable and they remain too strongly in memories. Therefore, a determination is completed at a step when their silhouettes are captured. Problem presentation with various changes that are depicted in other instances illustrated below is part of ingenious ways for suppressing predictability at the step when the driver captures only the overview with the peripheral visual field, and always prompting the driver to check with the central visual field for determinations in the brain.

It should be noted, however, that because the contours of (b) dolphin and (e) whale look like those of fishes, but they are not fishes, there is also a possibility that a fixation or a microsaccade (eye microrotation) of looking hard at the features of their tails, the features of their heads, and the like is executed.

A fixation or a microsaccade (eye microrotation) which is a behavior for checking local features varies depending on experiences, memories, and the like of the driver regarding the time when she/he saw features of patterns to be problems.

Figure 14:
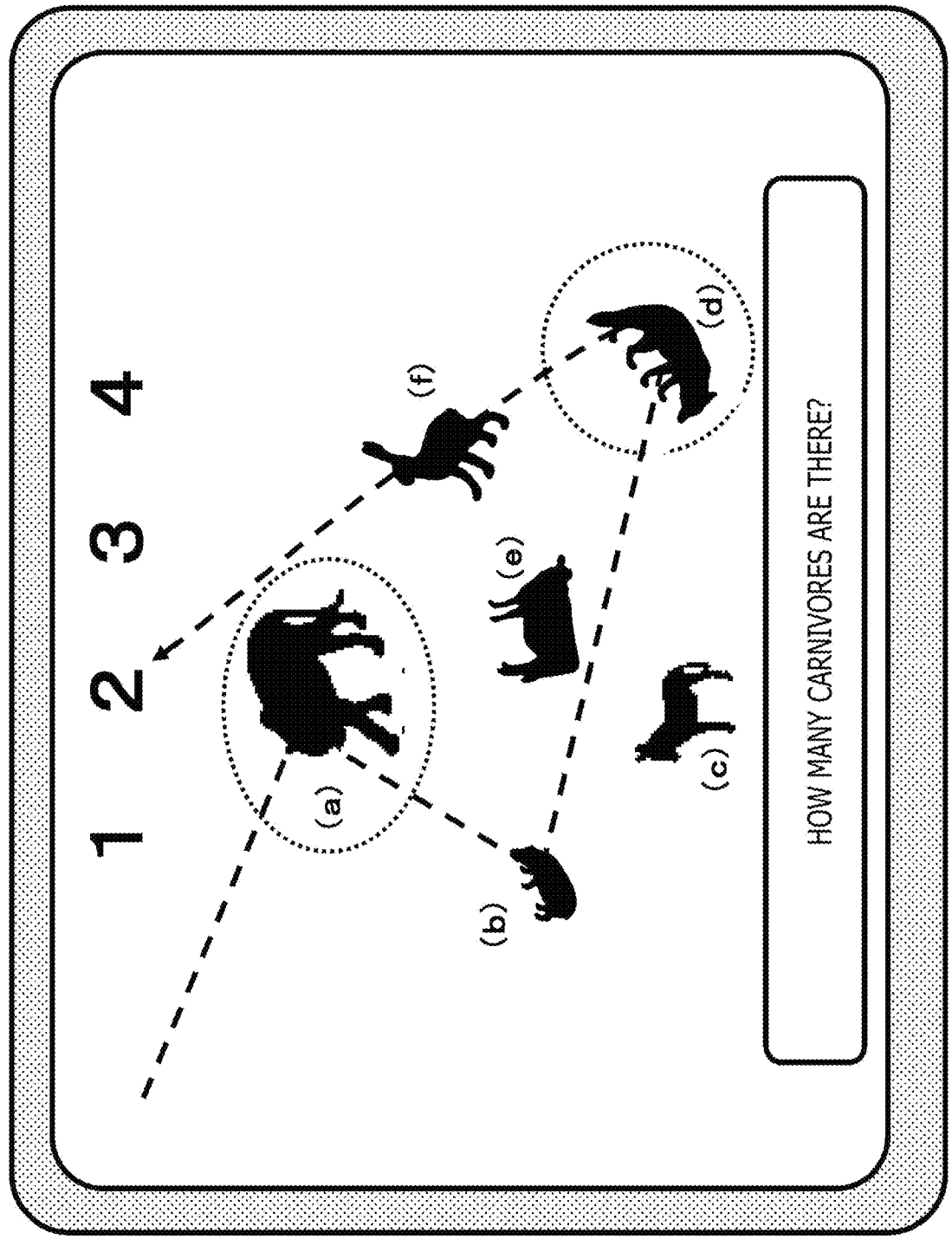
FIG. 14 is a figure for explaining one example of problems to be displayed.
Figure 15:
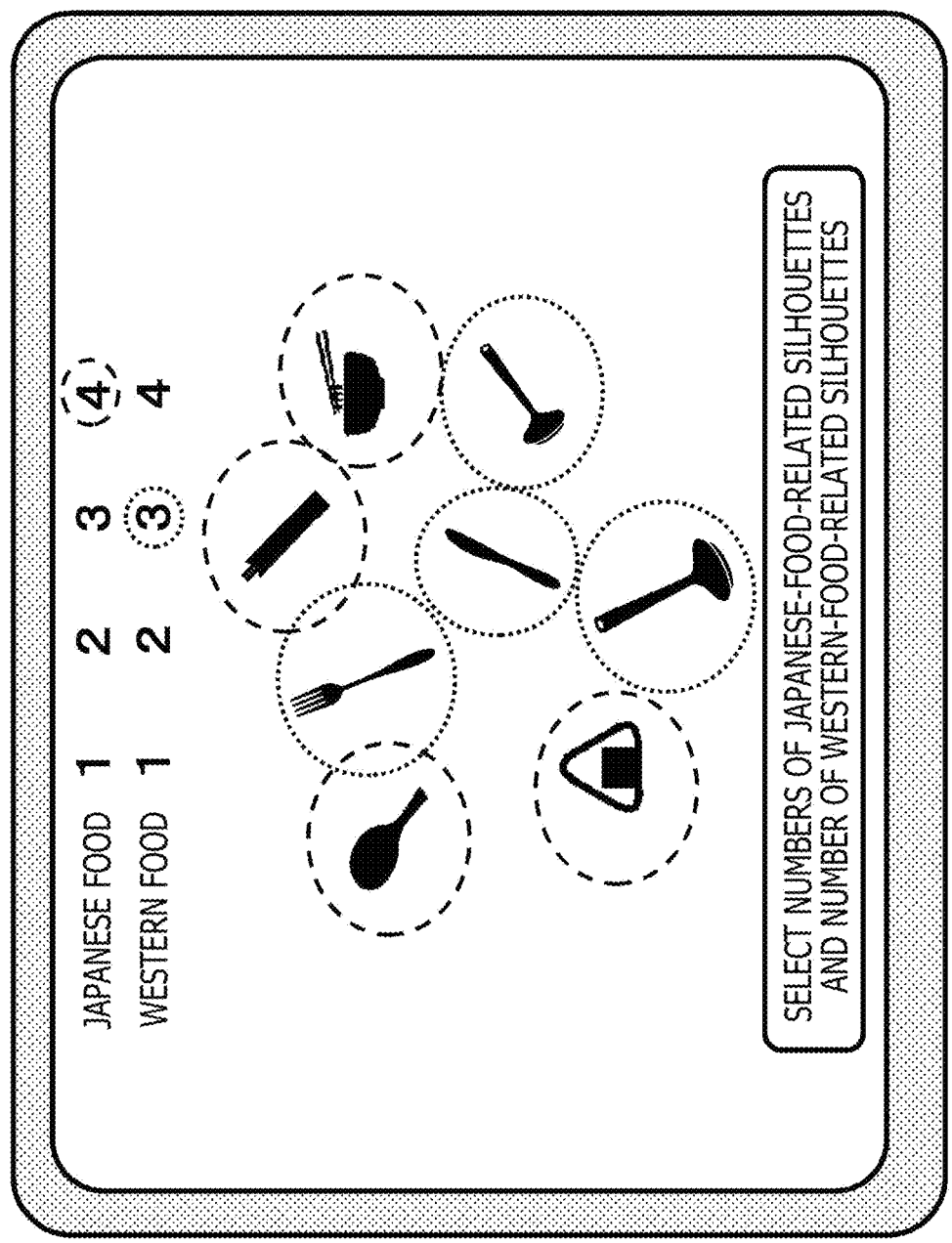
FIG. 15 is a figure for explaining one example of problems to be displayed.
Figure 16:
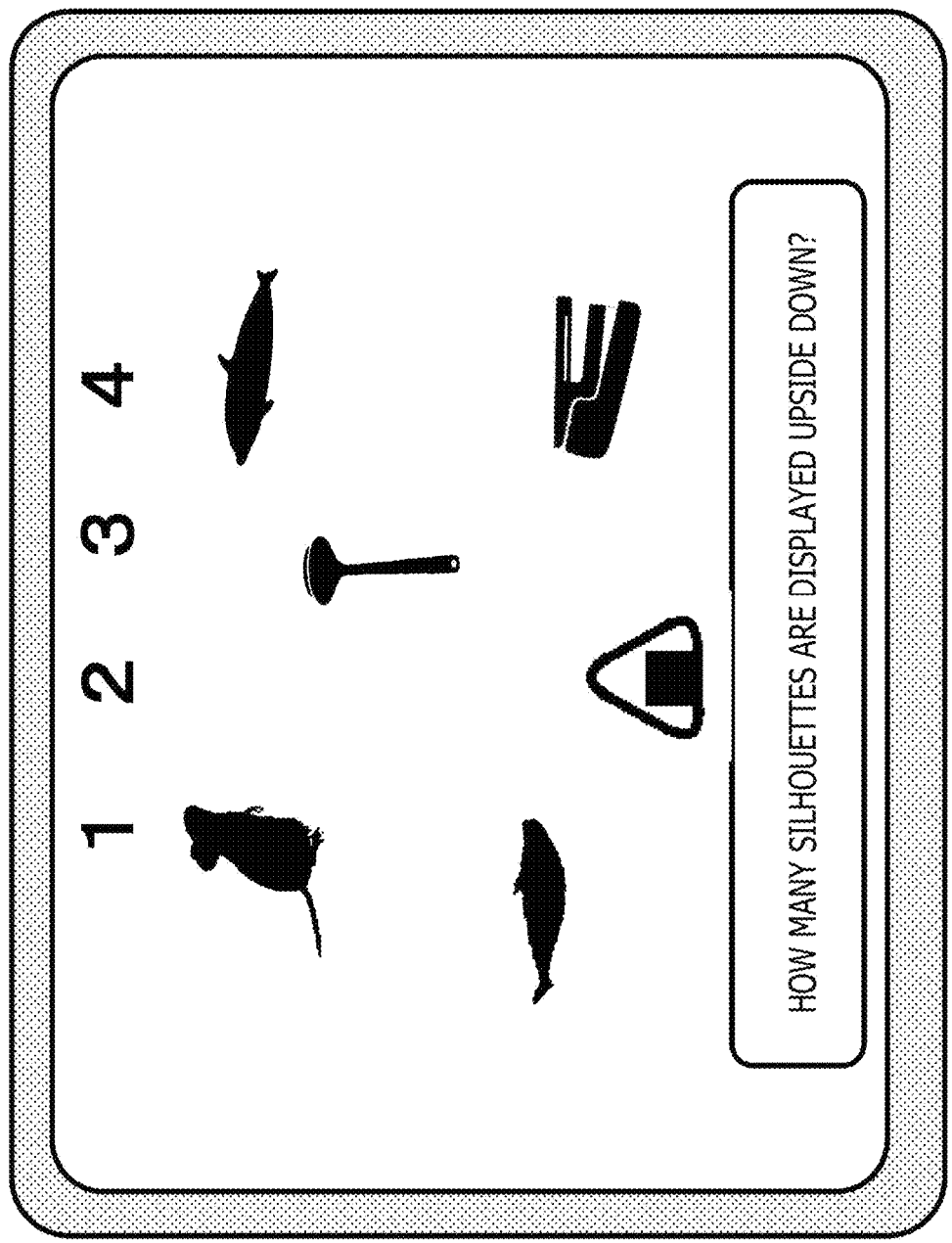
FIG. 16 is a figure for explaining one example of problems to be displayed.

FIG. 14 to FIG. 16 depict other problem examples.

FIG. 14 depicts a problem that displays plural animal silhouettes, and asks the driver to select the number of carnivores.

Note that dotted line frames depicted in the figure are depicted as an example answer, but are not included in the displayed problem.

FIG. 15 depicts a problem that displays silhouettes of plural kitchen utensils and food materials, and asks the driver to select the number of silhouettes corresponding to Japanese food and the number of silhouettes corresponding to western food.

Note that dotted line frames depicted in the figure are depicted as an example answer, but are not included in the displayed problem.

FIG. 16 depicts a problem that displays various types of silhouettes, and asks the driver to select the number of silhouettes that are displayed upside down.

Next, examples of problems that use not images of animal or object silhouettes but characters are explained.

Figure 17:
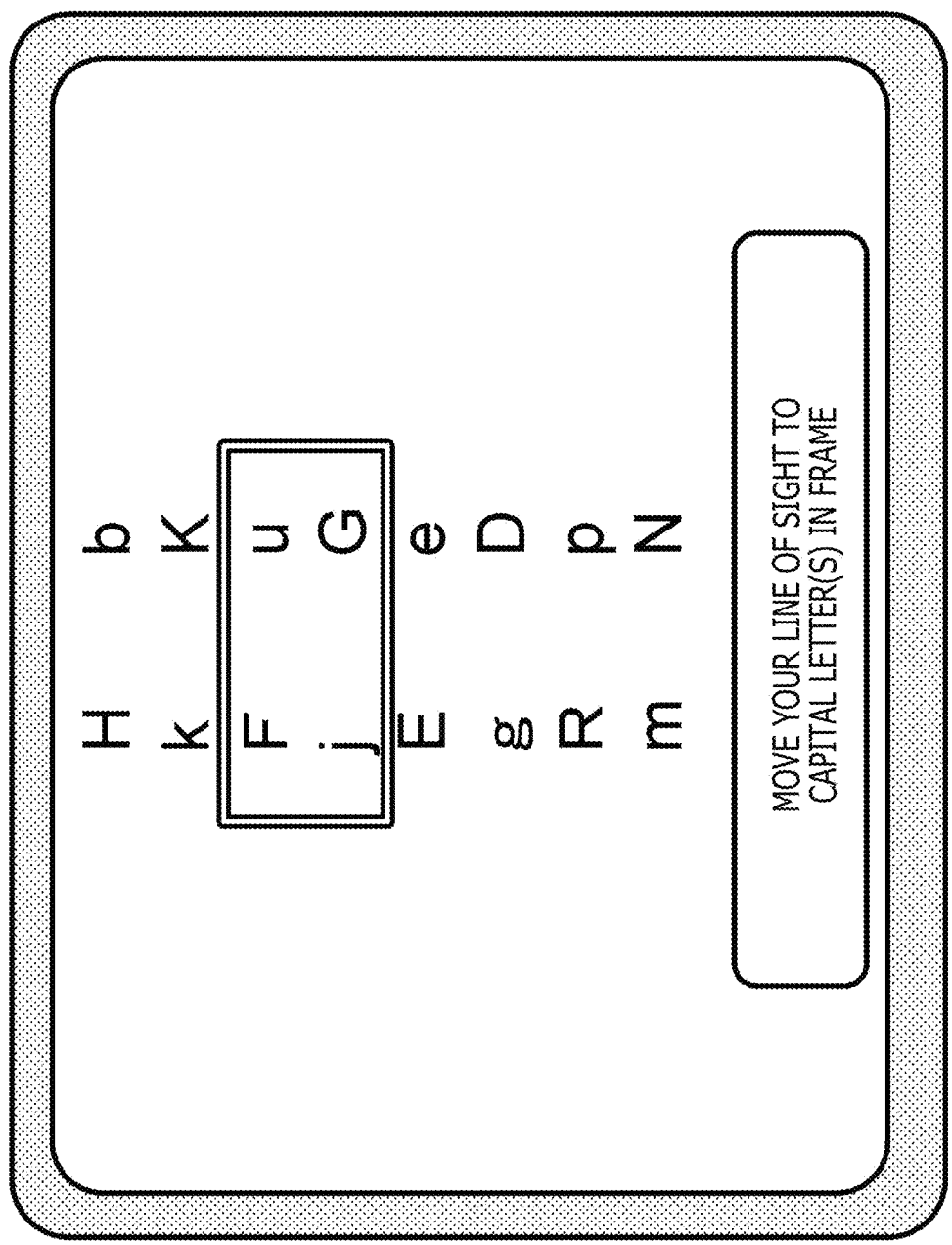
FIG. 17 is a figure for explaining one example of problems to be displayed.

FIG. 17 depicts an example in which alphabetical characters in which uppercase letters and lowercase letters are mixedly present are displayed randomly, and a problem "MOVE YOUR LINE OF SIGHT TO CAPITAL LETTER (S) IN FRAME" is presented as a problem sentence.

The driver performs a saccade (eye rotation), a fixation, a microsaccade (eye microrotation), and the like as eye behaviors to direct his/her line of sight to uppercase alphabetical letters from plural alphabets displayed in the frame.

Further, a problem that has a frame at a different position, and asks the driver to direct the line of sight to lowercase letters may be additionally performed.

By changing problems in such a manner, the driver is requested to perform plural determinations. In order to solve plural different problems, the driver needs to change the activity area in the brain necessary for determinations. Accordingly, more precise alertness decisions become possible by performing an eye behavioral analysis with such composite problems.

Figure 18:
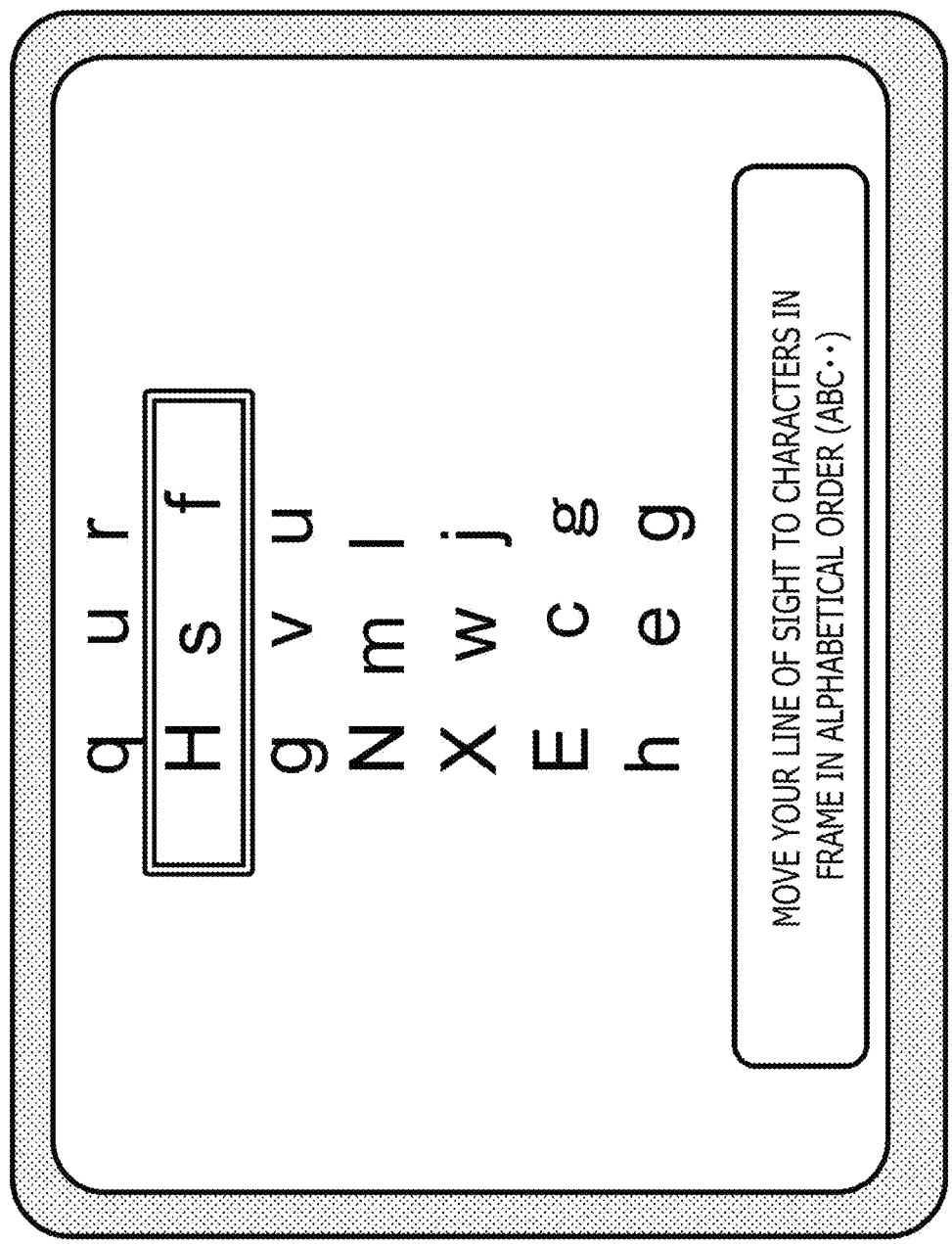
FIG. 18 is a figure for explaining one example of problems to be displayed.

FIG. 18 depicts an example in which alphabetical characters in which uppercase letters and lowercase letters are mixedly present are displayed randomly, and a problem "MOVE YOUR LINE OF SIGHT TO CHARACTERS IN FRAME IN ALPHABETICAL ORDER (ABC . . . )" is presented as a problem sentence.

If such a problem asking the driver to look at characters in the alphabetical order is presented, the driver who has high alertness determines the order of characters, and performs a line-of-sight movement.

Note that the number of characters is limited in the examples explained with reference to FIG. 17 and FIG. 18, and determinations are performed only by referring to memories without performing feature determinations by fixations, in some cases. If such determinations are performed, it becomes less likely to observe eye behaviors such as fixations or microsaccades. Accordingly, it is preferred to present problems that require capturing of features of each character, and trigger eye behaviors.

Figure 19:
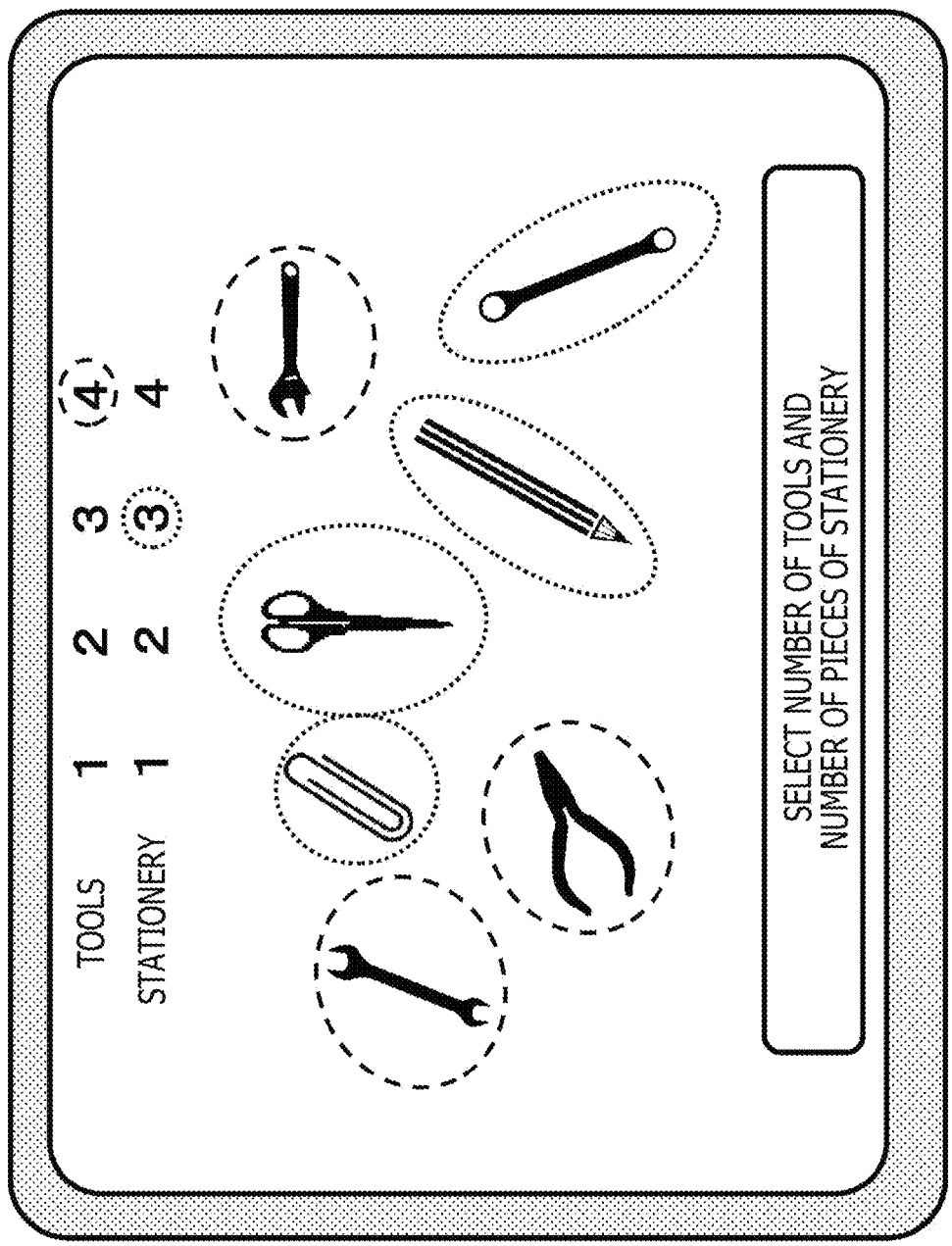
FIG. 19 is a figure for explaining one example of problems to be displayed.

FIG. 19 and the subsequent figures depict other problem examples.

FIG. 19 depicts an example that displays silhouettes of various tools and pieces of stationery, and a problem "SELECT NUMBER OF TOOLS AND NUMBER OF PIECES OF STATIONERY" is presented.

Note that dotted line frames depicted in the figure are depicted as an example answer, but are not included in the displayed problem.

Figure 20:
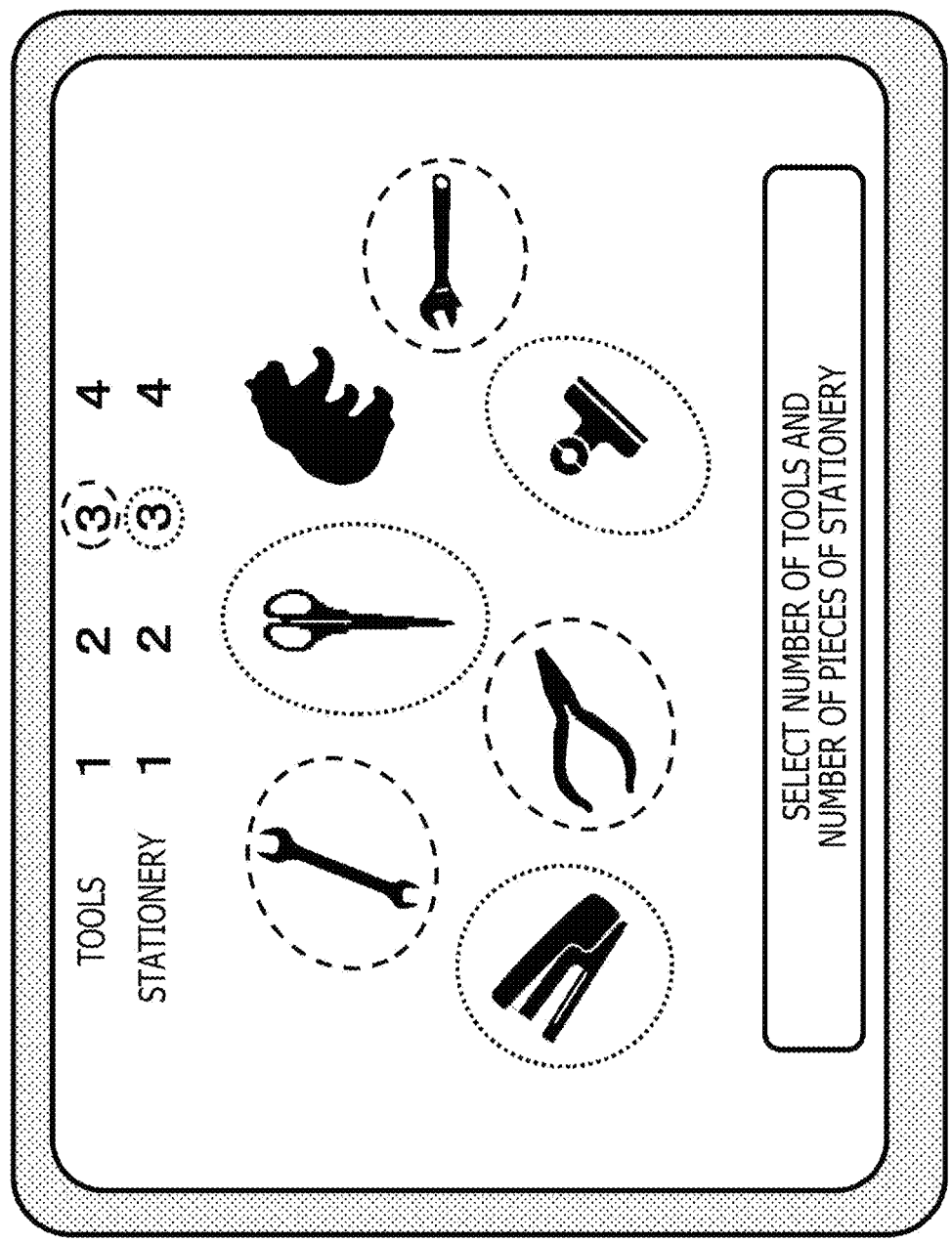
FIG. 20 is a figure for explaining one example of problems to be displayed.

Although FIG. 20 also depicts an example in which a problem "SELECT NUMBER OF TOOLS AND NUMBER OF PIECES OF STATIONERY" is presented, it is an example in which displayed silhouettes include silhouette of tools and pieces of stationery and silhouettes not included in neither of them (animals).

Note that dotted line frames depicted in the figure are depicted as an example answer, but are not included in the displayed problem.

Figure 21:
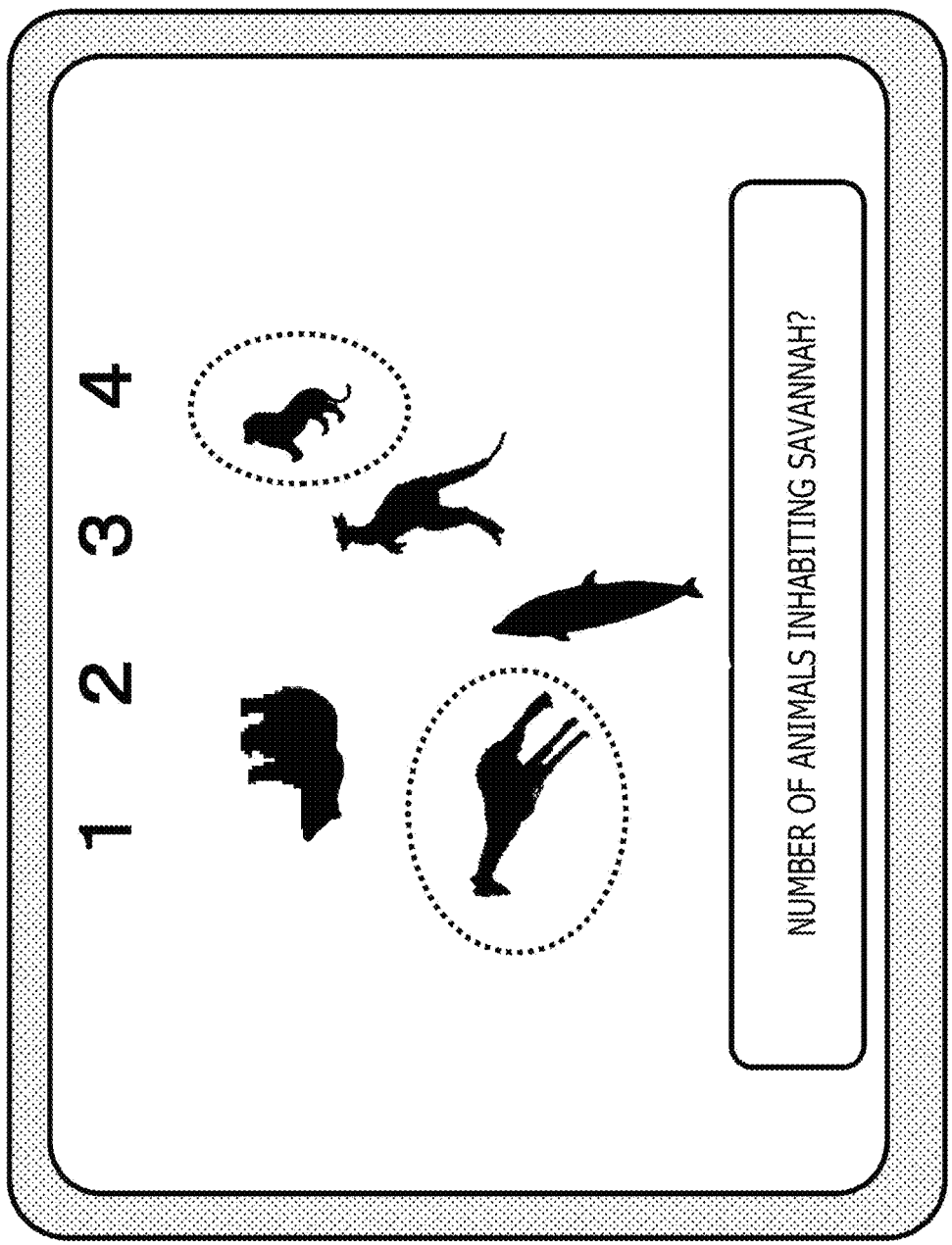
FIG. 21 is a figure for explaining one example of problems to be displayed.

FIG. 21 depicts an example that displays various animal silhouettes, and presents a problem "NUMBER OF ANIMALS INHABITING SAVANNAH?"

Note that dotted line frames depicted in the figure are depicted as an example answer, but are not included in the displayed problem.

Figure 22:
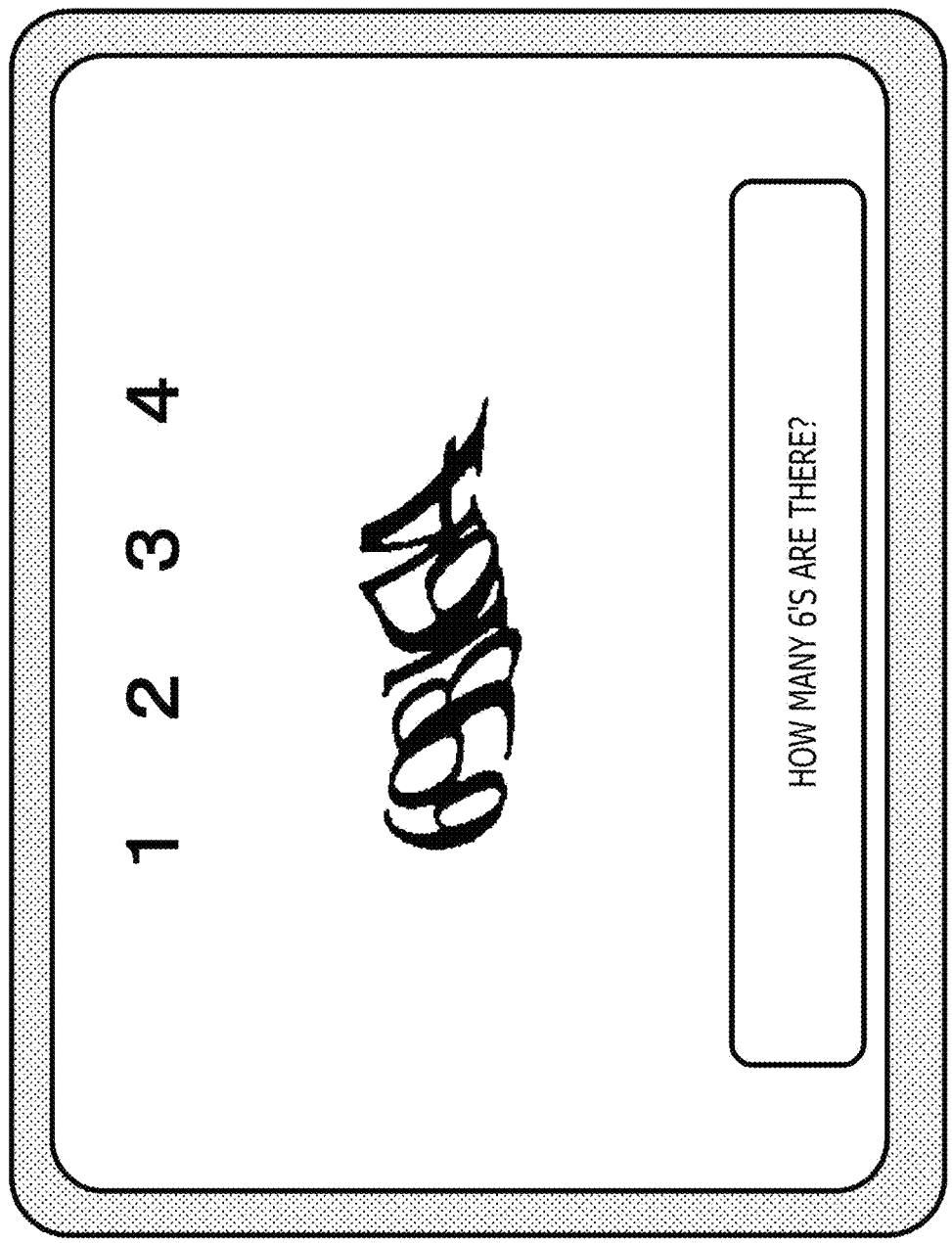
FIG. 22 is a figure for explaining one example of problems to be displayed.

FIG. 22 depicts an example that displays a deformed string, and presents a problem "HOW MANY 6'S ARE THERE?"

Problems that involve processes asking the driver to choose odd numbers, even numbers, vowels, consonants, Greek characters, and the like such as the process asking the driver to select particular characters or numbers from a deformed string as depicted in FIG. 22 are effective problems for triggering line-of-sight movements and eye behaviors.

Figure 23:
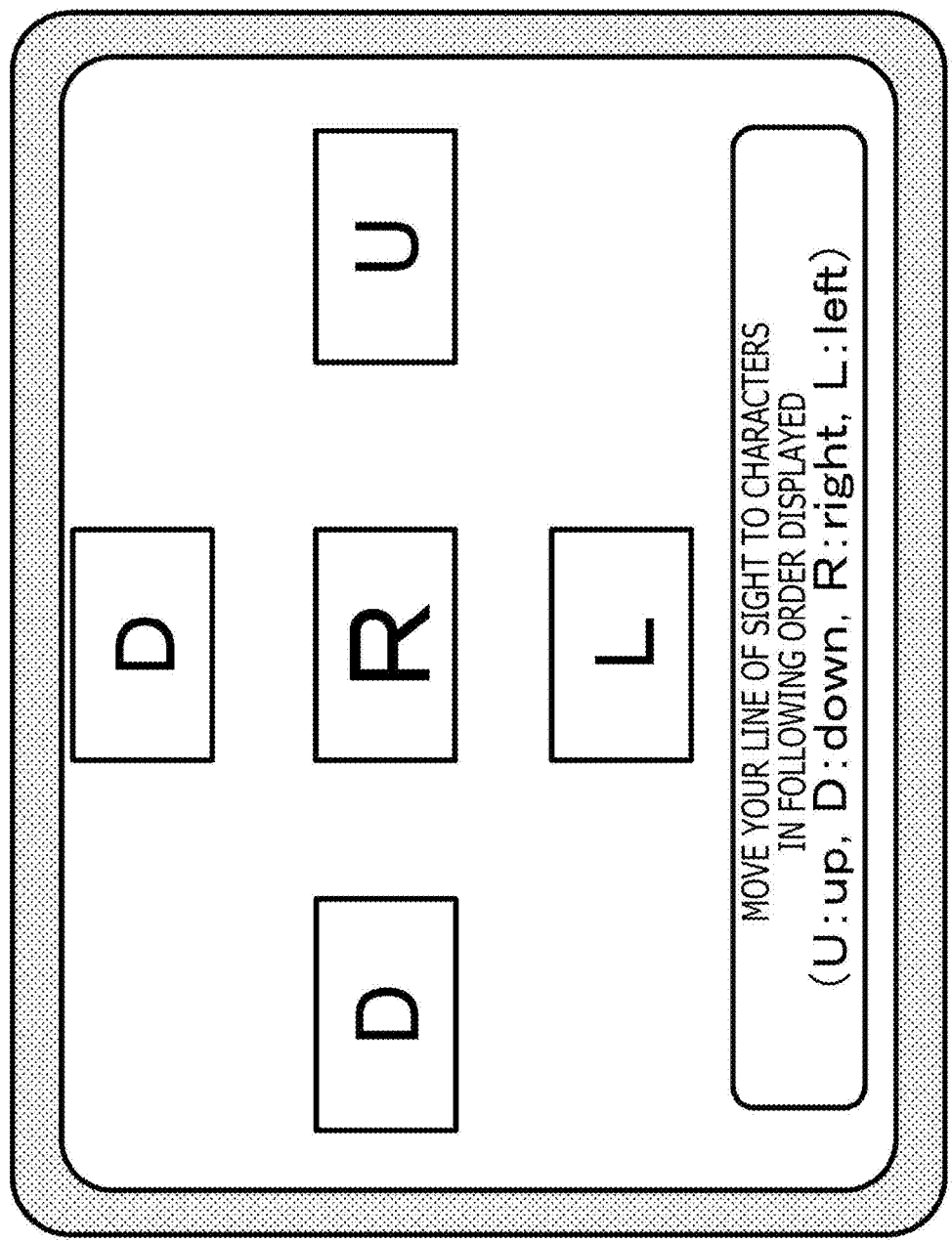
FIG. 23 is a figure for explaining one example of problems to be displayed.

Further, FIG. 23 depicts an example that displays characters, U, D, R, and L, and presents a problem "MOVE YOUR LINE OF SIGHT TO CHARACTERS IN FOLLOWING ORDER DISPLAYED (U: up, D: down, R: right, L: left)."

The driver performs a process of looking at those characters one by one, and moving his/her line of sight toward directions according to the characters.

In this process, the driver performs eye behaviors such as a saccade (eye rotation), a fixation, or a microsaccade (eye microrotation).

Figure 24:
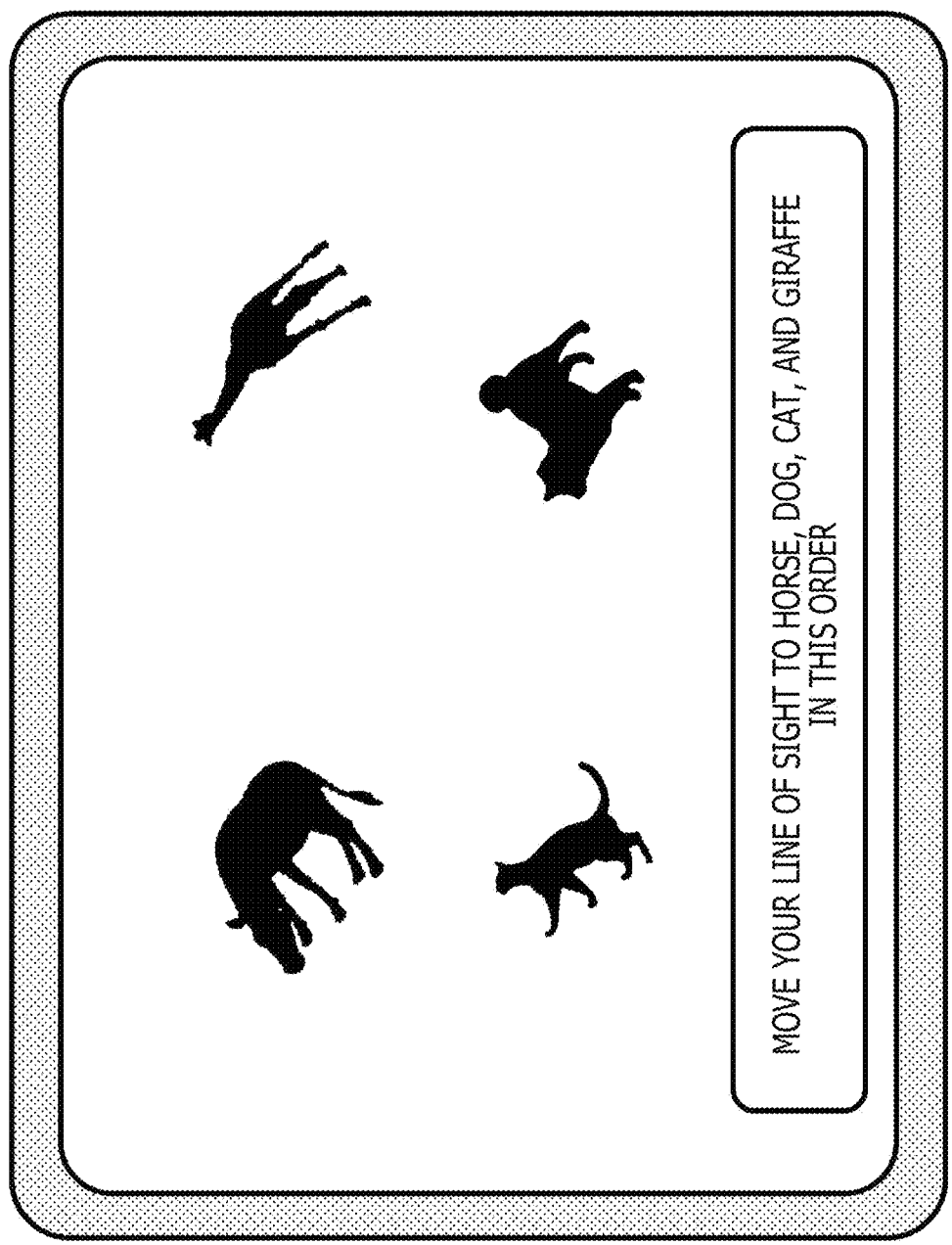
FIG. 24 is a figure for explaining one example of problems to be displayed.

Further, FIG. 24 depicts an example that displays silhouettes of plural different animals, and presents a problem "MOVE YOUR LINE OF SIGHT TO HORSE, DOG, CAT, AND GIRAFFE IN THIS ORDER."

The driver performs a process of moving the line of sight to horse, dog, cat, and giraffe in this order.

In this process, the driver performs eye behaviors such as a saccade (eye rotation), a fixation, or a microsaccade (eye microrotation).

While various problem examples are explained with reference to FIG. 9 to FIG. 24, problems that are presented to the driver need to be problems that require the work of additionally searching for missing information in order to solve the problems. Specifically, those problems are problems that trigger at least any one eye behavior of a saccade (eye rotation), a fixation, or a microsaccade (eye microrotation) of eyes as eye behaviors for solving the problems.

While the problem examples explained with reference to FIG. 9 to FIG. 24 include problems in which animal and object silhouettes are arranged, problems in which characters are arrayed, and the like, other than those silhouettes and characters, various display data such as symbols, signs, or pictograms can be used.

In such a manner, the information processing apparatus according to the present disclosure presents various visual problems to the driver. The driver-behavior analyzing section 63 of the data processing section 11 of the information processing apparatus depicted in FIG. 6 analyzes eye behaviors of the driver after problem presentation. Specifically, the presence or absence of particular eye behaviors such as a saccade (eye rotation), a fixation, or a microsaccade (eye microrotation) as eye behaviors is detected.

Note that the instances and expected eye behaviors that would be exhibited at that time by the driver to be a respondent depicted in FIG. 9 to FIG. 24 are merely examples. It depends on respondents what behaviors they exhibit. Respondents first look at answer choices without looking at an answer, and later check a question sentence in some cases, respondents repeatedly check a question sentence in some other cases, and so on. What is important is not the accuracy or repetition of behaviors themselves, the length of time until the driver directly obtains the correct answer, and the like, but the degree of occurrence of personal features that are observed at the time when the driver has alertness such as a microsaccade or a fixation for acquiring necessary information, accompanying the problem handling until the driver answers.

That is, it is possible to estimate the internal alertness level of the driver on the basis of the rate of the appearance of characteristic behaviors like a saccade, a microsaccade, or a fixation as a response to a problem at the time when the driver has alertness, or the like.

Eye behavior observation information regarding a saccade (eye rotation), a fixation, a microsaccade (eye microrotation), and the like obtained through the analysis by the driver-behavior analyzing section 63 is input to the driver-alertness deciding section 65.

On the basis of the eye behavior observation information of the driver input from the driver-behavior analyzing section 63, the driver-alertness deciding section 65 decides whether or not the driver has high alertness at a level sufficient for execution of manual driving.

Specifically, it is decided whether or not particular eye behaviors such as a saccade (eye rotation), a fixation, or a microsaccade (eye microrotation) observed as eye behaviors of the driver are occurring according to a sequence for solving a problem presented to the driver. If the eye behaviors are occurring according to the sequence, it is decided that the driver has a sure problem-solving ability, that is, the driver has high alertness, and is in the alertness state in which he/she can execute manual driving. On the other hand, if the eye behaviors are not occurring according to the sequence, it is decided that the alertness of the driver is low, and the driver is not in the alertness state in which he/she can execute manual driving.

[6. About Sequence of Driver Alertness Deciding Process Executed by Information Processing Apparatus According to Present Disclosure]

Next, a sequence of the driver alertness deciding process executed by the information processing apparatus according to present disclosure is explained.

Figure 25:
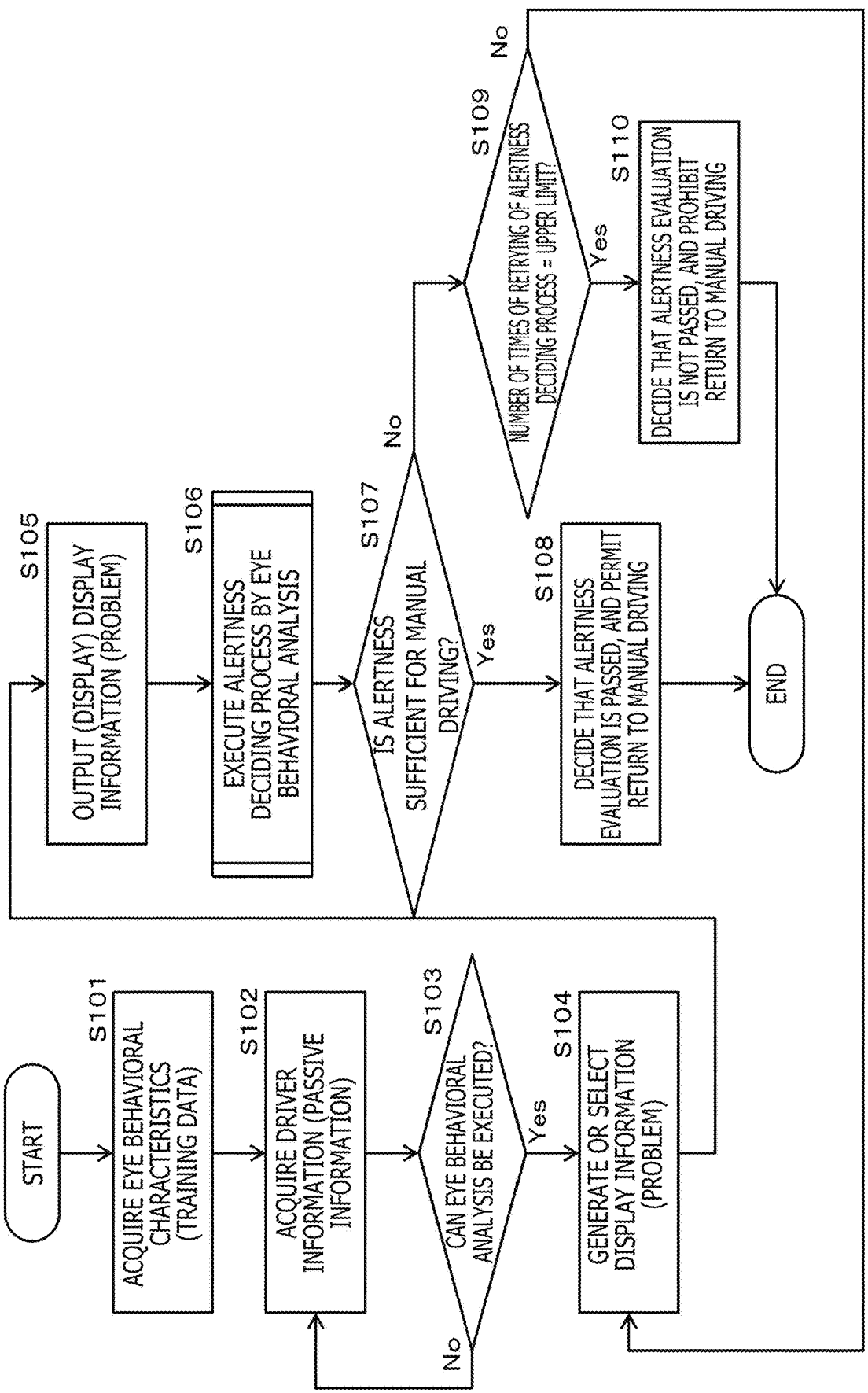
FIG. 25 is a figure depicting a flowchart for explaining one example of a process sequence to be executed by the information processing apparatus according to the present disclosure.
Figure 26:
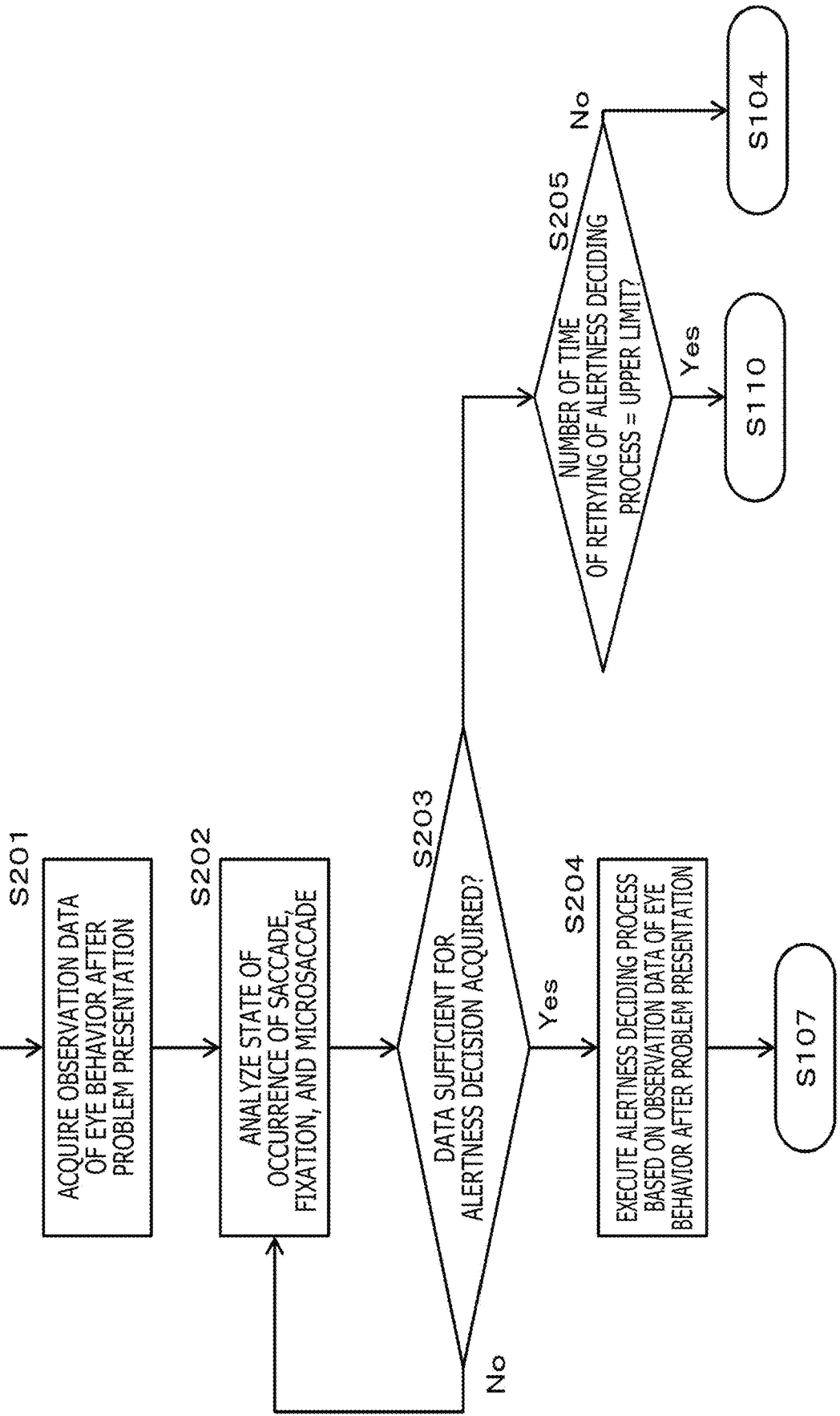
FIG. 26 is a figure depicting a flowchart for explaining one example of the process sequence to be executed by the information processing apparatus according to the present disclosure.

FIG. 25 and FIG. 26 are figures depicting flowcharts for explaining the sequence of the driver alertness deciding process to be executed by the information processing apparatus according to the present disclosure.

Note that the process according to the flowcharts depicted in FIG. 25 and FIG. 26 can be executed according to a program stored on the storage section of the information processing apparatus, and is executed at the data processing section having a program-executing functionality such as a CPU.

In the following, the process at each step of the flow depicted in FIG. 25 is explained sequentially.

(Step S101)

First, in Step S101, the data processing section of the information processing apparatus acquires eye behavioral characteristics data (training data).

This process is executed by the driver-eye-behavior analyzing section 63 of the data processing section 11 depicted in FIG. 6 as a process of acquiring driver-specific eye behavioral characteristics data (training data) from a memory (storage section) in the driver-eye-behavior learner 64.

Note that the training data may be generated by and retained in an external server in one possible configuration. In this case, the training data is acquired from the external server.

The driver-specific eye behavioral characteristics data (training data) is data having been acquired through a training process executed in advance.

As mentioned before, there are differences in eye behaviors between individuals, and in a preferred configuration, similar processes are not performed for all drivers, but rather processes are performed on the basis of driver-specific data.

This is because there is a possibility that drivers having abundant driving experiences and competitive race drivers have different alertness states as compared to those of inexperienced drivers even if they exhibited the same eye behaviors.

Accordingly, a training dictionary generated by a training process for each driver is used to perform an alertness decision, preferably.

Note that, in a case where individual-specific training data is not generated, the process is performed by using eye behavioral characteristics data (training data) of an average person that is prepared in advance.

(Step S102)

Next, driver information is acquired. The process is a process executed by the driver-information acquiring section 12 depicted in FIG. 6.

The driver information acquired in this Step S102 is mainly passive information, and the motion of the face of the driver is acquired by the driver facial tracking section (Driver Facial Tracker) 51 depicted in FIG. 6.

On the basis of the acquired motion of the face of the driver, it is decided whether or not to select a display section on which a problem is to be presented, and a display-section selection process or the like is performed.

(Step S103)

Next, in Step S103, it is decided whether or not selection of a display section on which a problem is to be presented and the eye behavioral analysis process can be executed, on the basis of the driver information acquired in Step S102.

For example, in a case where the driver is not at a position where there is a display section, the driver cannot see a problem even if the problem is displayed on a display section.

In this case (Step S103=No), for example, processes of outputting an alert, notifying the driver that a problem is to be presented on a display section, and so on are performed, further the process returns to Step S102, and the driver information acquisition process is executed continuously.

In a case where it is decided, in Step S103, that selection of a display section on which a problem to be presented and the eye behavioral analysis process can be executed on the basis of the driver information, the process proceeds to Step S104.

(Step S104)

In Step S104, display information to be displayed on a display section that the driver can see, that is, a problem, is generated or selected.

This process is a process executed by the display-information generating section 61 of the data processing section 11 depicted in FIG. 6.

The display-information generating section 61 generates a problem to be displayed on the display section 16. Specifically, the display-information generating section 61 generates a problem such as the problem explained above asking the driver to select one pattern with a different feature from plural animal silhouettes.

Note that the display-information storage section 17 depicted in FIG. 6 has stored therein problems or data for problem generation that can be used for generating various problems, and the display-information generating section 61 selects a problem stored on the display-information storage section 17, or generates a problem to be displayed on the display section 16 by using the stored data.

The problems are problems like the ones explained with reference to FIG. 9 to FIG. 24 before, for example, and are problems by which particular eye behaviors such as a saccade (eye rotation), a fixation, or a microsaccade (eye microrotation) can be observed as eye behaviors of the driver in a case where problem solving by the driver is performed.

(Step S105)

Next, in Step S105, the display information selected or generated in Step S104, that is, the problem, is displayed on a display section.

This process is executed by the display-section selecting section 62 depicted in FIG. 6.

The display-section selecting section 62 depicted in FIG. 6 selects a display section on which the problem generated by the display-information generating section 61 is to be displayed. As depicted in the figure, the display section 16 includes various display sections such as the display section A (instrument panel) 71, the display section B (front window display section) 72, the display section C (wearable/portable display section) 73, or the display section D (HUD (head-up display)) 74.

On the basis of motion information of the face and head of the driver detected by the driver facial tracking section (Driver Facial Tracker) 51, the display-section selecting section 62 selects a display section ahead of the line of sight of the driver as a display section on which the problem generated by the display-information generating section 61 is to be displayed, and causes the selected display section to display the problem.

(Step S106)

Next, in Step S106, an alertness deciding process by an eye behavioral analysis is executed.

This process is a process executed by the driver-eye-behavior analyzing section 63 and the driver-alertness deciding section 65 depicted in FIG. 6.

The driver-eye-behavior analyzing section 63 depicted in FIG. 6 receives, as an input, the motion information of the eyes of the driver detected by the driver-eye tracking section (Driver Eye Tracker) 52 depicted in FIG. 6, and analyzes the motion of the eyes of the driver.

When the problem generated by the display-information generating section 61 is displayed on the display section 16, the driver moves his/her line of sight to the problem in order to acquire the answer of the problem. For example, as mentioned before, a determination-requiring visual problem like the problem asking the driver to select one with a different feature from plural animal silhouettes is displayed on the display section 16. In order to acquire the answer of the problem, the driver performs eye behaviors for additionally acquiring necessary information. For example, the driver performs eye behaviors such as a saccade (eye rotation), a fixation, or a microsaccade (eye microrotation) of eyes.

The driver-eye-behavior analyzing section 63 analyzes the eye behaviors of the driver.

The eye behavior information obtained through the analysis by the driver-eye-behavior analyzing section 63 is input to the driver-alertness deciding section 65.

On the basis of the eye behavior information obtained through the analysis by the driver-eye-behavior analyzing section 63, the driver-alertness deciding section 65 decides the alertness of the driver.

In a case where it is confirmed that the driver is executing eye behaviors such as a saccade (eye rotation), a fixation, or a microsaccade (eye microrotation) of eyes for problem solving, the driver-alertness deciding section 65 decides that the alertness of the driver is high. On the other hand, in a case where these eye behaviors are not observed or in a case where these eye behaviors are not observed sufficiently, the driver-alertness deciding section 65 decides that the alertness of the driver is low.

A detailed flow of the process in Step S106 is depicted in FIG. 26. The process at each step of the flow depicted in FIG. 26 is explained.

(Step S201)

First, in Step S201, observation data of eye behaviors of the driver after problem presentation is acquired.

This process is a process executed by the driver-eye-behavior analyzing section 63 depicted in FIG. 6.

The driver-eye-behavior analyzing section 63 acquires acceleration data of the motion of the eyes of the driver detected by the driver-eye tracking section (Driver Eye Tracker) 52 depicted in FIG. 6.

(Step S202)

Next, in Step S202, eye behavior information regarding a saccade (eye rotation), a fixation, a microsaccade (eye microrotation), or the like of eyes is acquired from the observation data acquired in Step S201.

This process also is a process executed by the driver-eye-behavior analyzing section 63 depicted in FIG. 6.

When a problem is displayed on a display section as mentioned before, the driver performs eye behaviors for acquiring information necessary for solving the problem. For example, the driver performs eye behaviors such as a saccade (eye rotation), a fixation, or a microsaccade (eye microrotation) of eyes. The driver-eye-behavior analyzing section 63 extracts the driver eye behavior information from the observation data.

(Step S203)

Next, in Step S203, the driver-eye-behavior analyzing section 63 decides whether or not data sufficient for an alertness decision could be acquired.

Specifically, it is decided whether or not the eye behavior information regarding a saccade (eye rotation), a fixation, a microsaccade (eye microrotation), or the like of eyes extracted from the driver observation data is data sufficient for deciding whether or not it is data corresponding to a problem-solving process.

In a case where it is decided that the information is sufficient, the process proceeds to Step S204.

On the other hand, in a case where it is decided that the information is insufficient, the process proceeds to Step S205.

(Step S204)

In a case where it is decided, in Step S203, that the eye behavior information regarding a saccade (eye rotation), a fixation, a microsaccade (eye microrotation), or the like of eyes extracted from the driver observation data is data sufficient for deciding whether or not it is data corresponding to a problem-solving process, the process proceeds to Step S204.

In Step S204, the alertness of the driver is decided on the basis of the observation data of eye behaviors of the driver after problem presentation.

This process is a process executed by the driver-alertness deciding section 65 depicted in FIG. 6.

The driver-alertness deciding section 65 depicted in FIG. 6 executes a decision of the alertness of the driver on the basis of eye behaviors of the driver after the problem presentation, that is, the eye behavior observation information regarding a saccade (eye rotation), a fixation, a microsaccade (eye microrotation), or the like.

The driver-alertness deciding section 65 analyzes whether or not the driver is executing eye behaviors such as a saccade (eye rotation), a fixation, or a microsaccade (eye microrotation) of eyes for problem solving.

In a case where the driver-alertness deciding section 65 determines that eye behaviors of the driver are eye behaviors equivalent to a saccade (eye rotation), a fixation, or a microsaccade (eye microrotation) for problem solving, the driver-alertness deciding section 65 decides that the alertness of the driver is high.

On the other hand, in a case where these eye behaviors are not observed or in a case where these eye behaviors are not observed sufficiently, the driver-alertness deciding section 65 decides that the alertness of the driver is low.

Upon completion of this alertness deciding process, the process proceeds to Step S107 in the flow of FIG. 25.

(Step S205)

On the other hand, in a case where it is decided, in Step S203, that the eye behavior information regarding a saccade (eye rotation), a fixation, a microsaccade (eye microrotation), or the like of eyes extracted from the driver observation data is not data sufficient for deciding whether or not it is data corresponding to a problem-solving process, the process proceeds to Step S205.

In Step S205, it is decided whether or not the upper limit of the number of times of retrying of the alertness deciding process specified in advance is reached.

In a case where the upper limit is not reached, the process proceeds to Step S104 of FIG. 25. In this case, new display information (problem) is presented, and the process of observing eye behaviors of the driver is executed again.

On the other hand, in a case where the upper limit is reached, the process proceeds to Step S110 of FIG. 25. In this case, it is decided, in Step S110, that the alertness evaluation is not passed, that is, it is not possible to confirm that the driver has alertness sufficient to return to manual driving, and the process is ended. In this case, it is not permitted to return to manual driving, and the automobile performs a process, such as an emergency stop, to avoid the entrance to a manual driving zone.

Returning to FIG. 25, the processes at and after Step S107 are explained.

(Step S107)

The process in Step S107 is executed after the alertness deciding process by the eye behavioral analysis is completed in Step S106.

In Step S107, it is decided, as a result of the alertness deciding process by the eye behavioral analysis in Step S106, whether or not the alertness of the driver is at a level sufficient for execution of manual driving.

This process is a process executed by the driver-alertness deciding section 65 depicted in FIG. 6.

As mentioned before, the driver-alertness deciding section 65 executes a process of deciding the alertness of the driver on the basis of eye behaviors of the driver after the problem presentation, that is, the eye behavior observation information regarding a saccade (eye rotation), a fixation, a microsaccade (eye microrotation), or the like.

In a case where the driver-alertness deciding section 65 determines that eye behaviors of the driver are eye behaviors equivalent to a saccade (eye rotation), a fixation, or a microsaccade (eye microrotation) for problem solving, the driver-alertness deciding section 65 decides that the alertness of the driver is high, that is, the alertness of the driver is at a level sufficient for execution of manual driving.

In this case, the decision in Step S107 is Yes, and the process proceeds to Step S108.

On the other hand, in a case where these eye behaviors are not observed or in a case where these eye behaviors are not observed sufficiently, the driver-alertness deciding section 65 decides that the alertness of the driver is low, and is not at a level sufficient for execution of manual driving.

In this case, the decision in Step S107 is No, and the process proceeds to Step S109.

(Step S108)

In a case where it is decided, in Step S107, that the alertness of the driver is high, and is at a level sufficient for execution of manual driving, it is decided, in Step S108, that the alertness evaluation is passed, and it is permitted to return to manual driving.

(Step S109)

On the other hand, in a case where it is decided, in Step S107, that the alertness of the driver is low, and is not at a level sufficient for execution of manual driving, it is decided, in Step S109, whether or not the upper limit of the number of times of retrying of the alertness deciding process specified in advance is reached.

In a case where the upper limit is not reached, the process proceeds to Step S104. In this case, new display information (problem) is presented, and the process of observing eye behaviors of the driver is executed again.

On the other hand, in a case where the upper limit is reached, the process proceeds to Step S110.

(Step S110)

In a case where it is decided, in Step S109, that the upper limit of the number of times of retrying of the alertness deciding process specified in advance is reached, the process in Step S110 is executed.

In this case, it is decided, in Step S110, that the alertness evaluation is not passed, that is, it is not possible to confirm that the driver has alertness sufficient to return to manual driving, and the process is ended. In this case, it is not permitted to return to manual driving, and the automobile performs a process, such as an emergency stop, to avoid the entrance to a manual driving zone.

In such a manner, the information processing apparatus according to the present disclosure presents a visual problem to the driver before a return to manual driving, and analyzes eye behaviors of the driver that occur at the time of solving the problem. Specifically, by generating and presenting nonuniform problems that are expected to trigger, as eye behaviors of the driver, particular eye behaviors such as a saccade (eye rotation), a fixation, or a microsaccade (eye microrotation) for problem solving, eye behaviors that actually occur at the time when the driver responds to a problem are observed. On the basis of training dictionary characteristics of the driver, estimation of the internal alertness level of the driver is performed every time an eye behavior is observed, and it is decided whether or not the internal alertness state in the brain is sufficient for starting a return to manual driving.

In a case where it is decided from the analyses of these eye behaviors that the driver has sufficiently made a return to the alertness, it is decided that the driver has alertness high enough for manual driving, and it is permitted to start manual driving.

On the other hand, in a case where it is decided that those eye behaviors are not occurring sufficiently, it is decided that the driver does not have alertness high enough for manual driving, and it is not permitted to start manual driving. In this case, an emergency pulling-over process such as a process of stopping before the entrance into the manual driving zone is performed.

Processes regarding actual problems from checking visual information until reaching the answers to the problems differ significantly in some cases depending on individual characteristics, and are influenced by various factors such as the state of the driver at that time, the implementation state of repetition of identical problems, action characteristics of checking questions after looking at answer choices, fatigue, sight and fatigue of sight at that time, disturbance by external light, or mental wandering. Accordingly, in order to perform decisions highly precisely, it is preferred to use driver-specific return prediction dictionary data generated by training processes about the return quality at the time of execution of transfer that occur on each occasion in long-term repetitive use (normal returns, delayed returns, return abandonment, handling of emergency by the system) and the like.

It is desirable to execute a normal return prediction on the basis of a result of an analysis of behavioral characteristics of eyes by using driver-specific return prediction dictionary data. By these processes, it becomes possible to start safe manual driving.

While only the analysis of eye behaviors is described here, in a preferred configuration, input data to the process of deciding whether or not the driver is in a state in which he/she can start safe manual driving, and the learner described above includes the states and history information of user's vehicle information, road environment information, and driver vital signals obtained by the data acquiring section 102 mentioned below.

As mentioned above, the configuration according to the present disclosure makes it possible to decide whether or not the driver of the moving apparatus that can be driven in a driving mode that can be switched to automated driving and manual driving has alertness sufficient to return to manual driving on the basis of eye behaviors of the driver.

Note that, while the return to the internal alertness in the brain of the driver is decided at the time of transfer from automated driving to manual driving in the embodiments mentioned above, the technique of analyzing eye behaviors makes it possible to analyze externally observable reflections of the brain activity of a subject, and can be used variously for purposes other than deciding the driver state at the time of transfer from automated driving to manual driving.

The eye behavioral analysis technique mentioned above observes a result of a correlation between a problem and memory information, and can be used variously by observing and deciding reactions to presented problems.

If a problem presented to a subject is one that requires collation between the problem and memories of the subject, the process of obtaining the answer to the problem becomes one that reflects the state and mental state of the subject. Accordingly, the eye behavioral analysis technique can also be applied to authenticity decision of a respondent at the time of presentation of a problem at a report such as an alcohol drinking report or an overwork report, for example, and the like.

Further, problem presentation needs not be limited to the operation of vehicles. For example, the use of problem presentation can also be expanded to a wide variety of events and occupations such as aircraft operation, train operation, crane manipulation, air traffic controller, or remote automated driving controller, and further to others such as authenticity evaluation by psychological analysis at the time of self-report.

Note that it is known that the superior temporal sulcus of the temporal lobe becomes active when a subject selects visual information that is required to solve some kind of problem, the interparietal sulcus becomes active when attention is paid to the visual information, and the front-orbital area becomes active when the eyes are moved. In addition, the hippocampus inside the temporal lobe works when one remembers things from memories. In addition, it is also known that, in a case where the suppression of stimulus reflexes due to an abnormal condition, such as dysautonomia, of the mutual balance between what is called the sympathetic nerve system and parasympathetic nerve system occurs, eye behaviors change. Accordingly, the eye behavioral analysis process according to the present disclosure can be used as processes for examination and monitoring of mental health of a subject such as a driver. Specifically, for example, by using the eye behavioral analysis process for grasping the states of drivers of transportation service vehicles such as buses or taxis, and managing the health of the drivers, it is possible to enable safe operation.

[7. About Specific Configuration and Process Examples of Moving Apparatus]

Next, the specific configuration and process examples of the moving apparatus according to the present disclosure are explained with reference to FIG. 27 and the subsequent figures.

Figure 27:
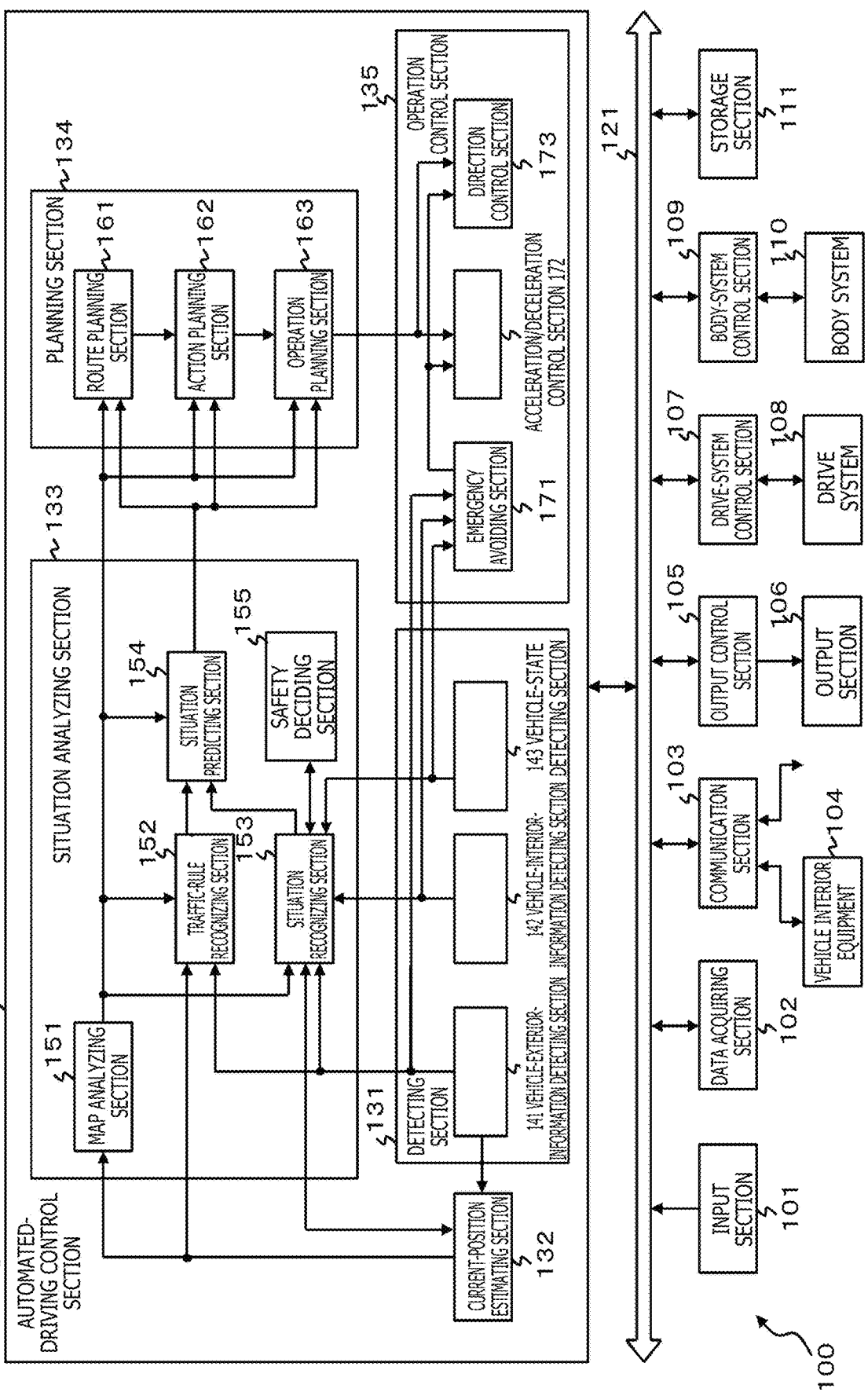
FIG. 27 is a figure for explaining a configuration example of the moving apparatus according to the present disclosure.

FIG. 27 depicts a configuration example of a moving apparatus 100. Note that, in the following, in a case where a vehicle provided with the moving apparatus 100 and other vehicles are distinguished from each other, the former is referred to as a user's automobile or a user's vehicle.

The moving apparatus 100 includes an input section 101, the data acquiring section 102, a communication section 103, vehicle interior equipment 104, an output control section 105, an output section 106, a drive-system control section 107, a drive system 108, a body-system control section 109, a body system 110, a storage section 111, and an automated-driving control section 112.

The input section 101, the data acquiring section 102, the communication section 103, the output control section 105, the drive-system control section 107, the body-system control section 109, the storage section 111, and the automated-driving control section 112 are interconnected via a communication network 121. The communication network 121 includes an in-vehicle communication network, a bus, or the like conforming to a certain standard such as a CAN (Controller Area Network), LIN (Local Interconnect Network), a LAN (Local Area Network), or FlexRay (registered trademark), for example. Note that sections of the moving apparatus 100 are connected directly without using the communication network 121 in some cases.

Note that, in the following, in a case where sections of the moving apparatus 100 perform communication via the communication network 121, descriptions about the communication network 121 are omitted. For example, in a case where the input section 101 and the automated-driving control section 112 perform communication via the communication network 121, it is described simply that the input section 101 and the automated-driving control section 112 perform communication.

The input section 101 includes an apparatus used by a passenger to input various types of data, instructions, and the like. For example, the input section 101 includes manipulation devices such as a touch panel, buttons, a microphone, switches, or levers; manipulation devices by which information can be input by a method other than manual manipulation, by sounds, gestures, or the like; and the like. In addition, for example, the input section 101 may be a remote-control apparatus that uses infrared rays or other radio waves, or externally-connected equipment such as mobile equipment or wearable equipment that supports manipulation of the moving apparatus 100. The input section 101 generates an input signal on the basis of data, an instruction, or the like input by a passenger, and supplies the input signal to sections of the moving apparatus 100.

The data acquiring section 102 includes various types of sensors and the like that acquire data used for processes by the moving apparatus 100, and supplies the acquired data to sections of the moving apparatus 100.

For example, the data acquiring section 102 includes various types of sensors for detecting the state of the user's automobile, and the like. Specifically, for example, the data acquiring section 102 includes a gyro sensor; an acceleration sensor; an inertial measurement unit (IMU); sensors for detecting an accelerator pedal manipulation amount, a brake pedal manipulation amount, a steering wheel steering angle, an engine revolution speed, a motor revolution speed, a wheel rotation speed and the like; and the like.

In addition, for example, the data acquiring section 102 includes various types of sensors for detecting information regarding the outside of the user's automobile. Specifically, for example, the data acquiring section 102 includes a ToF (Time Of Flight) camera, a stereo camera, a monocular camera, an infrared camera, and another image capturing unit such as a camera. In addition, for example, the data acquiring section 102 includes an environment sensor for detecting weather conditions, atmospheric phenomena, or the like and an ambient information detection sensor for detecting objects around the user's automobile. The environment sensor includes a raindrop sensor, a fog sensor, a sunshine sensor, a snow sensor, and the like, for example. The ambient information detection sensor includes an ultrasonic sensor, a radar, a LiDAR (Light Detection and Ranging, Laser Imaging Detection and Ranging), a sonar, and the like, for example.

Figure 28:
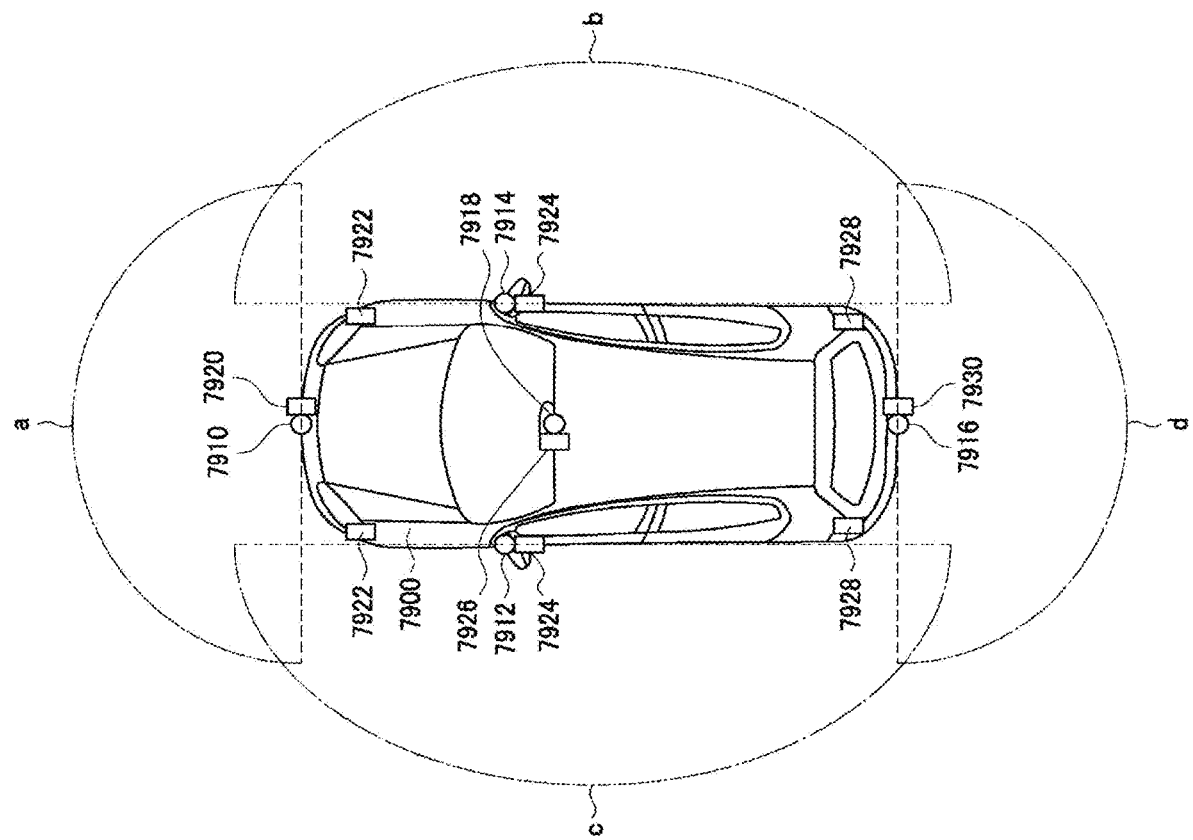
FIG. 28 is a figure for explaining a configuration example of the moving apparatus according to the present disclosure.

For example, FIG. 28 depicts an installation example of various types of sensors for detecting information outside the user's automobile. Image capturing apparatuses 7910, 7912, 7914, 7916, and 7918 are provided at at least one position of, for example, a front nose, side mirrors, a rear bumper, and a back door of a vehicle 7900 and an upper section of the windshield in the interior of the vehicle.

The image capturing unit 7910 provided at the front nose and the image capturing unit 7918 provided at the upper section of the windshield in the interior of the vehicle mainly acquire images of the space in front of the vehicle 7900. The image capturing units 7912 and 7914 provided at the side mirrors mainly acquire images of the spaces on the sides of the vehicle 7900. The image capturing unit 7916 provided at the rear bumper or the back door mainly acquires images of the space behind the vehicle 7900. The image capturing unit 7918 provided at the upper section of the windshield in the interior of the vehicle is mainly used for detection of preceding vehicles, pedestrians, obstacles, traffic lights, traffic signs, lanes, and the like. In addition, in automated driving in the coming future, their use may be expanded to cover wider ranges at the time when the vehicle makes a right or left turn, and to cover pedestrians who are crossing the road ahead when the vehicle makes a right or left turn, and further to cover the ranges of objects approaching crosswalks.

Note that FIG. 28 depicts one example of the image capturing ranges of the image capturing units 7910, 7912, 7914, and 7916. An image-capturing range a represents the image-capturing range of the image capturing unit 7910 provided at the front nose, image-capturing ranges b and c represent the image-capturing ranges of the image capturing units 7912 and 7914 provided at the side mirrors, and an image-capturing range d represents the image-capturing range of the image capturing unit 7916 provided at the rear bumper or the back door. For example, by superimposing data of images captured by the image capturing units 7910, 7912, 7914, and 7916, a bird's-eye view image of the vehicle 7900 as viewed from above, further an all-around stereoscopic display image surrounding the periphery of the vehicle with a curved plane, and the like are obtained.

Sensors 7920, 7922, 7924, 7926, 7928, and 7930 provided at the front, rear, sides, and corners of the vehicle 7900, and the upper section of the windshield in the interior of the vehicle may be ultrasonic sensors or radars, for example. Sensors 7920, 7926, and 7930 provided at the front nose, rear bumper, and back door of the vehicle 7900 and the upper section of the windshield interior of the vehicle may be LiDARs, for example. These sensors 7920 to 7930 are mainly used for detection of preceding vehicles, pedestrians, obstacles, and the like. Results of the detection may further be applied for improvement of the stereoscopic display of the bird's-eye view display or all-around stereoscopic display.

Returning to FIG. 27, the explanation of constituent elements is continued. The data acquiring section 102 includes various types of sensors for detecting the current position of the user's automobile. Specifically, for example, the data acquiring section 102 includes a GNSS (Global Navigation Satellite System) receiver that receives GNSS signals from GNSS satellites, and the like.

In addition, for example, the data acquiring section 102 includes various types of sensors for detecting information of the interior of the vehicle. Specifically, for example, the data acquiring section 102 includes an image capturing unit that captures images of the driver, a vital sensor that detects vital information of the driver, a microphone that collects sounds in the interior of the vehicle, and the like. For example, the vital sensor is provided on a seat surface, a steering wheel, or the like, and detects the seated state of a passenger sitting on the seat, or vital information of the driver holding the steering wheel. Vital signals that can be used include various observable data such as heart rate, pulse rate, blood flow, respiration, psychosomatic correlation, visual stimulus, brain waves, sweating state, head posture behavior, eyes, steady gaze, blinking, saccade, microsaccade, fixation, drift, gaze, or iris pupil reaction.

The vital activity observable information reflecting observable driving states is aggregated as observable evaluation values estimated from observation, and is used for a computation of a return notification timing at a safety deciding section 155 mentioned below as return-delay-case-specific characteristics of the corresponding driver from return-delay-time characteristics associated with the log of the evaluation values.

Further, it is used for a decision of the alertness of the driver, and is also used for the decision process as to whether or not to permit a return to manual driving on the basis of a result of the alertness decision.

The communication section 103 communicates with the vehicle interior equipment 104 and various pieces of equipment, servers, base stations, and the like outside the vehicle, transmits data supplied from sections of the moving apparatus 100, and supplies received data to sections of the moving apparatus 100. Note that communication protocols supported by the communication section 103 are not particularly limited, and it is also possible for the communication section 103 to support plural types of communication protocols.

For example, the communication section 103 performs wireless communication with the vehicle interior equipment 104 by a wireless LAN, Bluetooth (registered trademark), NFC (Near Field Communication), a WUSB (Wireless USB), and the like. In addition, for example, the communication section 103 performs wired communication with the vehicle interior equipment 104 via connection terminals (and cables if necessary), which are not depicted, by a USB (Universal Serial Bus), an HDMI (registered trademark) (High-Definition Multimedia Interface), an MHL (Mobile High-definition Link), and the like.

Further, for example, the communication section 103 communicates with equipment (e.g., application servers or control servers) on external networks (e.g., the Internet, cloud networks, or business-operator-specific networks) via base stations or access points. In addition, for example, the communication section 103 communicates with terminals (e.g., terminals of pedestrians or stores, or MTC (Machine Type Communication) terminals) that are near the user's automobile by using a P2P (Peer To Peer) technology.

Further, for example, the communication section 103 performs V2X communication such as vehicle to vehicle communication, vehicle to infrastructure communication, vehicle to home communication, or vehicle to pedestrian communication. In addition, for example, the communication section 103 includes a beacon receiving section, receives radio waves or electromagnetic waves emitted from wireless stations and the like installed on roads, and acquires information regarding the current position traffic jams, traffic regulations, required time, and the like. Note that the communication section may be used to perform pairing with vehicles that are in front of the user's vehicle driving in zones that can be a leading vehicle, and information acquired from data acquiring section mounted on a forward vehicle may be acquired as prior driving information, and used to complement data of the data acquiring section 102 of the user's automobile.

Particularly, this serves as means for ensuring the higher safety for following vehicles when those vehicles are driving in a line led by a leading automobile, or in another similar situation.

For example, the vehicle interior equipment 104 includes mobile equipment (a tablet, a smartphone, etc.) or wearable equipment carried by a passenger, information equipment that is carried into or attached to the user's automobile, a navigation apparatus that performs route searches to certain destinations, and the like. Note that, considering that occupants will not necessarily be fixed to seating fixed positions if automated driving is used more widely, in the future, the vehicle interior equipment 104 that can be used may be expanded to a video player, a gaming console, and other equipment that can be used attachably to and detachably from an installation position in the vehicle. While information presentation about a geographical point where the intervention by the driver becomes necessary is performed only to the corresponding driver in the example described in the present embodiment, the information provision may be performed further to a following vehicle when the vehicles are driving in a line or in another similar situation, and further by always providing information to an operation management center for passenger transportation shared buses and long-distance logistics commercial vehicles, it may be used in combination with remote drive assistance as appropriate.

The output control section 105 controls output of various types of information to passengers of the user's automobile or to the outside of the vehicle. For example, the output control section 105 generates output signals including at least one of visual information (e.g., image data) and auditory information (e.g., sound data), and supplies them to the output section 106, to thereby control output of visual information and auditory information from the output section 106. Specifically, for example, the output control section 105 synthesizes data of images captured by different image capturing units of the data acquiring section 102, generates a bird's-eye view image, a panoramic image, or the like, and supplies output signals including the generated image to the output section 106. In addition, for example, the output control section 105 generates sound data including a beep, a warning message, or the like about a danger such as collision, contact, or entrance into a danger zone, and supplies output signals including the generated sound data to the output section 106.

The output section 106 includes an apparatus that can output visual information or auditory information to passengers of the user's automobile or to the outside of the vehicle. For example, the output section 106 includes a display apparatus, an instrument panel, an audio speaker, headphones, a wearable device such as an eye-glass-type display worn by a passenger, a projector, a lamp, and the like. Other than an apparatus having a normal display, for example, the display apparatus included in the output section 106 may be an apparatus that displays visual information within the visual field of the driver such as a head-up display, a transmission display, or an apparatus having an AR (Augmented Reality) display functionality.

The drive-system control section 107 generates various types of control signals, and supplies them to the drive system 108, to thereby perform control of the drive system 108. In addition, as necessary, the drive-system control section 107 supplies the control signals to sections other than the drive system 108, and gives notification of the control state of the drive system 108, and the like.

The drive system 108 includes various types of apparatuses related to the drive system of the user's automobile. For example, the drive system 108 includes a driving force generating apparatus such as an internal combustion engine or a drive motor for generating driving force, a driving force transmission mechanism for transmitting the driving force to wheels, a steering mechanism that adjusts the steering angle, a braking apparatus that generate braking force, an ABS (Antilock Brake System), an ESC (Electronic Stability Control), an electric power steering apparatus, and the like.

The body-system control section 109 generates various types of control signals, and supplies them to the body system 110, to thereby perform control of the body system 110. In addition, as necessary, the body-system control section 109 supplies the control signals to sections other than the body system 110, and gives notification of the control state about the body system 110, and the like.

The body system 110 includes various types of apparatuses related to the body system mounted on the machine body. For example, the body system 110 includes a key-less entry system, a smart key system, a power window apparatus, power seats, a steering wheel, an air-conditioning apparatus, various types of lamps (e.g., head lamps, back lamps, brake lamps, blinkers, fog lamps, etc.), and the like.

For example, the storage section 111 includes magnetic storage devices such as a ROM (Read Only Memory), a RAM (Random Access Memory), or an HDD (Hard Disc Drive), a semiconductor storage device, an optical storage device, a magneto-optical storage device, and the like. The storage section 111 stores various types of programs, data, and the like used by sections of the moving apparatus 100. For example, the storage section 111 stores map data such as a three-dimensional high-precision map such as a dynamic map, a global map that has precision lower than that of the high-precision map but covers a large area, or a local map including information regarding the area around the user's automobile.

The automated-driving control section 112 performs control related to automated driving such as autonomous driving or driving assistance. Specifically, for example, the automated-driving control section 112 performs coordinated control for the purpose of the realization of functionalities of an ADAS (Advanced Driver Assistance System) including collision avoidance or impact mitigation of the user's automobile, following driving based on inter-vehicle distances, vehicle speed maintenance driving, collision warning of the user's automobile, lane deviation warning of the user's automobile, or the like. In addition, for example, the automated-driving control section 112 performs coordinated control for the purpose of automated driving of autonomously driving without being dependent on manipulation by the driver, and the like. The automated-driving control section 112 includes a detecting section 131, a current-position estimating section 132, a situation analyzing section 133, a planning section 134, and an operation control section 135.

The detecting section 131 performs detection of various types of information necessary for control of automated driving. The detecting section 131 includes a vehicle-exterior-information detecting section 141, a vehicle-interior-information detecting section 142, and a vehicle-state detecting section 143.

The vehicle-exterior-information detecting section 141 performs a process of detecting information regarding the outside of the user's automobile on the basis of data or signals from sections of the moving apparatus 100. For example, the vehicle-exterior-information detecting section 141 performs processes of detecting, recognizing, and tracking objects around the user's automobile, and a process of detecting the distances to and relative speeds of the objects. For example, objects to be detection targets include vehicles, humans, obstacles, structures, roads, traffic lights, traffic signs, road markings, and the like.

In addition, for example, the vehicle-exterior-information detecting section 141 performs a process of detecting environments around the user's automobile. For example, environments around the user's automobile to be detection targets include weather, temperature, humidity, brightness, the state of a road surface, and the like. The vehicle-exterior-information detecting section 141 supplies data representing results of the detection processes to the current-position estimating section 132, a map analyzing section 151, a traffic-rule recognizing section 152, and a situation recognizing section 153 of the situation analyzing section 133, an emergency avoiding section 171 of the operation control section 135, and the like.

Information acquired by the vehicle-exterior-information detecting section 141 can be supplied mainly by infrastructures if the user's automobile is driving in zones where local dynamic maps (LDMs) which are always updated are supplied from the infrastructures, as zones where it is prioritized to allow automated driving. Alternatively, in some other possible cases, the user's automobile may drive while always receiving updated information in advance before entering the zones from vehicles or a vehicle group driving the corresponding zones earlier. In addition, in a case where latest local dynamic maps are not always updated by infrastructures or in other similar cases, for the purpose of obtaining road information immediately before an entrance zone for higher safety especially while driving in a line and so on, road environment information obtained from a leading vehicle having entered the zone may further be used complementarily. In many cases, whether automated driving is allowed in a zone is determined on the basis of whether or not there is the prior information provided from infrastructures. An updated and fresh local dynamic map (LDM) included in information representing whether automated driving is allowed or not allowed on a route provided from an infrastructure is equivalent to providing an invisible trajectory as what is called "information." Note that, for convenience, the vehicle-exterior-information detecting section 141 is depicted as being mounted on the user's vehicle as a premise, but the prior predictability at the time of driving may be enhanced further by using information captured as "information" by front vehicles.

The vehicle-interior-information detecting section 142 performs a process of detecting information regarding the interior of the vehicle on the basis of data or signals from sections of the moving apparatus 100. For example, the vehicle-interior-information detecting section 142 performs processes of identifying and recognizing the driver, a process of detecting the state of the driver, a process of detecting a passenger, a processing of detecting environments of the interior of the vehicle, and the like. For example, the state of the driver to be detection targets includes physical condition, alertness, concentration, fatigue, line-of-sight direction, detailed eye behaviors, and the like.

Further, it is expected that in the future use of automated driving, the driver is completely disengaged from the driving steering work, the driver drowses temporarily, or starts working on other tasks, and it becomes necessary for a system to grasp to what extent a return to the alertness of the consciousness necessary for a return to driving has been made. That is, in driver monitoring systems that have conventionally been considered, detection means are mainly responsible for detecting a decline in consciousness such as sleepiness, but in the coming future, the driver will not intervene in the driving steering at all. Accordingly, a system will no longer have means for directly observing the degree of intervention by the driver in driving from the steering stability of steering equipment or the like, and it is necessary for the system to observe the transition of a return to consciousness necessary for driving from a state in which the accurate consciousness state of the driver is unknown, and proceed with intervention transfer from automated driving to manual driving of steering by grasping the accurate internal alertness state of the driver.

In view of this, the vehicle-interior-information detecting section 142 mainly has roles at two major stages. The first role is passive monitoring of the driver during automated driving, and the second role is detection determination of the periphery cognition, perception, determination, and further, a steering-equipment actuation ability of the driver until, after a return request is given from the system, a level is reached at which the driver is capable of manual driving before the arrival at a zone of driving under the care of the driver. As control, self-diagnosis of malfunctions of the entire vehicle may be performed further, and similarly in a case where lowering of the automated driving functionality has occurred due to a partial functionality malfunction of the automated driving also, an early return to manual driving by the driver may be prompted. Passive monitoring mentioned here means detection means of a type that does not ask a driver to respond and react consciously, and does not exclude an object that emits physical radio waves, light, or the like from equipment, and detects a response signal. That is, passive methods mean state monitoring of the driver who is unconscious while taking a nap, and so on, and involve classification not of cognitive responses and reactions of the driver. It does not exclude an active response device that analyzes and evaluates reflected or diffused signals as a result of emission of radio waves, infrared rays, or the like. On the contrary, monitoring that asks the driver to respond consciously with responses and reactions is called active monitoring.

For example, environments of the interior of the vehicle to be detection targets include temperature, humidity, brightness, smell, and the like. The vehicle-interior-information detecting section 142 supplies data representing results of the detection processes to the situation recognizing section 153 of the situation analyzing section 133 and the operation control section 135. Note that, in a case where it is found that manual driving by the driver will not be able to be achieved within the right time period after an instruction for a return to driving is given by the system to the driver and it is determined that the transfer will be too late even if it is attempted to make extra time by performing deceleration control while staying in automated driving, an instruction is given to the emergency avoiding section 171 or the like of the system to start a procedure for decelerating, pulling over, and stopping for pulling over the vehicle. That is, also in a situation as the initial state in which it will be too late similarly, time until arrival within which the transfer is allowed to proceed can be made longer by decelerating the vehicle early. By making the time until arrival within which the transfer is allowed to proceed longer, spare time is generated for handling of events by the system, and it becomes possible to take measures for ensuring safety. It should be noted, however, that the application of this is restricted because, as mentioned below, excessively decelerating or slowing down the automobile increases traffic-jam triggering factors and the risk of rear-end collisions.

The vehicle-state detecting section 143 performs a process of detecting the state of the user's automobile on the basis of data or signals from sections of the moving apparatus 100. For example, the state of the user's automobile to be detection targets includes speed, acceleration, steering angle, whether or not there are abnormalities, contents of abnormalities, the state of driving manipulation, the position and inclination of power seats, the state of door locks, the state of other in-vehicle equipment, and the like. The vehicle-state detecting section 143 supplies data representing results of the detection processes to the situation recognizing section 153 of the situation analyzing section 133, the emergency avoiding section 171 of the operation control section 135, and the like.

On the basis of data or signals from sections of the moving apparatus 100 such as the vehicle-exterior-information detecting section 141 and the situation recognizing section 153 of the situation analyzing section 133, the current-position estimating section 132 performs a process of estimating the position and posture of the user's automobile, and the like. In addition, as necessary, the current-position estimating section 132 generates a local map (hereinafter, referred to as a map for current position estimation) used for estimating the current position.

For example, the map for current position estimation is a highly precise map using a technology such as SLAM (Simultaneous Localization and Mapping). The current-position estimating section 132 supplies data representing results of the estimation processes to the map analyzing section 151, the traffic-rule recognizing section 152, and the situation recognizing section 153 of the situation analyzing section 133, and the like. In addition, the current-position estimating section 132 causes the storage section 111 to store the map for current position estimation.

The situation analyzing section 133 performs a process of analyzing the situation of and around the user's automobile. The situation analyzing section 133 includes the map analyzing section 151, the traffic-rule recognizing section 152, the situation recognizing section 153, a situation predicting section 154, and the safety deciding section 155.

While using data or signals from sections of the moving apparatus 100 such as the current-position estimating section 132 or the vehicle-exterior-information detecting section 141 as necessary, the map analyzing section 151 performs a process of analyzing various types of maps stored in the storage section 111, and constructs a map including information necessary for processes of automated driving. The map analyzing section 151 supplies the constructed map to the traffic-rule recognizing section 152, the situation recognizing section 153, the situation predicting section 154, a route planning section 161, an action planning section 162, and an operation planning section 163 of the planning section 134, and the like.

On the basis of data or signals from sections of the moving apparatus 100 such as the current-position estimating section 132, the vehicle-exterior-information detecting section 141, or the map analyzing section 151, the traffic-rule recognizing section 152 performs a process of recognizing traffic rules around the user's automobile. By this recognition process, for example, the positions and states of signals around the user's automobile, the contents of traffic regulations around the user's automobile, lanes on which the user's automobile is allowed to drive, and the like are recognized. The traffic-rule recognizing section 152 supplies data representing results of the recognition process to the situation predicting section 154 and the like.

On the basis of data or signals from sections of the moving apparatus 100 such as the current-position estimating section 132, the vehicle-exterior-information detecting section 141, the vehicle-interior-information detecting section 142, the vehicle-state detecting section 143, or the map analyzing section 151, the situation recognizing section 153 performs a process of recognizing the situation related to the user's automobile. For example, the situation recognizing section 153 performs a process of recognizing the situation of the user's automobile, the situation around the user's automobile, the situation of the driver of the user's automobile, and the like. In addition, the situation recognizing section 153 generates a local map (hereinafter, referred to as a map for situation recognition) to be used for recognition of the situation around the user's automobile, as necessary. The map for situation recognition is an occupancy grip map, for example.

For example, the situation of the user's automobile to be recognition targets includes the position, posture and movement (e.g., speed, acceleration, moving direction, etc.) of the user's automobile; vehicle-specific and further cargo-loading-specific situations that determine motion characteristics of the user's automobile such as a cargo loading amount, the movement of the center of gravity of the vehicle body due to cargo loading, tire pressure, the braking distance movement due to the wear conditions of braking pads, permitted maximum deceleration braking to prevent cargo movement caused to load braking, the centrifugal-force-reduction limit speed when driving on a curve with a liquid load, or the like; and road-specific situations such as the frictional coefficient of a road surface, the curve of a road, or the slope of a road. Because even if the road environment is totally the same, a return start timing that is required for control varies depending on characteristic of the vehicle itself, further loads, and the like, it is necessary to make an optimum timing for performing control reflect those various conditions by collecting and learning the various conditions. When determining a control timing on the basis of the type and load of the vehicle, it is not sufficient to simply observe and monitor whether or not there are abnormalities of the user's vehicle, the contents of abnormalities, and the like. Parameters that determine additional extra time until return that is desirable for ensuring a certain level of safety may be set as fixed values in advance according to load-specific characteristics in the logistics industry and the like, and a method in which all the notification timing determination conditions are set uniformly by self-accumulative learning may not be adopted necessarily.

For example, the condition around the user's automobile to be recognition targets include the types and positions of surrounding stationary objects; the types, positions, and motions of surrounding moving objects (e.g., speed, acceleration, moving direction, etc.); the configurations and surface states of surrounding roads; the weather, temperature, humidity, and brightness of the space around the user's automobile; and the like. For example, the state of the driver to be recognition targets includes physical condition, alertness, concentration, fatigue, motion of a line of sight, driving manipulation, and the like. For safe driving of the vehicle, there are significantly different control start points at which handlings are required, according to different vehicle-specific states such as a loading amount, a chassis-fixed-state of a mounting section, a center-of-gravity biased state, a maximum deceleration possible acceleration value, a maximum load possible centrifugal force, a return response delay amount according to the state of the driver, and the like.

The situation recognizing section 153 supplies data representing results of the recognition process (including the map for situation recognition, as necessary) to the current-position estimating section 132, the situation predicting section 154, and the like. In addition, the situation recognizing section 153 causes the storage section 111 to store the map for situation recognition.

On the basis of data or signals from sections of the moving apparatus 100 such as the map analyzing section 151, the traffic-rule recognizing section 152, or the situation recognizing section 153, the situation predicting section 154 performs a process of predicting the situation related to the user's automobile. For example, the situation predicting section 154 performs a process of predicting the situation of the user's automobile, the situation around the user's automobile, the situation of the driver, and the like.

For example, the situation of the user's automobile to be prediction targets include the behavior of the user's automobile, the occurrence of an abnormality, the drivable distance, and the like. For example, the situations around the user's automobile to be prediction targets include the behaviors of moving objects around the user's automobile, changes of the states of signals, changes of the environment such as weather, and the like. For example, the situations of the driver to be prediction targets include behaviors and the physical condition of the driver, and the like.

The situation predicting section 154 supplies data representing results of the prediction process to the route planning section 161, the action planning section 162, and the operation planning section 163 of the planning section 134, and the like, along with the data from the traffic-rule recognizing section 152 and the situation recognizing section 153.

The safety deciding section 155 learns optimum return timings according to return action patterns of the driver, vehicle characteristics, and the like, and provides the learned information to the situation recognizing section 153 and the like. Thereby, for example, it becomes possible to present, to the driver, a statistically-determined optimum timing necessary for the driver to normally return to manual driving from automated driving at a certain preset ratio or higher.

On the basis of data or signals of sections of the moving apparatus 100 such as the map analyzing section 151 or the situation predicting section 154, the route planning section 161 plans a route to a destination. For example, on the basis of a global map, the route planning section 161 sets a route from the current position to a specified destination. In addition, for example, the route planning section 161 changes the route as appropriate on the basis of a traffic jam, an accident, traffic regulations, conditions such as engineering work, the physical condition of the driver, and the like. The route planning section 161 supplies data representing the planned route to the action planning section 162 and the like.

On the basis of data or signals from sections of the moving apparatus 100 such as the map analyzing section 151 or the situation predicting section 154, the action planning section 162 plans actions of the user's automobile for driving a route planned by the route planning section 161 safely within a planned length of time. For example, the action planning section 162 plans starts, stops, advancing directions (e.g., moving forward, moving backward, turning left, turning right, changing directions, etc.), driving lanes, driving speeds, passing other vehicles, and the like. The action planning section 162 supplies data representing the planned actions of the user's automobile to the operation planning section 163 and the like.

On the basis of data or signals from sections of the moving apparatus 100 such as the map analyzing section 151 or the situation predicting section 154, the operation planning section 163 plans operation of the user's automobile for realizing actions planned by the action planning section 162. For example, the operation planning section 163 plans acceleration, deceleration, driving trajectories, and the like. The operation planning section 163 supplies data representing the planned operation of the user's automobile to an acceleration/deceleration control section 172 and a direction control section 173 of the operation control section 135, and the like.

The operation control section 135 performs control of the operation of the user's automobile. The operation control section 135 includes the emergency avoiding section 171, the acceleration/deceleration control section 172, and the direction control section 173.

On the basis of detection results of the vehicle-exterior-information detecting section 141, the vehicle-interior-information detecting section 142, and the vehicle-state detecting section 143, the emergency avoiding section 171 performs a process of detecting emergencies such as collision, contact, entrance into a danger zone, an abnormality of the driver, or an abnormality of the vehicle. In a case where the occurrence of an emergency is detected, the emergency avoiding section 171 plans operation of the user's automobile for avoiding the emergency, such as a sudden stop or a quick turn. The emergency avoiding section 171 supplies data representing the planned operation of the user's automobile to the acceleration/deceleration control section 172, the direction control section 173, and the like.

The acceleration/deceleration control section 172 performs acceleration/deceleration control for realizing the operation of the user's automobile planned by the operation planning section 163 or the emergency avoiding section 171. For example, the acceleration/deceleration control section 172 calculates a control target value of a driving force generating apparatus or a braking apparatus for realizing the planned acceleration, deceleration, or sudden stop, and supplies a control command representing the calculated control target value to the drive-system control section 107. Note that there are two main cases in which an emergency can occur. That is, one of them is a case where, during automated driving on a road that originally is indicated as a safe road by a local dynamic map or the like acquired from an infrastructure on a driving route during automated driving, an unpredicted accident occurs due to a sudden reason, and an emergency return of the driver will be too late. The other case is a case where it becomes difficult for the driver to rightly return to manual driving from automated driving.

The direction control section 173 performs direction control for realizing operation of the user's automobile planned by the operation planning section 163 or the emergency avoiding section 171. For example, the direction control section 173 calculates a control target value of a steering mechanism for realizing a driving trajectory or a quick turn planned by the operation planning section 163 or the emergency avoiding section 171, and supplies a control command representing the calculated control target value to the drive-system control section 107.

[8. About Configuration Example of Information Processing Apparatus]

While the processes mentioned above can be executed by applying the configuration of the moving apparatus explained with reference to FIG. 27, some of the processes can be executed in the information processing apparatus that is attachable to and detachable from the moving apparatus, for example.

Figure 29:
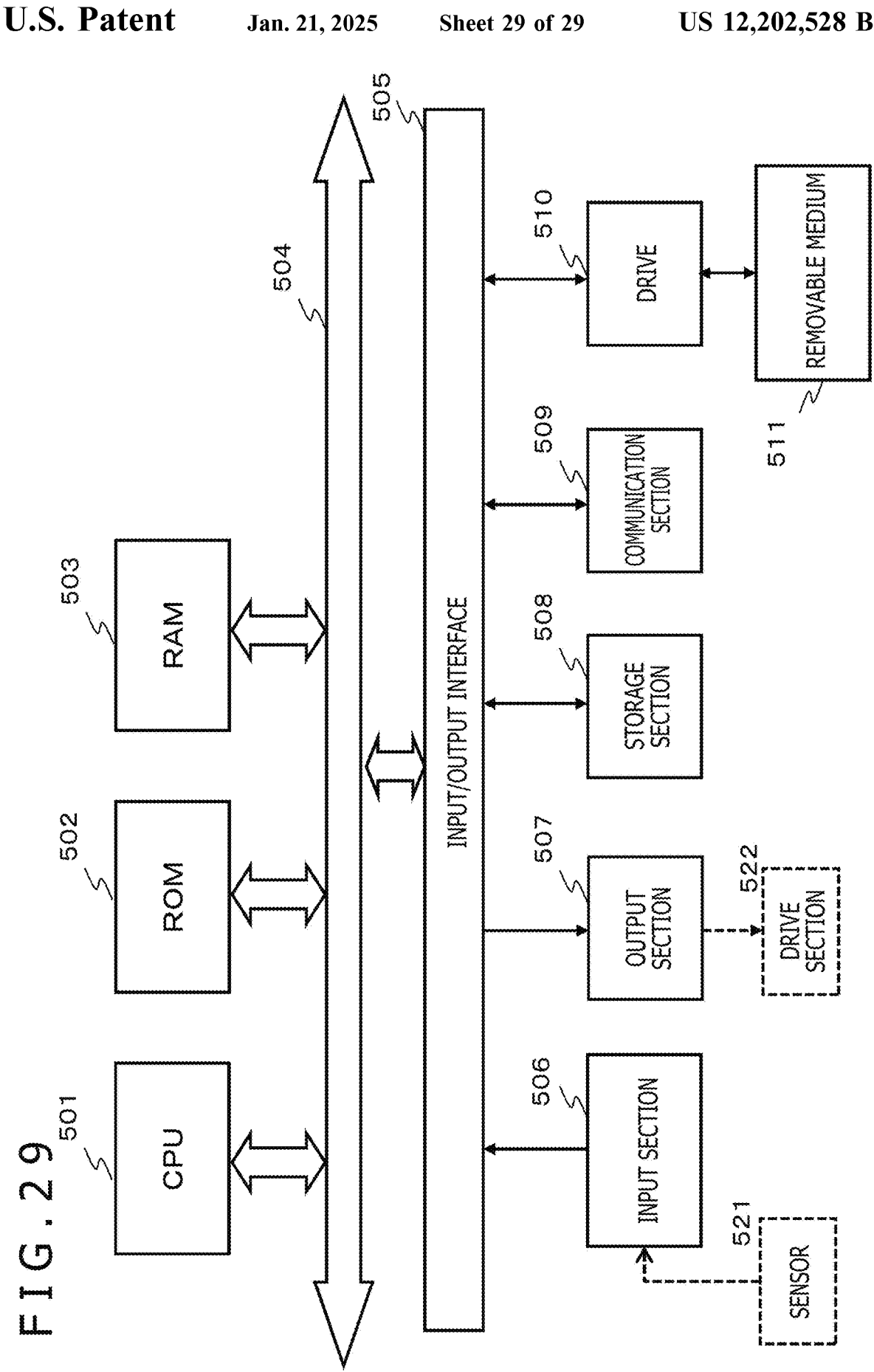
FIG. 29 is a figure for explaining a hardware configuration example of the information processing apparatus.

With reference to FIG. 29, a hardware configuration example of such an information processing apparatus is explained.

FIG. 29 is a figure depicting a hardware configuration example of the information processing apparatus.

A CPU (Central Processing Unit) 501 functions as a data processing section that executes various types of processes according to a program stored in a ROM (Read Only Memory) 502 or a storage section 508. For example, the CPU 501 executes processes according to the sequence explained in the embodiments mentioned above.

A RAM (Random Access Memory) 503 stores a program executed by the CPU 501, data, and the like. The CPU 501, the ROM 502, and the RAM 503 are interconnected by a bus 504.

The CPU 501 is connected to an input/output interface 505 via the bus 504, and the input/output interface 505 is connected with an input section 506 including various types of switches, a keyboard, a touch panel, a mouse, a microphone, and further a situation data acquiring section such as sensors, cameras, a GPS, and the like and an output section 507 including a display, a speaker, and the like.

Note that the input section 506 receives, as an input, input information from a sensor 521.

In addition, the output section 507 also outputs drive information for a drive section 522 of the moving apparatus.

The CPU 501 receives, as inputs, commands, situation data, and the like input from the input section 506, executes various types of processes, and outputs processing results to the output section 507, for example.

The storage section 508 connected to the input/output interface 505 includes a hard disk and the like, for example, and stores a program executed by the CPU 501, and various types of data. A communication section 509 functions as a transmitting/receiving section for data communication via a network such as the Internet or a local area network, and communicates with external apparatuses.

A drive 510 connected to the input/output interface 505 drives a magnetic disk, an optical disc, a magneto-optical disk, or a removable medium 511 such as a semiconductor memory such as a memory card, and executes recording or reading of data.

[9. Summary of Configuration According to Present Disclosure]

Thus far, embodiments according to the present disclosure are explained in detail with reference to particular embodiments. However, it is obvious that those skilled in the art can conceive of corrections or substitutions of embodiments within the scope not deviating from the gist of the present disclosure. That is, the present invention has been disclosed in exemplary forms, and should not be interpreted in a limited manner. To determine the gist of the present disclosure, the field of Claims should be taken into consideration.

Note that the technology disclosed in the present specification can have configuration like the ones mentioned below.

(1) An information processing apparatus including:

a display-information generating section that generates or acquires a problem and causes a display section to display the problem;

an eye-behavior analyzing section that analyzes an eye behavior of a user who observes the problem displayed on the display section; and an alertness deciding section that decides alertness of the user on the basis of a result of the analysis by the eye-behavior analyzing section.

(2) The information processing apparatus according to (1), in which the problem is a problem that requires work of additionally searching for missing information in order for the user to solve a problem.

(3) The information processing apparatus according to (1) or (2), in which the problem is a problem that triggers at least any one eye behavior of a saccade (eye rotation), a fixation, or a microsaccade (eye microrotation) of an eye as an eye behavior executed by the user to solve a problem.

(4) The information processing apparatus according to any one of (1) to (3), in which the eye-behavior analyzing section acquires data that allows a decision as to whether or not the user is executing an eye behavior for solving the problem.

(5) The information processing apparatus according to any one of (1) to (4), in which the eye-behavior analyzing section acquires data representing whether or not the user is executing at least any one eye behavior of a saccade (eye rotation), a fixation, or a microsaccade (eye microrotation) of an eye as an eye behavior for solving the problem.

(6) The information processing apparatus according to any one of (1) to (5), in which the alertness deciding section receives, as an input from the eye-behavior analyzing section, data that allows a decision as to whether or not the user is executing an eye behavior for solving the problem, and decides the alertness of the user on the basis of the input data.

(7) The information processing apparatus according to any one of (1) to (6), in which the alertness deciding section receives, as an input from the eye-behavior analyzing section, data representing whether or not the user is executing at least any one eye behavior of a saccade (eye rotation), a fixation, or a microsaccade (eye microrotation) of an eye, and decides the alertness of the user on the basis of the input data.

(8) The information processing apparatus according to any one of (1) to (7), in which the alertness deciding section decides that the alertness of the user is high in a case where an eye behavior of the user is decided as an eye behavior for solving the problem, and decides that the alertness of the user is low in a case where an eye behavior of the user is not decided as an eye behavior for solving the problem.

(9) The information processing apparatus according to any one of (1) to (8), in which the alertness deciding section decides that the alertness of the user is high in a case where it is decided that the user is executing at least any one eye behavior of a saccade (eye rotation), a fixation, or a microsaccade (eye microrotation) of an eye as an eye behavior for solving the problem.

(10) The information processing apparatus according to any one of (1) to (9), in which the alertness deciding section decides whether or not the user has alertness sufficient to execute manual driving.

(11) The information processing apparatus according to any one of (1) to (10), in which the problem generated or acquired by the display-information generating section is a problem that involves plural arrayed silhouettes representing objects and that requires a line-of-sight movement to each silhouette for problem solving.

(12) The information processing apparatus according to any one of (1) to (10), in which the problem generated or acquired by the display-information generating section is a problem that involves data of at least any one of arrayed characters, symbols, signs, or pictograms and that requires a line-of-sight movement to each piece of data for problem solving.

(13) A moving apparatus that is capable of being switched to automated driving and manual driving, the moving apparatus including:

a driver-information acquiring section that acquires driver information of a driver of the moving apparatus; and a data processing section that decides whether or not the driver has alertness sufficient to return to manual driving, on the basis of acquisition information of the driver-information acquiring section, in which the data processing section has a display-information generating section that generates or acquires a problem and causes a display section to display the problem, an eye-behavior analyzing section that analyzes an eye behavior of the driver who observes the problem displayed on the display section, and an alertness deciding section that decides alertness of the driver on the basis of a result of the analysis by the eye-behavior analyzing section.

(14) The moving apparatus according to (13), in which the alertness deciding section receives, as an input from the eye-behavior analyzing section, data that allows a decision as to whether or not the driver is executing an eye behavior for solving the problem, and decides, on the basis of the input data, whether or not the driver has alertness sufficient to return to manual driving.

(15) The moving apparatus according to (13) or (14), in which the alertness deciding section receives, as an input from the eye-behavior analyzing section, data representing whether or not the driver is executing at least any one eye behavior of a saccade (eye rotation), a fixation, or a microsaccade (eye microrotation) of an eye, and decides, on the basis of the input data, whether or not the driver has alertness sufficient to return to manual driving.

(16) The moving apparatus according to any one of (13) to (15), in which the control section of the moving apparatus permits a start of manual driving by the driver in a case where the alertness deciding section decides that the driver has alertness sufficient to return to manual driving, and the control section of the moving apparatus does not permit a start of manual driving by the driver and executes a process of avoiding an entrance into a manual driving zone in a case where the alertness deciding section decides that the driver does not have alertness sufficient to return to manual driving.

(17) An information processing method executed in an information processing apparatus, the information processing method including:

a display-information generating step, performed by a display-information generating section, of generating or acquiring a problem and causing a display section to display the problem;

an eye-behavior analyzing step, performed by an eye-behavior analyzing section, of analyzing an eye behavior of a user who observes the problem displayed on the display section; and an alertness deciding step, performed by an alertness deciding section, of deciding alertness of the user on the basis of a result of the analysis by the eye-behavior analyzing section.

(18) An information processing method executed in a moving apparatus, the moving apparatus being capable of being switched to automated driving and manual driving, the information processing method including:

a driver-information acquiring step, performed by a driver-information acquiring section, of acquiring driver information of a driver of the moving apparatus; and a data processing step, performed by a data processing section, of deciding whether or not the driver has alertness sufficient to return to manual driving, on the basis of the driver information, in which the data processing step includes a display-information generating step, performed by a display-information generating section, of generating or acquiring a problem and causing a display section to display the problem, an eye-behavior analyzing step, performed by an eye-behavior analyzing section, of analyzing an eye behavior of a user who observes the problem displayed on the display section, and an alertness deciding step, performed by an alertness deciding section, of deciding alertness of the user on the basis of a result of the analysis by the eye-behavior analyzing section.

(19) A program that causes an information processing apparatus to execute information processing including:

a display-information generating step of causing a display-information generating section to generate or acquire a problem and cause a display section to display the problem;

an eye-behavior analyzing step of causing an eye-behavior analyzing section to analyze an eye behavior of a user who observes the problem displayed on the display section; and an alertness deciding step of causing an alertness deciding section to decide alertness of the user on the basis of a result of the analysis by the eye-behavior analyzing section.

In addition, the series of processes explained in the specification can be executed by hardware, software, or a composite configuration of hardware and software. In a case where the processes are executed by software, a program in which a process sequence is recorded can be installed into a memory in a computer incorporated into dedicated hardware, and can be executed thereon, or the program can be installed on a general-purpose computer that can execute various types of processes, and can be executed thereon. For example, the program can be recorded in advance on a recording medium. Other than being installed on a computer from the recording medium, the program can be received via a network like a LAN (Local Area Network) or the Internet, and installed on a built-in recording medium such as a hard disk.

While problem presentation of information that prompts main eye behaviors is explained mainly in the present specification, in other problems that can be used also, at the time point when the necessity for transfer to manual driving arises, a reason for the case of the transfer or the like may be displayed in visual message information from a system, and it may be decided whether or not the cognition of the message has occurred. That is, eye behaviors of the driver at the time when the driver checks the message are analyzed, and it is decided whether or not the cognition of the message has occurred.

Eye behaviors vary depending on people due to orthoptics of squints or monovision, and there can be differences of information search behaviors between right eyes and left eyes. Accordingly, analyses of both eyes, analyses of a single eye according to the distance to a problem, or the like may be performed.

While eye behavior analyses are used for alertness state decisions at the time of transfers from automated driving to manual driving in the examples explained in the present specification, results of the eye behavior analyses may be applied to estimation of the mental states of drivers, computations of disorder prediction coefficients, and the like, along with other vital information and action information of the drivers, and mental health monitoring may thereby be performed.

Note that various types of processes described in the specification may not only be executed in a temporal sequence according to the descriptions, but also be executed in parallel or separately as necessary or according to the processing capability of an apparatus to execute the processes. In addition, a system in the present specification has a logical set configuration of plural apparatuses, and is not limited to one that includes apparatuses of configurations that are housed within a single housing.

INDUSTRIAL APPLICABILITY

As explained above, according to the configuration of one embodiment of the present disclosure, a configuration that decides whether or not the driver has alertness sufficient for manual driving by analyzing eye behaviors of the driver trying to solve the problem displayed on the display section is realized.

Specifically, for example, it is made possible to decide whether or not the driver of the moving apparatus that can be driven in a driving mode that can be switched to automated driving and manual driving has alertness sufficient to return to manual driving on the basis of eye behaviors of the driver. An eye-behavior analyzing section that analyzes an eye behavior of a driver who observes a problem displayed on a display section and an alertness deciding section that decides alertness of the driver on the basis of a result of the analysis by the eye-behavior analyzing section are included. The alertness deciding section analyzes whether or not the driver executes an eye behavior such as a fixation or a microsaccade for solving the problem, and decides whether or not the driver has alertness sufficient to return to manual driving.

According to the present configuration, a configuration that decides whether or not the driver has alertness sufficient for manual driving by analyzing eye behaviors of the driver trying to solve the problem displayed on the display section is realized.

REFERENCE SIGNS LIST

10: Automobile
11: Data processing section
12: Driver-information acquiring section
13: Environment information acquiring section
14: Communication section
15: Notifying section
17: Display-information storage section
20: Driver
30: Server
51: Driver facial tracking section (driver facial tracker)
52: Driver-eye tracking section (driver eye tracker)
61: Display-information generating section
62: Display-section selecting section
63: Driver-eye-behavior analyzing section
64: Driver-eye-behavior learner
65: Driver-alertness deciding section
71 to 74: Display section
100: Moving apparatus
101: Input section
102: Data acquiring section
103: Communication section
104: Vehicle interior equipment
105: Output control section 106: Output section
107: Drive-system control section
108: Drive system
109: Body-system control section
110: Body system
111: Storage section
112: Automated-driving control section
121: Communication network
131: Detecting section
132: Current-position estimating section
133: Situation analyzing section
134: Planning section
135: Operation control section
141: Vehicle-exterior-information detecting section
142: Vehicle-interior-information detecting section
143: Vehicle-state detecting section
151: Map analyzing section
152: Traffic-rule recognizing section
153: Situation recognizing section
154: Situation predicting section
155: Safety deciding section
161: Route planning section
162: Action planning section
163: Operation planning section
171: Emergency avoiding section
172: Acceleration/deceleration control section
173: Direction control section
501: CPU
502: ROM
503: RAM
504: Bus
505: Input/output interface
506: Input section
507: Output section
508: Storage section
509: Communication section
510: Drive
511: Removable medium
521: Sensor
522: Drive section

The invention claimed is:

1. An information processing apparatus comprising:
a training section generating a training dictionary for a user;
a display-information generating section that generates or acquires a problem and causes a display section to display the problem;
one or more first sensors detecting eye motion of the user;
one or more second sensors detecting one or more vital signs of the user;
one or more third sensors detecting a torque and a force applied to a steering wheel by the user:
an eye-behavior analyzing section that analyzes the eye motion of the user who observes the problem displayed on the display section and outputs eye behavior information comprising a saccade, a fixation, and a microsaccade;
an alertness deciding section communicating with the eye-behavior analyzing section that decides alertness of the user on a basis of a result of the analysis by the eye-behavior analyzing section, the eye behavior information, the one or more vital signs of the user, the torque and the force applied to the steering wheel by the user, and the training dictionary for the user; and
an eye-behavior learning section communicating with the eye-behavior analyzing section that learns correspondence between the eye behavior information of the user, the one or more vital signs of the user, the torque and the force applied to the steering wheel by the user, and a level of the alertness of the user and stores the correspondence in the training dictionary.

2. The information processing apparatus according to claim 1, wherein the problem is a problem that requires work of additionally searching for missing information in order for the user to solve a problem.

3. The information processing apparatus according to claim 1, wherein the problem is a problem that triggers at least any one eye behavior of the saccade, the fixation, or the microsaccade of an eye as an eye behavior executed by the user to solve a problem.

4. The information processing apparatus according to claim 1, wherein the eye-behavior analyzing section acquires data that allows a decision as to whether or not the user is executing an eye behavior for solving the problem.

5. The information processing apparatus according to claim 1, wherein the eye-behavior analyzing section acquires data representing whether or not the user is executing at least any one eye behavior of the saccade, the fixation, or the microsaccade of an eye as an eye behavior for solving the problem.

6. The information processing apparatus according to claim 1, wherein the alertness deciding section receives, as an input from the eye-behavior analyzing section, data that allows a decision as to whether or not the user is executing an eye behavior for solving the problem, and decides the alertness of the user on a basis of the input data.

7. The information processing apparatus according to claim 1, wherein the alertness deciding section receives, as an input from the eye-behavior analyzing section, data representing whether or not the user is executing at least any one eye behavior of the saccade, the fixation, or the microsaccade of an eye, and decides the alertness of the user on a basis of the input data.

8. The information processing apparatus according to claim 1, wherein the alertness deciding section decides that the alertness of the user is high in a case where an eye behavior of the user is decided as an eye behavior for solving the problem, and decides that the alertness of the user is low in a case where an eye behavior of the user is not decided as an eye behavior for solving the problem.

9. The information processing apparatus according to claim 1, wherein the alertness deciding section decides that the alertness of the user is high in a case where it is decided that the user is executing at least any one eye behavior of the saccade, the fixation, or the microsaccade of an eye as an eye behavior for solving the problem.

10. The information processing apparatus according to claim 1, wherein the alertness deciding section decides whether or not the user has alertness sufficient to execute manual driving.

11. The information processing apparatus according to claim 1, wherein the problem generated or acquired by the display-information generating section is a problem that involves plural arrayed silhouettes representing objects and that requires a line-of-sight movement to each silhouette for problem solving.

12. The information processing apparatus according to claim 1, wherein the problem generated or acquired by the display-information generating section is a problem that involves data of at least any one of arrayed characters, symbols, signs, or pictograms and that requires a line-of-sight movement to each piece of data for problem solving.

13. A moving apparatus that is capable of being switched to automated driving and manual driving, the moving apparatus comprising:
   a training section generating a training dictionary for a driver;
   one or more first sensors detecting eye motion of the driver;
   one or more second sensors detecting one or more vital signs of the driver;
   one or more third sensors detecting a torque and a force applied to a steering wheel by the driver;
   a driver-information acquiring section that acquires driver information of the driver of the moving apparatus; and
   a data processing section that decides whether or not the driver has alertness sufficient to return to manual driving, on a basis of acquisition information of the driver-information acquiring section, wherein
   the data processing section has
      a display-information generating section that generates or acquires a problem and causes a display section to display the problem,
      an eye-behavior analyzing section that analyzes the eye motion of the driver who observes the problem displayed on the display section and outputs eye behavior information comprising a saccade, a fixation, and a microsaccade,
      an alertness deciding section communicating with the eye-behavior analyzing section that decides alertness of the driver on a basis of a result of the analysis by the eye-behavior analyzing section, the eye behavior information, the one or more vital signs of the driver, the torque and the force applied to the steering wheel by the driver, and the training dictionary for the driver, and
      an eye-behavior learning section communicating with the eye-behavior analyzing section that learns correspondence between the eye behavior information of the driver, the one or more vital signs of the driver, the torque and the force applied to the steering wheel by the driver, and a level of the alertness of the driver and stores the correspondence in the training dictionary.

14. The moving apparatus according to claim 13, wherein the alertness deciding section receives, as an input from the eye-behavior analyzing section, data that allows a decision as to whether or not the driver is executing an eye behavior for solving the problem, and decides, on a basis of the input data, whether or not the driver has alertness sufficient to return to manual driving.

15. The moving apparatus according to claim 13, wherein the alertness deciding section receives, as an input from the eye-behavior analyzing section, data representing whether or not the driver is executing at least any one eye behavior of the saccade, the fixation, or the microsaccade of an eye, and decides, on a basis of the input data, whether or not the driver has alertness sufficient to return to manual driving.

16. The moving apparatus according to claim 13, wherein the control section of the moving apparatus permits a start of manual driving by the driver in a case where the alertness deciding section decides that the driver has alertness sufficient to return to manual driving, and
   the control section of the moving apparatus does not permit a start of manual driving by the driver and executes a process of avoiding an entrance into a manual driving zone in a case where the alertness deciding section decides that the driver does not have alertness sufficient to return to manual driving.

17. An information processing method executed in an information processing apparatus, the information processing method comprising:
   a training step generating a training dictionary for a user;
   a first sensing step, performed by one or more first sensors of detecting eye motion of the user:
   a second sensing step, performed by one or more second sensors of detecting one or more vital signs of the user;
   a third sensing step, performed by one or more third sensors of detecting a torque and a force applied to a steering wheel by the user;
   a display-information generating step, performed by a display-information generating section, of generating or acquiring a problem and causing a display section to display the problem;
   an eye-behavior analyzing step, performed by an eye-behavior analyzing section, of analyzing the eye motion of the user who observes the problem displayed on the display section and outputs eye behavior information comprising a saccade, a fixation, and a microsaccade;
   an alertness deciding step, performed by an alertness deciding section, of deciding alertness of the user on a basis of a result of the analysis by the eye-behavior analyzing section, the eye behavior information, the one or more vital signs of the user, the torque and the force applied to the steering wheel by the user, and the training dictionary of the user; and
   an eye-behavior learning step, performed by an eye-behavior learning section, of learning correspondence between the eye behavior information of the user, the one or more vital signs of the user, the torque and the force applied to the steering wheel by the user, and a level of the alertness of the user, and storing the correspondence in the training dictionary.

18. An information processing method executed in a moving apparatus, the moving apparatus being capable of being switched to automated driving and manual driving, the information processing method comprising:
   a training step generating a training dictionary for a driver;
   a first sensing step, performed by one or more first sensors of detecting eye motion of the driver;
   a second sensing step, performed by one or more second sensors of detecting one or more vital signs of the driver;
   a third sensing step, performed by one or more third sensors of detecting a torque and a force applied to a steering wheel by the driver;
   a driver-information acquiring step, performed by a driver-information acquiring section, of acquiring driver information of the driver of the moving apparatus; and
   a data processing step, performed by a data processing section, of deciding whether or not the driver has alertness sufficient to return to manual driving, on a basis of the driver information, wherein
   the data processing step includes
      a display-information generating step, performed by a display-information generating section, of generating or acquiring a problem and causing a display section to display the problem,
      an eye-behavior analyzing step, performed by an eye-behavior analyzing section, of analyzing the eye motion of the driver who observes the problem displayed on the display section and outputs eye behavior information comprising a saccade, a fixation, and a microsaccade, an alertness deciding step, performed by an alertness deciding section, of deciding alertness of the user on a basis of a result of the analysis by the eye-behavior analyzing section, the eye behavior information, the one or more vital signs of the driver, the torque and the force applied to the steering wheel by the driver, and the training dictionary for the driver, and an eye-behavior learning step, performed by an eye-behavior learning section, of learning correspondence between the eye behavior information of the user and a level of the alertness of the driver, the one or more vital signs of the driver, the torque and the force applied to the steering wheel by the driver, and storing the correspondence in the training dictionary.

19. A program stored on a non-transitory computer-readable medium that causes an information processing apparatus to execute information processing including:

a training section generating a training dictionary for a user;

a first sensing step, performed by one or more first sensors of detecting eye motion of the user:

a second sensing step, performed by one or more second sensors of detecting one or more vital signs of the user;

a third sensing step, performed by one or more third sensors of detecting a torque and a force applied to a steering wheel by the user;

a display-information generating step of causing a display-information generating section to generate or acquire a problem and cause a display section to display the problem;

an eye-behavior analyzing step of causing an eye-behavior analyzing section to analyze the eye motion of the user who observes the problem displayed on the display section and outputs eye behavior information comprising a saccade, a fixation, and a microsaccade;

an alertness deciding step of causing an alertness deciding section to decide alertness of the user on a basis of a result of the analysis by the eye-behavior analyzing section, the eye behavior information, the one or more vital signs of the user, the torque and the force applied to the steering wheel by the user, and the training dictionary for the user; and an eye-behavior learning step of learning correspondence between the eye behavior information of the user, the one or more vital signs of the user, the torque and the force applied to the steering wheel by the user, and a level of the alertness of the user and storing the correspondence in the training dictionary.

* * * * *